(12) United States Patent
Lerchen et al.

(10) Patent No.: US 7,220,824 B1
(45) Date of Patent: May 22, 2007

(54) INTEGRIN-MEDIATED DRUG TARGETING

(75) Inventors: Hans-Georg Lerchen, Leverkusen (DE); Jörg Baumgarten, Wuppertal (DE); Ulf Brüggemeier, Leichlingen (DE); Markus Albers, Leverkusen (DE); Andreas Schoop, Vienna (AT); Thomas-J. Schulze, Thousand Oaks, CA (US)

(73) Assignee: Bayer Aktiengesellschaft, Leverkusen (DE)

( * ) Notice: Subject to any disclaimer, the term of this patent is extended or adjusted under 35 U.S.C. 154(b) by 380 days.

(21) Appl. No.: 10/070,208

(22) PCT Filed: Aug. 28, 2000

(86) PCT No.: PCT/EP00/08361

§ 371 (c)(1),
(2), (4) Date: Jun. 27, 2002

(87) PCT Pub. No.: WO01/17563

PCT Pub. Date: Mar. 15, 2001

(51) Int. Cl.
*A61K 38/14* (2006.01)
(52) U.S. Cl. .................................. 530/322; 514/25
(58) Field of Classification Search ............... 530/322; 514/25
See application file for complete search history.

(56) References Cited

U.S. PATENT DOCUMENTS

| | | | |
|---|---|---|---|
| 4,757,072 A | 7/1988 | Kabbe et al. | 514/257 |
| 4,943,579 A | 7/1990 | Vishnuvajjala et al. | 514/283 |
| 4,975,278 A | 12/1990 | Senter et al. | 424/94.3 |
| 4,980,343 A | 12/1990 | Stella et al. | 514/18 |
| 5,464,796 A | 11/1995 | Petersen et al. | 514/312 |
| 5,955,100 A | 9/1999 | Bosslet et al. | 424/450 |
| 6,271,342 B1 * | 8/2001 | Lerchen et al. | 530/322 |

FOREIGN PATENT DOCUMENTS

| | | |
|---|---|---|
| EP | 0501250 | 9/1992 |
| EP | 0511917 | 11/1992 |
| EP | 0516861 | 12/1992 |
| EP | 0595133 | 5/1994 |
| WO | 8807378 | 10/1988 |
| WO | 9212146 | 7/1992 |
| WO | 9320229 | 10/1993 |
| WO | 9405681 | 3/1994 |
| WO | 9602546 | 2/1996 |
| WO | 9810795 | 3/1998 |

OTHER PUBLICATIONS

Brooks et al., "Antiintergrin alpha V beta 3 blocks human breast cancer growth and angiogenesis in human skin" J. Clin Invest, 1995, vol. 96, pp. 1815-1822.*
Uhm, J. H., Dooley, N. P., Kyritsis, A. P., Rao, J. S., Gladson, C. L., "Vitronectin, a Glioma-derived Extracellular Matrix Protein, Protects Tumor Cells from Apoptotic Death", Clinical Cancer Research, 5: 1587-1594 (Jun. 1999).
Damiano, J. S., Cress, A. E., Hazlehurst, L. A., Shtil, A. A., Dalton, W. S., "Cell Adhesion Mediated Drug Resistance (CAM-DR): Role of Integrin and Resistance to Apoptosis in Human Myeloma Cell Lines", Blood, 93(5): 1658-1667 (Mar. 1999).
Varner, J. A., Cheresh, D. A., "Integrins and Cancer", Current Opinion in Cell Biology, 8: 724-730 (1996).
Bitan, G., Scheibler, L., Greenberg, Z., Rosenblat, M., Chorev, M., "Mapping the Integrin αvβ3-Ligand Interface by Photoaffinity Cross-Linking", Biochemistry, 38: 3414-3420 (1999).
Fields, G. B., "Integrins: cell adhesion molecules in cancer", Exp. Opin. Ther. Patents, 8(6): 633-644 (1998).
Kerr, J. S., "Novel Small Molecule α v Integrin Antagonists: Comparative Anti-Cancer Efficacy with Known Angiogenesis Inhibitors", Anticancer Research, 19(2A): 959-968 (1999).
Carron, C. P., "A Peptidomimetic Antagonist of the Integrin αvβ3 Inhibits Leydig Cell Tumor Growth and the Development Hypercalcemia of Malignancy", Cancer Res., 58: 1930-1935 (May 1998).
Nickols, A., "Antiangiogenic and Anticancer Activites of Antagonists of Integrin αvβ3", Proc. Annu. Meet. AACR., 38(1): 206 (Mar. 1997), Abstract No. 1389.
Macdonald, T. J., "Migration of Human Brain Tumor Cells and Human rain Endothelial Cells on Tenscin Requires the Integrin αvβ3; a Unifying Model for Grain Tumor Invasion and Angiogenesis", Proc. Annu. Meet., AACR, 39:497 (Mar. 1998), Abstract No. 3382.
Brooks, P. C., "Requirements of Vascular Integrin αvβ3 for Angiogenesis", Science, 264: 569-571 (Apr. 1994).
Brooks, P. C., "Integrin αvβ3 Antagonists Promote Tumor Regression by Inducing Apoptosis of Angiogenic Blood Vessels", Cell. 79(7): 1157-1164 (Dec. 1994).
Varner, J. A., "Tumor Angiogenesis and The Role of Vascular Cell Integrin αvβ3", Important Advances in Oncology, pp. 69-87 (1996).
Varner, J. A., "Review: The Integrin αvβ3: Angiogenesis and Apoptosis", Cell Adhesion and Communication, 3(4):367-374 (1995).
Gasparini, G., "The Rationale and Future Potential of Angiogenesis Inhibitors in Neoplasma", Drugs. 58(1): 17-38 (Jul. 1999).
Mueller, B. M., "Pre-clinical Therapy of Human Melanoma with Morpholino-doxorubicin Conjugated to a Monoclonal Antibody Directed Against an Integrin on Melanoma Cells". Antibody, Immunoconjugates, Radiopharm., 4(2): 99-106 (1991).

(Continued)

Primary Examiner—Bruce R. Campbell
Assistant Examiner—Roy Teller

(57) ABSTRACT

The present invention relates to cytostatics which have a tumour-specific action as a result of linkage to $\alpha_v\beta_3$ integrin antagonists via preferred linking units. The preferred linking units guarantee serum stability of the conjugate of cytostatic and $\alpha_v\beta_3$ integrin antagonist and at the same time the desired intracellular action in tumour cells as a result of their enzymatic or hydrolytic cleavability with release of the cytostatic.

10 Claims, No Drawings

OTHER PUBLICATIONS

Sheu Joen, R., "Triflavin, an arg-gly-asp-containing peptide, inhibits the adhesion of tumor cells to matrix proteins via binding to multiple integrin receptors expressed on human hepatoma cells", Proc. Soc. Exp. Biol. Med., 213(1): 71-79 (1996).

Ashwell, G., Harford, J., "Carbohydrate-Specific Receptors of the Liver", Ann. Rev. Biochem., 51:531-554 (1982).

Aminoff, D., Bruegge, W., Bell, W., Sarpolis, K., Williams, R., "Role of Sialic Acid in Survival of Erythrocytes in the Circulation: Interaction of Neuraminidase-Treated and Untreated Erythrocytes With Spleen and Liver at the Cellular Level", Proc. Natl. Acad. Sci. USA, 74: 1521-1524 (Apr. 1977).

Haltiwanger, R., Lehrman, M., Eckhardt, A., Hill, R., "The Distribution and Localization of the Fucose-Binding Lectin in Rat Tissues and the Identification of a High Affinity Form of the Mannose/N-Acetylglucosamine-Binding Lectin in Rat Liver", J. of Biol. Chem., 261: 7433-7439 (Jun. 1986).

Jansen, R., Molema, G., Ching, T., Oosting, R., Harms, G., Moolenaar, F., Hardonk, M., Meijer, D., "Hepatic Endocytosis of Various Types of Mannose-Terminated Albumins", J. of Biol. Chem., 266:3343-3348 (Feb., 1991).

Wall, M., Wani, M., Cook, C., Palmer, K., McPhail, A., Sim, G., "Plant Antitumor Agents. I. The Isolation and Structure of Camptothecin, A Novel Alkaloidal Leukemia and Tumor Inhibitor from Camptotheca Acuminata", J. of Am. Chem. Society, 88: 3888-3890 (Aug. 1966).

Brooks, P., Montgomery, A., Rosenfeld, M., Reisfeld, R., Hu, T., Klier. G., Cheresh, D., "Integrin $\alpha v \beta_3$ Antagonists Promote Tumor Regression by Inducing Apoptosis of Angiogenic Blood Vessels", Cell, 79: 1157-1164 (Dec., 1994).

Brooks, P., Stromblad, S., Klemke, R., Visscher, D., Sarkar, F., Cheresh, D., "Antiintegrin $\alpha v \beta_3$ Blocks Human Breast Cancer Growth and Angiogenesis in Human Skin", J. Clin. Invest., 96: 1815-1822 (Oct., 1995).

Fitzpatrick, J., Garnett, M., "Design, Synthesis and In Vitro Testing of Methotrexate Carrier Conjugates Linked Via Oligopeptide Spacers", Anti-Cancer Drug Design, 10: 1-9 (1995).

Gabius, H., "Endogene Lektine in Tumoren Und Ihre Mogliche Bedeutung Fur Diagnose Und Therapie Von Krebserkrankungen", Onkologic, 12: 175-181 (Apr. 1989).

* cited by examiner

INTEGRIN-MEDIATED DRUG TARGETING

This is a National Stage filing under 35 U.S.C. 371 of International Application Number PCT/EP00/08361, filed Aug. 28, 2000, which claims priority of U.S. application Ser. No. 09/392,167, filed Sep. 8, 1999, and 09/606,772, filed Jun. 29, 2000, both now abandoned.

The marked lectin pattern on tumour cell surfaces (Gabius; Onkologie 12, (1989), 175) opens up the fundamental possibility of addressing these specifically on tumour cells by linkage of appropriate carbohydrate units to cytostatics. This prospect is restricted by the fact that, even in other tissues, in particular in the liver, lectins having similar carbohydrate specificities (galactose, lactose, mannose, N-acetylglucosamine, fucose etc.) occur (Ashwell et al., Annu. Rev. Biochem. 46 (1982), 531; Stahl et al. Proc. Natl. Acad. Sci. USA 74 (1977), 1521; Hill et al., J. Biol. Chem. 262 (1986), 7433; Jansen et al., J. Biol. Chem. 266 (1991), 3343). Accordingly, a marked concentration of active compound-containing glycoconjugates in the liver and other lectin-rich organs must be expected if, in this approach, carbohydrates are used without particular modification establishing a selectivity to tumour tissue.

The heterocyclic amine batracylin (1) shows a good antitumour action in various stomach cancer models (U.S. Pat. No. 4,757,072).

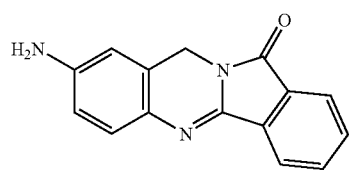

(1)

Peptide conjugates of (1) having good in-vitro action and more favourable solubility properties (U.S. Pat. No. 4,180,343) are more poorly tolerable in animal experiments than free batracylin. The fucose conjugates of batracylin (1) described in EP-A-0 501 250 disadvantageously concentrate very strongly in the liver.

Quinolone-a (2), 7-[(3a-R,S, 4-R,S, 7a-S,R)-4-amino-1,3,3a,4,7,7a-hexahydro-iso-indol-2-yl]-8-chloro-1-cyclopropyl-6-fluoro-1,4-dihydro-4-oxo-3-quinolinecarboxylic acid, also shows, in addition to its outstanding antibacterial activity, a very good activity against various tumour cell lines (EP-A-0 520 240, JP-4 253 973). However, considerable toxicological problems face it (e.g. genotoxicity, bone marrow toxicity, high acute toxicity in vivo etc.).

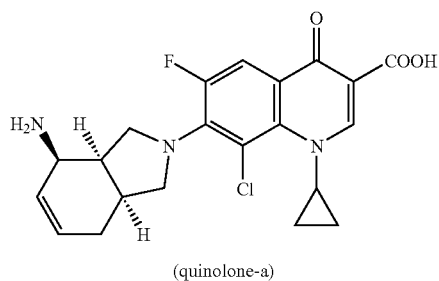

(2)

(quinolone-a)

20(S)-Camptothecin is a pentacyclic alkaloid which was isolated in 1966 by Wall et al. (J. Am. Chem. Soc. 88, 3888 (1966)). It has a high active antitumour potential in numerous in-vitro and in-vivo tests. Unfortunately, however, the realization of the promising potential in the clinical investigation phase failed because of toxicity and solubility problems.

By opening of the E ring lactone and formation of the sodium salt, a water-soluble compound was obtained which is in a pH-dependent equilibrium with the ring-closed form. Here too, clinical studies have not led to success as yet.

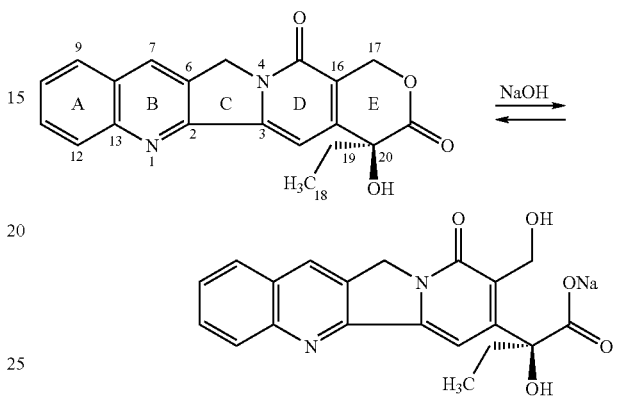

About 20 years later, it was found that the biological activity is to be attributed to enzyme inhibition of topoisomerase I. Since then, the research activities have again been increased in order to find a camptothecin derivative which is more tolerable and which is active in vivo.

For improvement of the water solubility, salts of A ring- and B ring-modified camptothecin derivatives and of 20-O-acyl derivatives with ionizable groups have been described (Vishnuvajjala et al. U.S. Pat. No. 4,943,579). The latter prodrug concept was later also transferred to modified camptothecin derivatives (Wani et al. WO 9602546). The described 20-O-acyl prodrugs, however, have a very short half-life in vivo and are very rapidly cleaved to give the parent structure.

WO 96/31532 describes carbohydrate-modified cytostatics in which both serum stability and release of the cytostatic within the tumour cells and a specific concentration of the cytostatic in tumour tissue is achieved by a novel linkage of selectively modified carbohydrates to cytostatics (for example batracylin, quinolone-a, camptothecin) via preferred spacer and linker groups.

Integrins are heterodimeric transmembrane proteins found on the surface of cells, which play an important part in the adhesion of the cells to an extracellular matrix. They recognize extracellular glycoproteins such as fibronectin or vitronectin on the extracellular matrix via the RGD sequence occurring in these proteins (RGD is the single-letter code for the amino acid sequence arginine-glycine-aspartate).

In general, integrins such as, for example, the vitronectin receptor, which is also called the $\alpha_v\beta_3$ receptor, or alternatively the $\alpha_v\beta_5$ receptor or the GpIIb/IIIMa receptor play an important part in biological processes such as cell migration, angiogenesis and cell-matrix adhesion and thus for diseases in which these processes are crucial steps. Cancer, osteoporosis, arteriosclerosis, restenosis and ophthalmia may be mentioned by way of example.

The $\alpha_v\beta_3$ receptor occurs, for example, in large amounts on growing endothelial cells and makes possible their adhesion to an extracellular matrix. The $_{v\ 3}$ receptor thus plays an important part in angiogenesis, i.e. the formation of new blood vessels, which is a crucial prerequisite for tumour growth and metastasis formation in carcinomatous disorders.

It was possible to show that the blockade of the above-mentioned receptors is an important starting point for the treatment of disorders of this type. If the adhesion of growing endothelial cells to an extracellular matrix is suppressed by blocking their corresponding integrin receptors, for example, by a cyclic peptide or a monoclonal antibody, the endothelial cells die. Angiogenesis therefore does not occur, which leads to a stoppage or regression of tumour growth (cf, for example, Brooks et al., Cell, Volume 79, 1157–1164, 1994).

Moreover, the invasive properties of tumour cells and thus their capability to form metastases markedly decrease when their $\alpha_v\beta_3$ receptor is blocked by an antibody (Brooks et al., J. Clin. Invest., Volume 96, 1815, 1995).

WO 98/10795 describes conjugates in which a molecule adding to tumours is linked to a functional unit such as, for example, a cytostatic or a detectable label such as, for example, a radioactive nuclide. Inter alia, integrin antagonists such as, for example, peptides having the RGD sequence described above are described as molecules adding to tumours. Doxorubicin is described as an example of a cytostatic which is linked to a molecule of this type addressing tumours.

In the case of the compounds of WO 98/10795, the linkage is carried out such that the molecule addressing a tumour and the functional unit are directly bonded to one another with retention of their respective properties (cf., for example, p. 56, l. 17, to p. 58, l. 10, and Ex. 6). This has the result that these compounds are indeed selectively concentrated in the immediate vicinity of tumour cells by binding of the entity addressing a tumour (in the case of a radical having $\alpha_v\beta_3$ integrin-antagonistic action by binding to the $\alpha_v\beta_3$ integrin receptor which, in particular, is expressed on endothelial cells newly formed by angiogenesis), but on account of the direct combination the functional unit such as, for example, a cytostatic cannot be released into the intracellular space of the tumour tissue.

Fundamentally, the conjugate which on the one hand is selectively concentrated in tumour tissue by the effect of a part addressing $\alpha_v\beta_3$ or $\alpha_v\beta_5$ integrin receptors found in the conjugate, but on the other hand comprises a cytostatic which can be released from the conjugate, should have an increased toxophoric effect on tumour tissue due to the possibility of the more direct action of the cytostatic on the tumour cells compared with the conjugates described in WO 98/10795.

It was therefore the object of the present invention to develop conjugates which comprise a moiety addressing $\alpha_v\beta_3$ or $\alpha_v\beta_5$ integrin receptors and a cytostatic which can be released from the conjugate, where the moiety in the conjugate addressing $\alpha_v\beta_3$ or $\alpha_v\beta_5$ integrin receptors retains its ability to bind to the $\alpha_v\beta_3$ or $\alpha_v\beta_5$ integrin receptor.

The above object is achieved by conjugates which comprise a non-peptide moiety addressing $\alpha_v\beta_3$ or $\alpha_v\beta_5$ integrin receptors, a cytostatic and a linking unit which is enzymatically or hydrolytically cleavable with release of the cytostatic. Conjugates having a non-peptide moiety addressing $\alpha_v\beta_3$ integrin receptors are particularly preferred here.

In principle, medicament-containing conjugates are complex, difficult-to-prepare compounds, as is explained, for example, in Anti-Cancer Drug Design 10 (1995), 1–9, in particular p. 1. In this article, conjugates of the cytostatic methotrexate, an oligopeptide spacer and a protein (human serum albumin) are described. However, it is also pointed out (cf. p. 7, first paragraph) that the nature of the linking unit and the type of linkage of this unit to the toxophore and the carrier (for example an antibody) can affect the cleavage of the linking unit. This article therefore teaches that the linkage presented there cannot be transferred to other conjugate systems without difficulty. In particular, nothing is said about whether moieties addressed also to $\alpha_v\beta_3$ or $\alpha_v\beta_5$ integrin receptors in this manner can be linked to toxophores without the moiety addressing $\alpha_v\beta_3$ or $\alpha_v\beta_5$ integrin receptors by this means losing its ability to bind to $\alpha_v\beta_3$ or $\alpha_v\beta_5$ integrin receptors.

The linking units disclosed in WO 96/31532 are used specifically for the linkage of a toxophore to an oligosaccharide radical. Nothing is said about whether moieties addressed also to $\alpha_v\beta_3$ or $\alpha_v\beta_5$ integrin receptors can be linked to toxophores in this manner, without, by this means, the moiety addressing $\alpha_v\beta_3$ or $\alpha_v\beta_5$ integrin receptors losing its ability to bind to $\alpha_v\beta_3$ or $\alpha_v\beta_5$ integrin receptors.

According to a preferred embodiment of the present invention, the linking unit can be cleaved by tumour-associated enzymes. This leads to a further increase in the tissue specificity of the conjugates according to the invention and thus to an additional decrease of the conjugates according to the invention in other tissue types.

According to a further preferred embodiment of the invention, the linking unit can be cleaved by enzymes which are coupled to antibodies with selectivity for tumour tissue and are thus addressed to tumour tissue. This is also called the ADEPT approach. This likewise leads to a further increase in the tissue specificity of the conjugates according to the invention and thus to an additional decrease of the conjugates according to the invention in other tissue types.

Particularly preferred conjugates according to the present invention are those of the general formula (1)

CT-AA1-AA2-AA3-AA4-Sp-IA         (I)

in which

CT denotes a cytotoxic radical or a radical of a cytostatic or of a cytostatic derivative, which can additionally carry a hydroxyl, carboxyl or amino group, AA1 is absent or is an amino acid in the D or L configuration, which can optionally carry protective groups or a radical Sp', AA2 is absent or is an amino acid in the D or L configuration, which can optionally carry protective groups or a radical Sp', AA3 is absent or is an amino acid in the D or L configuration, which can optionally carry protective groups or a radical Sp', AA4 is absent or is an amino acid in the D or L configuration, which can optionally carry protective groups or a radical Sp', in which Sp' is an arylaminocarbonyl or an arylaminothiocarbonyl radical having 7–11 carbon atoms, Sp is absent, is an arylaminocarbonyl or an arylaminothiocarbonyl radical having 7–11 carbon atoms or is an alkanedicarboxylic acid radical having 3 to 8 carbon atoms or a carbonyl or a thiocarbonyl radical, with the proviso that at least one of the radicals AA1 to AA4 and/or Sp is present, IA is a non-peptide radical addressing an $\alpha_v\beta_3$ integrin receptor, which is selected from the group consisting of A) a radical of the formula (II)

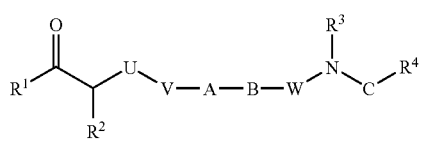

in which
- R¹ is OH, a substituted or unsubstituted alkoxy or cycloalkoxy radical, a substituted or unsubstituted aryloxy radical or a saturated or unsaturated, optionally substituted heterocyclyloxy radical, or optionally represents a direct bond or an atom from the group consisting of O, N and S, via which the radical of the formula (II) is bonded to the rest of the conjugate;
- R² is hydrogen, a substituted or unsubstituted alkyl or cycloalkyl radical, a substituted or unsubstituted aryl radical, a saturated or unsaturated, optionally substituted heterocyclic radical, an optionally substituted alkenyl radical or an optionally substituted alkinyl radical, via which the radical of the formula (II) is optionally bonded to the rest of the conjugate, or is —NR²'₂, —NR²'SO₂R²''', —NR²'COOR²''', —NR²'COR²''', —NR²'CO—NR²'₂ or —NR²'CSNR²'₂;

in which
R²' independently of one another is hydrogen, a substituted or unsubstituted alkyl or cycloalkyl radical, a substituted or unsubstituted aryl radical or a saturated or unsaturated, optionally substituted heterocyclic radical, or optionally represents a direct bond, via which the radical of the formula (II) is bonded to the rest of the conjugate;
- R²'' is a substituted or unsubstituted alkyl or cycloalkyl radical, a substituted or unsubstituted aryl radical or a saturated or unsaturated, optionally substituted heterocyclic radical, via which the radical of the formula (II) is optionally bonded to the rest of the conjugate;
- U is a direct bond or a substituted or unsubstituted alkylene group, via which the radical of the formula (II) is optionally bonded to the rest of the conjugate;
- V is a substituted or unsubstituted alkylene group, —NR²'CO— or —NR²'SO₂—, via which the radical of the formula (II) is optionally bonded to the rest of the conjugate;
- A and B each independently of one another is a 1,3- or 1,4-bridged, optionally additionally substituted phenylene group;
- W is a direct bond or a substituted or unsubstituted alkylene group;

C is absent or is 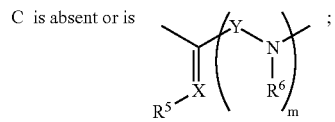 ;

- R³ is hydrogen, a substituted or unsubstituted alkyl or cycloalkyl radical, a substituted or unsubstituted aryl radical, a saturated or unsaturated, optionally substituted heterocyclic radical, an alkylamine radical, an alkylamide radical or is bonded to one of R⁴, Y, R⁵ or R⁶, if present, with formation of an optionally substituted heterocyclic ring system which includes the nitrogen atom to which R³ is bonded and can be saturated or unsaturated and/or can contain further heteroatoms;
- R⁴ is hydrogen, a substituted or unsubstituted alkyl or cycloalkyl radical, a substituted or unsubstituted aryl radical, a saturated or unsaturated, optionally substituted heterocyclic radical, an alkylamine radical, an alkylamide radical or is bonded to one of R³, Y, R⁵ or R⁶, if present, with formation of an optionally substituted heterocyclic ring system which includes the nitrogen atom to which R⁴ is bonded and can be saturated or unsaturated and/or can contain further heteroatoms, or optionally represents a direct bond, via which the radical of the formula (II) is bonded to the rest of the conjugate;
- x is O, N or S;
- m is 0 or 1;
- Y is a direct bond or an optionally substituted alkylene or alkine group;
- R⁵ is absent, —NO₂, —CN, —COR⁵', —COOR⁵'', or is bonded to one of R³, Y, R⁴ or R⁶, if present, with formation of an optionally substituted carbocyclic or heterocyclic ring system which includes X and can be saturated or unsaturated and/or can contain further heteroatoms;
- R⁵' is hydrogen, a substituted or unsubstituted alkyl or cycloalkyl radical, a substituted or unsubstituted aryl radical or a saturated or unsaturated, optionally substituted heterocyclic radical which can be saturated or unsaturated and/or can contain further heteroatoms;
- R⁶ is hydrogen, a substituted or unsubstituted alkyl or cycloalkyl radical, a substituted or unsubstituted aryl radical, a saturated or unsaturated, optionally substituted heterocyclic radical, an alkylamine radical, an alkylamide radical or is bonded to one of R³, R⁴, Y or R⁵, if present, with formation of an optionally substituted heterocyclic ring system which includes the nitrogen atom to which R⁶ is bonded and can be saturated or unsaturated and/or can contain further heteroatoms;

or

B) a radical of the formula (III)

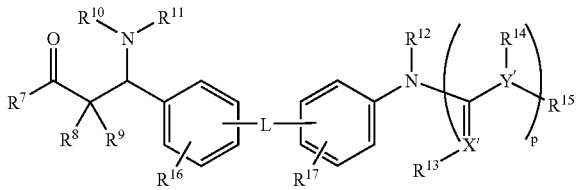

in which
- R⁷ is OH, a substituted or unsubstituted alkoxy or cycloalkoxy radical, a substituted or unsubstituted aryloxy radical or a saturated or unsaturated, optionally substituted heterocyclyloxy radical, or optionally represents a direct bond or an atom from the group consisting of N, O and S, via which the radical of the formula (III) is bonded to the rest of the conjugate;
- R⁸ is hydrogen, a substituted or unsubstituted alkyl or cycloalkyl radical, a substituted or unsubstituted aryl radical, a saturated or unsaturated, optionally substituted heterocyclic radical, an optionally substituted alkenyl radical, an optionally substituted alkinyl radical, a hydroxyl radical or an alkoxy radical or is bonded to $R^9$ with formation of an optionally substi-tuted carbocyclic or heterocyclic ring system which includes the carbon atom to which $R^8$ is bonded and can optionally contain heteroatoms;

$R^9$ is hydrogen, a substituted or unsubstituted alkyl or cycloalkyl radical, a substituted or unsubstituted aryl radical, a saturated or unsaturated, optionally substituted heterocyclic radical, an optionally substituted alkenyl radical, an optionally substituted alkinyl radical, a hydroxyl radical or an alkoxy radical or is bonded to $R^8$ with formation of an optionally substi-tuted carbocyclic or heterocyclic ring system which includes the carbon atom to which $R^9$ is bonded and can optionally contain heteroatoms;

$R^{10}$ is $—SO_2R^{10'}$, $—COOR^{10''}$, $—COR^{10'}$, $—CONR^{10'}_2$ or $—CS—NR^{10'}_2$, or represents a direct bond via which the radical of the formula (III) is optionally bonded to the rest of the conjugate;

$R^{10'}$ independently of one another is hydrogen, a substituted or unsubstituted alkyl or cycloalkyl radical, a substituted or unsubstituted aryl radical or a saturated or unsaturated, optionally substituted heterocyclic radical, via which the radical of the formula (III) is optionally bonded to the rest of the conjugate;

$R^{10''}$ is a substituted or unsubstituted alkyl or cycloalkyl radical, a substituted or unsubstituted aryl radical or a saturated or unsaturated, optionally substituted heterocyclic radical, via which the radical of the formula (III) is optionally bonded to the rest of the conjugate;

$R^{11}$ is hydrogen, a substituted or unsubstituted alkyl or cycloalkyl radical or a substituted or unsubstituted aryl radical, $R^{16}$ is hydrogen, CN, a substituted or unsubstituted alkyl or cycloalkyl radical, a substituted or unsubstituted alkoxy radical or a halogen atom;

$R^{17}$ is hydrogen, CN, a substituted or unsubstituted alkyl or cycloalkyl radical, a substituted or unsubstituted alkoxy radical or a halogen atom;

L is $—(CH_2)_nNHSO_2(CH_2)_o—$, $—(CH_2)_nSO_2NH(CH_2)_o—$, $—(CH_2)_nNH—CO(CH_2)_o—$, $—(CH_2)_nCONH(CH_2)_o—$, $—(CH_2)_nOCH_2(CH_2)_o—$, $—(CH_2)_nCH_2O(CH_2)_o—$, $—(CH_2)_nCOO(CH_2)_o—$, $—(CH_2)_nOOC—(CH_2)_o—$, $—(CH_2)_nCH_2CO(CH_2)_n—$, $—(CH_2)_nCOCH_2(CH_2)_o—$, $—NHCONH—$, $—(CH_2)_n SCH_2(CH_2)_o—$, $—(CH_2)_nCH_2S(CH_2)_o—$, $—(CH_2)_n CH_2SO(CH_2)_n—$, $—(CH_2)_nSOCH_2(CH_2)_o—$, $—(CH_2)_n CH_2—SO_2(CH_2)_o—$ or $—(CH_2)_n SO_2CH_2(CH_2)_o—$, where n and o each is an integer of 0 or 1 and $n+o \leq 1$;

$R^{12}$ is hydrogen, a substituted or unsubstituted alkyl or cycloalkyl radical, a substituted or unsubstituted aryl radical, a saturated or unsaturated, optionally substituted heterocyclic radical or is bonded to one of $R^{13}$, $R^{14}$ or $R^{15}$, if present, with formation of an optionally substituted heterocyclic ring system which includes the nitrogen atom, to which $R^{12}$ is bonded and can be saturated or unsaturated and/or can contain further heteroatoms;

X' is N, O or S;

p is 0 or 1;

$R^{13}$ is absent, is —H, a substituted or unsubstituted alkyl or cycloalkyl radical, $—NO_2$, $—CN$, $—COR^{13'}$, $—COOR^{13'}$, or is bonded to one of $R^{12}$, $R^{14}$ or $R^{15}$ with formation of an optionally substituted heterocyclic ring system which includes X' and can be saturated or unsaturated and/or can contain further heteroatoms;

$R^{13'}$ is hydrogen, a substituted or unsubstituted alkyl or cycloalkyl radical, a substituted or unsubstituted aryl radical or a saturated or unsaturated, optionally substituted heterocyclic radical which can be saturated or unsaturated and/or can contain further heteroatoms;

Y' is N or S;

$R^{14}$ is absent, hydrogen, a substituted or unsubstituted alkyl or cycloalkyl radical, a substituted or unsubstituted aryl radical, a saturated or unsaturated, optionally substituted heterocyclic radical or is bonded to one of $R^{12}$, $R^{13}$ or $R^{15}$, if present, with formation of an optionally substituted heterocyclic ring system which includes the nitrogen atom to which $R^{14}$ is bonded and can be saturated or unsaturated and/or can contain further heteroatoms;

$R^{15}$ is hydrogen, a substituted or unsubstituted alkyl or cycloalkyl radical, a substituted or unsubstituted aryl radical, a saturated or unsaturated, optionally substituted heterocyclic radical or is bonded to one of $R^{12}$, $R^{13}$ or $R^{14}$, if present, with formation of an optionally substituted heterocyclic ring system which includes the nitrogen atom to which $R^{15}$ is bonded and can be saturated or unsaturated and/or can contain further heteroatoms, or optionally represents a direct bond via which the radical of the formula (III) is bonded to the rest of the conjugate;

or

C) a radical of the formula (IV)

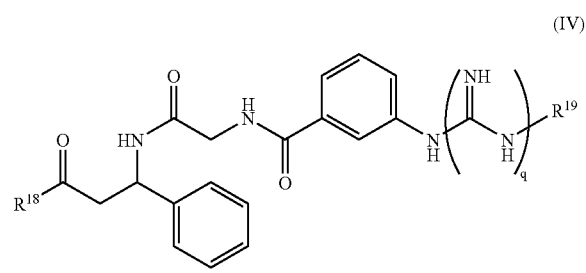

(IV)

in which $R^{18}$ is OH, a substituted or unsubstituted alkoxy or cycloalkoxy radical, a substituted or unsubstituted aryloxy radical or a saturated or unsaturated, optionally substituted heterocyclyloxy radical, or optionally represents a direct bond or an atom from the group consisting of N, O and S, via which the radical of the formula (IV) is bonded to the rest of the conjugate;

q is 0 or 1;

$R^{19}$ is hydrogen, a substituted or unsubstituted alkyl or cycloalkyl radical, a substituted or unsubstituted aryl radical, a saturated or unsaturated, optionally substituted heterocyclic radical, an alkylamine radical, an alkylamide radical, or optionally represents a direct bond, via which the radical of the formula (IV) is bonded to the rest of the conjugate;

and their physiologically acceptable salts and stereoisomers.

Of the conjugates of the formula (I), according to a preferred embodiment those conjugates are particularly preferred in which CT is camptothecin or 9-aminocamptothecin, which can be bonded to the rest of the conjugate via the C20—OH group or, in the case of 9-aminocamptothecin, via the free amino group;

AA1 is absent or is a naturally occurring amino acid in the D or L configuration, which is selected from the group consisting of glycine, alanine, valine, leucine, isoleucine and phenylalanine;

AA2 is absent or is a naturally occurring amino acid in the D or L configuration, which is selected from the group consisting of lysine, glutamate, histidine, glycine, arginine, ornithine and leucine, and can optionally carry protective groups or a radical Sp';

AA3 is absent or is a naturally occurring amino acid in the D or L configuration, which is selected from the group consisting of glycine, alanine, valine, leucine, isoleucine and phenylalanine;

AA4 is absent or is a naturally occurring amino acid in the D or L configuration, which can optionally carry protective groups or a radical Sp', in which Sp' is a phenylaminocarbonyl or a phenylaminothiocarbonyl radical, Sp is absent, is a phenylaminocarbonyl or a phenylaminothiocarbonyl radical or is an alkanedicarboxylic acid radical having 3 to 6 carbon atoms or is a carbonyl or a thiocarbonyl radical, with the proviso that at least one of the radicals AA1 to AA4 and/or Sp is present, IA denotes a non-peptide radical of the formula (II) addressing an $\alpha_v\beta_3$ integrin receptor, in which $R_1$ is OH, methoxy, ethoxy, propoxy, isopropoxy, butoxy, isobutoxy, t-butoxy, pentoxy, isopentoxy, neopentoxy, hexoxy, cyclopropoxy, cyclopropylmethoxy, cyclobutoxy, cyclopentoxy, cyclohexoxy, phenoxy, benzyloxy, tolyloxy or a substituted derivative thereof, or optionally represents a direct bond or an atom from the group consisting of N, O and S, via which the radical of the formula (II) is bonded to the rest of the conjugate;

$R^2$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, an optionally substituted alkenyl radical or an optionally substituted alkinyl radical, via which the radical of the formula (II) is optionally bonded to the rest of the conjugate, or is $-NR^{2'}_2$, $-NR^{2'}SO_2R^{2''}$, $-NR^{2'}COOR^{2''}$, $-NR^{2'}COR^{2'}$, $-NR^{2'}CONR^{2'}_2$ or $-NR^{2'}CSNR^{2'}_2$, in which $R^{2'}$ independently of one another is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, or optionally represents a direct bond via which the radical of the formula (II) is bonded to the rest of the conjugate;

$R^{2''}$ is methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof, $-C_6H_2(CH_3)_3$, 3-aminophenyl, 4-aminophenyl, 2-chlorophenyl, 4-chlorophenyl, 4-methoxyphenyl, 2,5-dichlorophenyl, 4-trifluoromethylphenyl, camphor-10-yl, 4-t-butylphenyl, 2,5-dimethylphenyl, 3-chlorophenyl, 2-methoxy-5-methylphenyl, 2,3,5,6-tetramethylphenyl, 2,3-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline or 8-quinolinyl, via which the radical of the formula (II) is optionally bonded to the rest of the conjugate;

U is a direct bond,

V is an optionally substituted $C_{1-5}$-alkylene group, via which the radical of the formula (II) is optionally bonded to the rest of the conjugate;

A is a 1,3- or 1,4-bridged phenylene group which is unsubstituted or contains at least one alkoxy radical;

B is a 1,3- or 1,4-bridged phenylene group which is unsubstituted or contains at least one alkyl radical;

W is a direct bond or an optionally substituted $C_{1-4}$-alkylene group;

C is a direct bond or

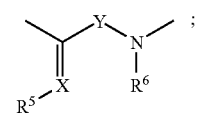

$R^3$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methylcyclohexyl, 3,3,5-trimethylcyclohexyl, 5-methyl-2-hexyl, phenyl, benzyl, tolyl or a substituted derivative thereof, $C_{1-4}$-alkyl-amino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl,

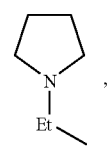 (a1)

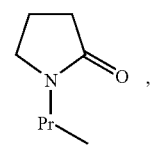 (a2)

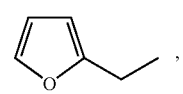 (a3)

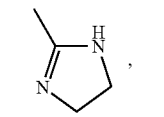 (a4)

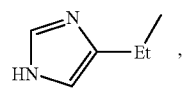 (a5)

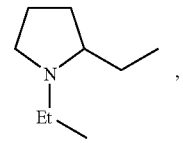 (a6)

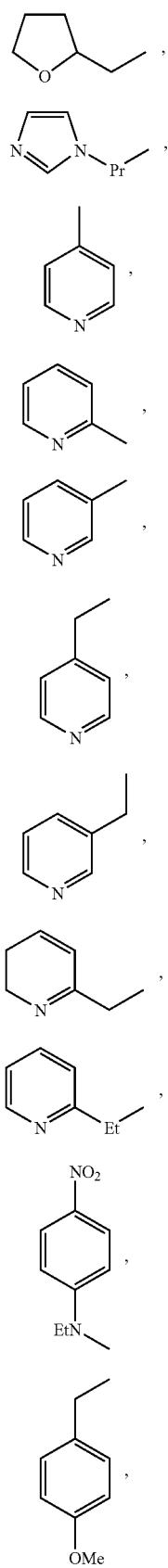
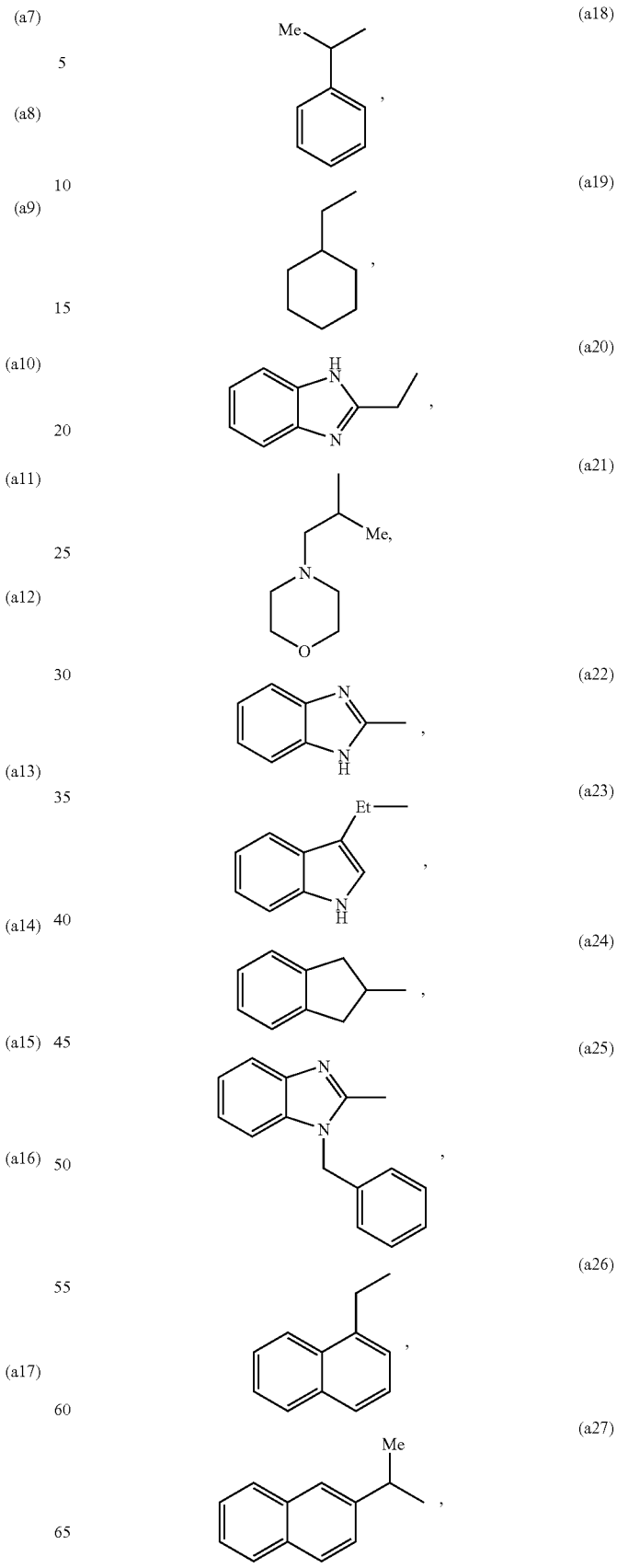

-continued

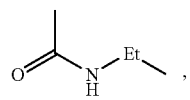
(a28)

or is bonded to one of $R^4$, Y, $R^5$ or $R^6$, if present, with formation of an optionally substituted heterocyclic 4- to 6-membered ring system, which includes the nitrogen atom to which $R^3$ is bonded and can be saturated or unsaturated and/or can contain further heteroatoms;

$R^4$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methylcyclohexyl, 3,3,5-trimeth-ylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the radicals (a1) to (a28) or is bonded to one of $R^3$, Y, $R^5$ or $R^6$, if present, with formation of an optionally substituted heterocyclic 4- to 6-membered ring system which includes the nitrogen atom to which $R^4$ is bonded and can be saturated or unsaturated and/or can contain further heteroatoms, or optionally represents a direct bond via which the radical of the formula (II) is bonded to the rest of the conjugate;

X is O, N or S;

Y is a direct bond or a substituted or unsubstituted methylene or methine group;

$R^5$ is absent, is —$NO_2$, —CN, —$COR^{5'}$, —$COOR^{5'}$ or is bonded to one of $R^3$, Y, $R^4$ or $R^6$, if present, with formation of an optionally substituted carbocyclic or heterocyclic 4- to 6-membered ring system which includes X and which can be saturated or unsaturated and/or can contain further heteroatoms;

$R^{5'}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, tolyl or a substituted derivative thereof;

$R^6$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methylcyclohexyl, 3,3,5-trimeth-yl-cyclohexyl, 5-methyl-2-hexyl, phenyl, benzyl, tolyl or a substituted derivative thereof, $C_{1-4}$-alkyl-amino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the radicals (a1) to (a28) or is bonded to one of $R^3$, Y, $R^4$ or $R^5$, if present, with formation of an optionally substituted heterocyclic 4- to 6-membered ring system which includes the nitrogen atom to which $R^6$ is bonded and can be saturated or unsaturated and/or can contain further heteroatoms.

Particularly preferred conjugates of the formula (I) in this preferred embodiment are those in which $R^1$ represents a direct bond or an atom from the group consisting of N, O and S, via which the radical of the formula (II) is bonded to the rest of the conjugate, and the other radicals of the formula (II) are as defined above.

Likewise, particularly preferred conjugates of the formula (I) in this preferred embodiment are those in which $R^4$ represents a direct bond, via which the radical of the formula (II) is bonded to the rest of the conjugate, and the other radicals of the formula (II) are as defined above.

Likewise, particularly preferred conjugates of the formula (I) in this preferred embodiment are those in which the radical of the formula (II) is linked to the rest of the conjugate via a radical in the α- or β-position relative to the carboxyl group, and the other radicals of the formula (II) are as defined above.

Of the conjugates of the formula (I), according to a further preferred embodiment those conjugates are particularly preferred in which CT is camptothecin or 9-aminocamptothecin, which can be linked to the rest of the conjugate via the $C_{20}$—OH group or, in the case of 9-aminocamptothecin, via the free amino group;

AA1 is absent or is a naturally occurring amino acid in the D or L configuration, which is selected from the group consisting of glycine, alanine, valine, leucine, isoleucine and phenylalanine;

AA2 is absent or is a naturally occurring amino acid in the D or L configuration, which is selected from the group consisting of lysine, glutamate, histidine, glycine, arginine, ornithine and leucine, and can optionally carry protective groups or a radical Sp', AA3 is absent or is a naturally occurring amino acid in the D or L configuration, which is selected from the group consisting of glycine, alanine, valine, leucine, isoleucine and phenylalanine;

AA4 is absent or is a naturally occurring amino acid in the D or L configuration, which can optionally carry protective groups or a radical Sp', in which Sp' is a phenylaminocarbonyl or a phenylaminothiocarbonyl radical, Sp is absent, is a phenylaminocarbonyl or a phenylaminothiocarbonyl radical or an alkanedicarboxylic acid radical having 3 to 6 carbon atoms or a carbonyl or a thiocarbonyl radical, with the proviso that at least one of the radicals AA1 to AA4 and/or Sp is present, IA is a non-peptide radical of the formula (II) addressing an $α_vβ_3$ integrin receptor, in which $R^1$ is OH, methoxy, ethoxy, propoxy, isopropoxy, butoxy, isobutoxy, t-butoxy, pentoxy, isopentoxy, neopentoxy, hexoxy, cyclopropoxy, cyclopropylmethoxy, cyclobutoxy, cyclopentoxy, cyclohexoxy, phenoxy, benzyloxy, tolyloxy or a substituted derivative thereof, or optionally represents a direct bond or an atom from the group consisting of N, O and S, via which the radical of the formula (II) is bonded to the rest of the conjugate;

$R^2$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, phenyl, benzyl, 4-aminobenzyl, tolyl, phenylethyl, a substituted derivative such as 4-aminobenzyl or a saturated or unsaturated, optionally substituted heterocyclic analogue thereof, an optionally substituted alkenyl radical, an optionally substituted alkinyl radical, via which the radical of the formula (II) is optionally bonded to the rest of the conjugate;

U is a direct bond or an optionally substituted $C_{1-3}$-alkylene group such as —$CH(C_6H_4$-3-NH)— or —CH(C₆H₄-4-NH)—, via which the radical of the formula (II) is optionally bonded to the rest of the conjugate;

V is —NR²⁰CO— or —NR²⁰SO₂—;

R²⁰ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, phenyl, benzyl, tolyl, phenylethyl, phenylpropyl, phenoxyethyl or a substituted derivative thereof;

A is a 1,3- or 1,4-bridged phenylene group which is unsubstituted or contains at least one alkoxy radical;

B is a 1,3- or 1,4-bridged phenylene group which is unsubstituted or contains at least one alkyl radical;

W is a direct bond or an optionally substituted $C_{1-3}$-alkylene group;

C

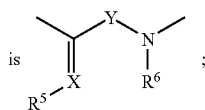

is

R³ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methylcyclohexyl, 3,3,5-trimethyl-cyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the radicals (a1) to (a28) or is bonded to one of R⁴, Y or R⁶, if present, with formation of an optionally substituted heterocyclic 4- to 6-membered ring system, which includes the nitrogen atom to which R³ is bonded, and can be saturated or unsaturated and/or can contain further heteroatoms;

R⁴ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methylcyclohexyl, 3,3,5-trimethyl-cyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the radicals (a1) to (a28) or is bonded to one of R³, Y or R⁶, if present, with formation of an optionally substituted heterocyclic 4- to 6-membered ring system, which includes the nitrogen atom to which R⁴ is bonded and can be saturated or unsaturated and/or can contain further heteroatoms, or optionally represents a direct bond via which the radical of the formula (II) is bonded to the rest of the conjugate;

X is O or S;

Y is a direct bond or a substituted or unsubstituted methylene or methine group;

R⁵ is absent;

R⁶ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methylcyclohexyl, 3,3,5-trimeth-yl-cyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the radicals (a1) to (a28) or is bonded to one of R³, Y or R⁴, if present, with formation of an optionally substituted heterocyclic 4- to 6-membered ring system which includes the nitrogen atom to which R⁶ is bonded, and can be saturated or unsaturated and/or can contain further heteroatoms.

Particularly preferred conjugates of the formula (I) in this further preferred embodiment are those in which R¹ represents a direct bond or an atom from the group consisting of N, O and S, via which the radical of the formula (II) is bonded to the rest of the conjugate, and the other radicals of the formula (II) are as defined above.

Likewise, particularly preferred conjugates of the formula (I) in this further preferred embodiment are those in which R⁴ represents a direct bond, via which the radical of the formula (II) is bonded to the rest of the conjugate, and the other radicals of the formula (II) are as defined above.

Likewise, particularly preferred conjugates of the formula (I) in this further preferred embodiment are those in which the radical of the formula (II) is linked to the rest of the conjugate via a radical in the α- or β-position relative to the carboxyl group, and the other radicals of the formula (II) are as defined above.

Of the conjugates of the formula (I), according to yet a further preferred embodiment those conjugates are particularly preferred in which CT is camptothecin or 9-aminocamptothecin, which can be linked to the rest of the conjugate via the C20—OH group or, in the case of 9-aminocamptothecin, via the free amino group;

AA1 is absent or is a naturally occurring amino acid in the D or L configuration, which is selected from the group consisting of glycine, alanine, valine, leucine, isoleucine and phenylalanine;

AA2 is absent or is a naturally occurring amino acid in the D or L configuration, which is selected from the group consisting of lysine, glutamate, histidine, glycine, arginine, ornithine and leucine, and can optionally carry protective groups or a radical Sp', AA3 is absent or is a naturally occurring amino acid in the D or L configuration, which is selected from the group consisting of glycine, alanine, valine, leucine, isoleucine and phenylalanine;

AA4 is absent or is a naturally occurring amino acid in the D or L configuration, which can optionally carry protective groups or a radical Sp', in which Sp' is a phenylaminocarbonyl or a phenylaminothiocarbonyl radical, Sp is absent, is a phenylaminocarbonyl or a phenylaminothiocarbonyl radical or is an alkanedicarboxylic acid radical having 3 to 6 carbon atoms or a carbonyl or a thiocarbonyl radical, with the proviso that at least one of the radicals AA1 to AA4 and/or Sp is present, IA is a non-peptide radical of the formula (III) addressing an $\alpha_v\beta_3$ integrin receptor, in which R⁷ is OH, methoxy, ethoxy, propoxy, isopropoxy, butoxy, isobutoxy, t-butoxy, pentoxy, isopentoxy, neopentoxy, hexoxy, cyclopropoxy, cyclopropylmethoxy, cyclobutoxy, cyclopentoxy, cyclohexoxy, phenoxy, benzyloxy, tolyloxy or a substituted derivative thereof, or optionally represents a direct bond or an atom from the group consisting of N, O and S, via which the radical of the formula (III) is bonded to the rest of the conjugate;

R⁸ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —OH, methoxy, ethoxy, propoxy, butoxy, pentoxy, hexoxy, benzyloxy or is bonded to R⁹ with formation of an optionally substituted 3- to 6-membered carbocyclic or heterocyclic ring system, which includes the carbon atom to which R⁸ is bonded and can optionally contain heteroatoms;

R⁹ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —OH, methoxy, ethoxy, propoxy, butoxy, pentoxy, hexoxy or is bonded to R⁸ with formation of an optionally substituted 3- to 6-membered carbocyclic or heterocyclic ring system which includes the carbon atom to which R⁹ is bonded and can optionally contain heteroatoms;

R¹⁰ is SO₂R¹⁰', —COOR¹⁰'', —COR¹⁰', —CONR¹⁰'₂ or —CS—NR¹⁰'₂ or represents a direct bond, via which the radical of the formula (III) is optionally bonded to the rest of the conjugate;

R¹⁰' is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —C₆H₂(CH₃)₃, —C₆(CH₃)₅, —CH₂C₆H₂(CH₃)₃, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 3-aminophenyl, 4-aminophenyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methylthiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimeth-oxy-phenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methylbenzothiazol-2-yl, N-methoxycarbonyl-piperidin-3-yl, thiophen-2-yl, isoxazol-5-yl, ethoxy, 2-chloropyridin-3-yl, pyridin-3-yl, benzyloxy, 5-methylisoxazol-3-yl, 1-adamantyl, 4-chlorophenoxymethyl, 2,2-dimethyl-ethenyl, 2-chloropyridine-5-methyl, 5,7-dimethyl-1,3,4-triazaindolizin-2-yl, (S)-camphan-1-yl, (R)-camphan-1-yl or 8-quinolinyl;

R¹⁰'' is a C₁₋₆-alkyl radical, a C₃₋₇-cycloalkyl radical, a substituted or unsubstituted aryl radical or a saturated or unsaturated, optionally substituted heterocyclic radical, via which the radical of the formula (III) is optionally bonded to the rest of the conjugate;

R¹¹ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, phenyl, benzyl, tolyl or a substituted derivative thereof, C₁₋₄-alkylamino-C₁₋₄-alkyl, C₁₋₄-dialkylamino-C₁₋₄-alkyl, amino-C₁₋₄-alkyl, C₁₋₄-alkyloxy-C₁₋₄-alkyl, dialkylamino-C₁₋₄-alkyl, amino-C₁₋₄-alkyl, C₁₋₄-alkyloxy-C₁₋₄-alkyl or

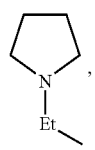 (a1)

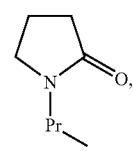 (a2)

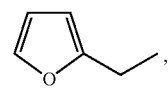 (a3)

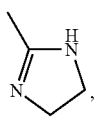 (a4)

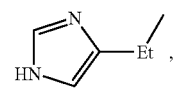 (a5)

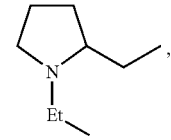 (a6)

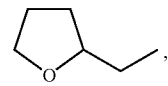 (a7)

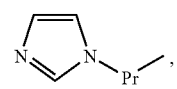 (a8)

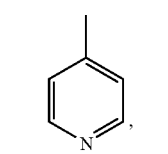 (a9)

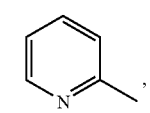 (a10)

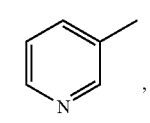 (a11)

-continued (a12) (structure: 4-ethylpyridine)

(a13) (structure: 3-ethylpyridine)

(a14) (structure: 2-ethylpyridine)

(a15) (structure: 2-pyridyl-CH(Et))

(a16) (structure: 4-nitro-N-ethylaniline derivative)

(a17) (structure: 4-methoxyphenethyl)

(a18) (structure: 1-phenylethyl)

(a19) (structure: ethylcyclohexyl)

(a20) (structure: 2-ethylbenzimidazole)

-continued (a21) (structure: N-isobutyl morpholine)

(a22) (structure: 2-methylbenzimidazole)

(a23) (structure: 3-ethylindole)

(a24) (structure: 2-methylindane)

(a25) (structure: 1-benzyl-2-methylbenzimidazole)

(a26) (structure: 1-ethylnaphthalene)

(a27) (structure: 2-(1-methylethyl)naphthalene)

(a28) (structure: N-ethylacetamide)

$R^{16}$ is hydrogen, CN, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, methoxy, trifluoromethoxy, ethoxy, propoxy, butoxy, pentoxy or hexoxy, fluorine, chlorine, bromine or iodine;

$R^{17}$ is hydrogen, CN, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, methoxy, ethoxy, trifluoromethoxy, propoxy, butoxy, pentoxy or hexoxy, fluorine, chlorine, bromine or iodine;

L is —NHSO$_2$—, —CH$_2$NHSO$_2$—, —NHSO$_2$CH$_2$—, —SO$_2$NH—, —CH$_2$SO$_2$NH—, —SO$_2$NHCH$_2$—, —NHCO—, —CH$_2$NHCO—, —NHCOCH$_2$—, —CONH—, —CH$_2$CONH—, —CONHCH$_2$—, —OCH$_2$—, —CH$_2$OCH$_2$, —OCH$_2$CH$_2$—, —CH$_2$O— or —CH$_2$CH$_2$O—;

$R^{12}$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, cycloheptyl, 4-methylcyclohexyl, 3,3,5-tmmethylcyclohexyl, 5-methyl-2-hexyl, phenyl, benzyl, tolyl or a substituted derivative thereof, $C_{1-4}$-alkylamino-$C_{1-4}$-alky, $C_{1-4}$-dialkylamino-$C_{1-4}$-alkyl, amino-$C_{1-4}$-alkyl, $C_{1-4}$-alkyloxy-$C_{1-4}$-alkyl, one of the radicals (a1) to (a28) or is bonded to one of $R^{13}$, $R^{14}$ or $R^{15}$, if present, with formation of an optionally substituted heterocyclic 4- to 6-membered ring system which includes the nitrogen atom to which $R^{12}$ is bonded and can be saturated or unsaturated and/or can contain further heteroatoms;

X' is N, O or S;

p is 0 or 1;

$R^{13}$ is absent, is —H, methyl, ethyl, propyl, isopropyl, butyl, isobutyl, t-butyl, pentyl, isopentyl, neopentyl, hexyl, cyclopropyopyl, cyclobutyl, cyclopentyl, cyclohexyl, cycloheptyl, —NO$_2$, —CN, —COR$^{7\prime}$, —COOR$^{7\prime\prime}$, or is connected to one of $R^{12}$, $R^{14}$ or $R^{15}$ with formation of an optionally substituted carbocyclic or heterocyclic 4- to 6-membered ring system which includes X' and can be saturated or unsaturated and/or can contain further heteroatoms;

$R^{13\prime}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof;

Y' is N or S;

$R^{14}$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the radicals (a1) to (a28), or is connected to one of $R^{12}$, $R^{13}$ or $R^{15}$, if present, with formation of an optionally substituted heterocyclic 4- to 6-membered ring system which includes the nitrogen atom to which $R^{14}$ is bonded and can be saturated or unsaturated and/or can contain further hetero atoms; and $R^{15}$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, cycloheptyl, 4-methylcyclohexyl, 3,3,5-trimeth-ylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the radicals (a1) to (a28), or is bonded to one of $R^{12}$, $R^{13}$ or $R^{14}$, if present, with formation of an optionally substituted heterocyclic 4- to 6-membered ring system which includes the nitrogen atom to which $R^{15}$ is bonded and can be saturated or unsaturated and/or can contain further heteroatoms, and or optionally represents a direct bond via which the radical of the formula (III) is bonded to the rest of the conjugate.

Particularly preferred conjugates of the formula (I) in this further preferred embodiment are those in which $R^7$ represents a direct bond or an atom from the group consisting of N, O and S, via which the radical of the formula (III) is bonded to the rest of the conjugate, and the other radicals of the formula (III) are as defined above.

Likewise, particularly preferred conjugates of the formula (I) in this further preferred embodiment are those in which $R^{15}$ represents a direct bond, via which the radical of the formula (III) is bonded to the rest of the conjugate, and the other radicals of the formula (III) are as defined above.

Likewise particularly preferred conjugates of the formula (I) in this further preferred embodiment are those in which the radical of the formula (III) is linked to the rest of the conjugate via a radical in the α- or β-position relative to the carboxyl group, and the other radicals of the formula (III) are as defined above.

According to a further preferred embodiment, conjugates of the formula (I) are preferred in which $R^{18}$ represents a direct bond or an atom from the group consisting of N, O and S, via which the radical of the formula (IV) is bonded to the rest of the conjugate, and the other radicals of the formula (IV) are as defined above.

Likewise particularly preferred conjugates of the formula (I) in this further preferred embodiment are those in which $R^{19}$ represents a direct bond, via which the radical of the formula (IV) is bonded to the rest of the conjugate, and the other radicals of the formula (IV) are as defined above.

The compounds of the formula (I) according to the invention can also be present in the form of their salts. In general salts with organic or inorganic bases or acids may be mentioned here.

In particular, the compounds of the formula (I) according to the invention can be employed in the form of their physiologically acceptable salts. Physiologically acceptable salts are understood according to the invention as meaning non-toxic salts which in general are accessible by reaction of the compounds of the formula (I) according to the invention with an inorganic or organic base or acid conventionally used for this purpose. Examples of preferred salts of the compounds of the formula (I) according to the invention are the corresponding alkali metal salt, e.g. lithium, potassium or sodium salt, the corresponding alkaline earth metal salt such as the magnesium or calcium salt, a quaternary ammonium salt such as, for example, the triethylammonium salt, acetate, benzenesulphonate, benzoate, dicarbonate, disulphate, ditartrate, borate, bromide, carbonate, chloride, citrate, dihydrochloride, fumarate, gluconate, glutamate, hexylresorcinate, hydrobromide, hydrochloride, hydroxynaphthoate, iodide, isethionate, lactate, laurate, malate, maleate, mandelate, mesylate, methylbromide, methylnitrate, methylsulphate, nitrate, oleate, oxalate, palmitate, pantothenate, phosphate, diphosphate, polygalacturonate, salicylate, stearate, sulphate, succinate, tartrate, tosylate and valerate and other salts used for medicinal purposes.

The present invention includes both the individual enantiomers or diastereomers and the corresponding racemates, diastereomer mixtures and salts of the compounds according to the invention. In addition, all possible tautomeric forms of the compounds described above are included according to the present invention. Furthermore, the present invention includes both the pure E and Z isomers of the compounds of the formula (I) and their E/Z mixtures in all ratios. The diastereomer mixtures or E/Z mixtures can be separated into the individual isomers by chromatographic processes. The racemates can be resolved into the respective enantiomers either by chromatographic processes on chiral phases or by resolution.

In the context of the present invention, the substituents, if not stated otherwise, in general have the following meaning:

Alkyl in general represents a straight-chain or branched hydrocarbon radical having 1 to 20 carbon atoms. Examples which may be mentioned are methyl, ethyl, propyl, isopropyl, butyl, isobutyl, pentyl, isopentyl, hexyl, isohexyl, heptyl, isoheptyl, octyl and isooctyl, nonyl, decyl, dodeyl, eicosyl.

Alkenyl in general represents a straight-chain or branched hydrocarbon radical having 2 to 20 carbon atoms and one or more, preferably having one or two, double bonds. Examples which may be mentioned are allyl, propenyl, isopropenyl, butenyl, isobutenyl, pentenyl, isopentenyl, hexenyl, isohexenyl, heptenyl, isoheptenyl, octenyl, isooctenyl.

Alkinyl in general represents a straight-chain or branched hydrocarbon radical having 2 to 20 carbon atoms and one or more, preferably having one or two, triple bonds. Examples which may be mentioned are ethinyl, 2-butinyl, 2-pentinyl and 2-hexinyl.

Acyl in general represents straight-chain or branched lower alkyl having 1 to 9 carbon atoms, which is bonded via a carbonyl group. Examples which may be mentioned are: acetyl, ethylcarbonyl, propylcarbonyl, isopropylcarbonyl, butylcarbonyl and isobutylcarbonyl.

Alkoxy in general represents a straight-chain or branched hydrocarbon radical having 1 to 14 carbon atoms and bonded via an oxygen atom. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy, The terms "alkoxy" and "alkyloxy" are used synonymously.

Alkoxyalkyl in general represents an alkyl radical having up to 8 carbon atoms, which is substituted by an alkoxy radical having up to 8 carbon atoms.

Alkoxycarbonyl can be represented, for example, by the formula

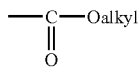

Alkyl here in general represents a straight-chain or branched hydrocarbon radical having 1 to 13 carbon atoms. Examples which may be mentioned are the following alkoxycarbonyl radicals: methoxycarbonyl, ethoxycarbonyl, propoxycarbonyl, isopropoxycarbonyl, butoxycarbonyl or isobutoxycarbonyl.

Cycloalkyl in general represents a cyclic hydrocarbon radical having 3 to 8 carbon atoms. Cyclopropyl, cyclopentyl and cyclohexyl are preferred. Examples which may be mentioned are cyclopentyl, cyclohexyl, cycloheptyl and cyclooctyl.

Cycloalkoxy in the context of the invention represents an alkoxy radical whose hydrocarbon radical is a cycloalkyl radical. The cycloalkyl radical in general has up to 8 carbon atoms. Examples which may be mentioned are: cyclopropyloxy and cyclohexyloxy. The terms "cycloalkoxy" and "cycloalkyloxy" are used synonymously.

Aryl in general represents an aromatic radical having 6 to 10 carbon atoms. Preferred aryl radicals are phenyl, benzyl and naphthyl.

Halogen in the context of the invention represents fluorine, chlorine, bromine and iodine.

Heterocycle in the context of the invention in general represents a saturated, unsaturated or aromatic 3- to 10-membered, for example 5- or 6-membered, heterocycle which can contain up to 3 heteroatoms from the group consisting of S, N and/or 0 and which, in the case of a nitrogen atom, can also be bonded via this. Examples which may be mentioned are: oxadiazolyl, thiadiazolyl, pyrazolyl, pyridyl, pyrimidinyl, pyridazinyl, pyrazinyl, thienyl, furyl, pyrrolyl, pyrrolidinyl, piperazinyl, tetrahydropyranyl, tetrahydrofuranyl, 1,2,3-triazolyl, thiazolyl, oxazolyl, imidazolyl, morpholinyl or piperidyl. Thiazolyl, furyl, oxazolyl, pyrazolyl, triazolyl, pyridyl, pyrimidinyl, pyridazinyl and tetrahydropyranyl are preferred. The term "heteroaryl" (or "hetaryl") represents an aromatic heterocyclic radical.

The conjugates according to the invention are characterized in that a cytotoxic radical or a radical of a cytostatic or of a cytostatic derivative is bonded via a linking unit to a non-peptide moiety addressing $\alpha_v\beta_3$ or $\alpha_v\beta_5$ integrin receptors.

The non-peptide moiety of the conjugate addressing $\alpha_v\beta_3$ or $\alpha_v\beta_5$ integrin receptors serves to bring the toxophoric part of the conjugate into or into the vicinity of tumour cells and thus to achieve tissue selectivity. Growing tumour tissue stimulates the formation of new blood vessels, i.e. angiogenesis, to a considerable extent in order to cover its increasing nutritional need. The blood vessels newly formed by angiogenesis differ from conventional tissue by specific markers on the surfaces of the endothelial cells formed. Moreover, the $\alpha_v\beta_3$ or $\alpha_v\beta_5$ integrin receptor is expressed by many human tumours (cf. WO 98/10795 and the references indicated there). Thus the conjugate is brought selectively into or into the vicinity of the tumour tissue to be treated by the interaction of its non-peptide part addressing $\alpha_v\beta_3$ or $\alpha_v\beta_5$ integrin receptors with $\alpha_v\beta_3$ or $\alpha_v\beta_3$ integrin receptors found on endothelial cells or on tumour cells formed by angiogenesis.

Unlike peptide radicals addressing $\alpha_v\beta_3$ or $\alpha_v\beta_5$ integrin receptors (such as disclosed, for example, in WO 98/10795), the non-peptide moieties according to the invention addressing $\alpha_v\beta_3$ or $\alpha_v\beta_5$ integrin receptors are distinguished by an increased serum stability, whereby the transport of the toxophore in the conjugate to the tumour tissue is ensured to an increased extent.

According to the present invention, non-peptide compounds with antagonistic action against $\alpha_v\beta_3$ or $\alpha_v\beta_5$ integrin receptors are suitable. Examples of compounds of this type which can be mentioned are the compounds described in the following specifications: GB-A-2 271 567, GB-A-2 292 558, EP-A-0 645 376, EP-A-0 668 278, EP-A-0 608 759, EP-A-0 635 492, WO 94/22820, U.S. Pat. No. 5,340, 798, WO 94/09029, U.S. Pat. No. 5,256,812, EP-A-0 381 033, U.S. Pat. No. 5,084,466, WO 94/18981, WO 94/01396, U.S. Pat. No. 5,272,162, WO 94/21602, WO 94//22444, WO 94/29273, WO 95/18111, WO 95/18619, WO 95/25091, WO 94/18162, U.S. Pat. No. 5,220,050, WO 9316038, U.S. Pat. No. 4,879,313, EP-B-0 352 249, WO 93/16697, U.S. Pat. No. 5,227,490, EP-A-0 478 363, U.S. Pat. No. 5,229, 616, WO 94/12181, U.S. Pat. No. 5,258,398, WO 93/11759, WO 93/08181, EP-A-0537980, WO 93/09133, EP-B-0 530 505, EP-A-0 566 919, EP-B-0 540 334, EP-A-0 560 730, WO 93/10091, EP-A-0 542 363, WO 93/14077, EP-B-0 505 868, EP-A-0 614 664, U.S. Pat. No. 5,358,956, U.S. Pat. No.

5,334,596, WO 94/26745, WO 94/12478, WO 94/14776, WO 93/00095, WO 93/18058, WO 93/07867, U.S. Pat. No. 5,239,113, U.S. Pat. No. 5,344,957, EP-A-0 542 708, WO 94/22825, U.S. Pat. No. 5,250,679, WO 93/08174, U.S. Pat. No. 5,084,466, EP-A-0 668 274, U.S. Pat. No. 5,264,420, WO/9408962, EP-A-0 529 858, U.S. Pat. No. 5,389,631, WO 94/08577, EP-A-0 632 016, EP-A-0 503 548, EP-A-0 512 831, WO 92/19595, WO 93/22303, EP-A-0 525 629, EP-A-0 604 800, EP-A-0 587 134, EP-A-0 623 615, EP-A-0 655 439, U.S. Pat. No. 5,466,056, WO 95/14682, U.S. Pat. No. 5,399,585, WO 93/12074, EP-A-0 512 829, EP-A-0 372 486, U.S. Pat. No. 5,039,805, EP-A-0 632 020, U.S. Pat. No. 5,494,922, U.S. Pat. No. 5,403,836, WO 94/22834, WO 94/21599, EP-A-0 478 328, WO 94/17034, WO 96/20192, WO 96/19223, WO 96/19221, WO 96/19222, EP-A-0 727 425, EP-AO 0 478 362, EP-A-0 478 363, U.S. Pat. No. 5,272,158, U.S. Pat. No. 5,227,490, U.S. Pat. No. 5,294,616, U.S. Pat. No. 5,334,596, EP-A-0 645376, EP-A-0 711 770, U.S. Pat. No. 5,314,902, WO 94/00424, U.S. Pat. No. 5,523,302, EP-A-0 718 287, DE-A-4 446 301, WO 96/22288, WO 96/29309, EP-A-0 719 775, EP-A-0 635492, WO 96/16947, U.S. Pat. No. 5,602,155, WO 96/38426, EP-A-0 712 844, U.S. Pat. No. 5,292,756, WO 96/37482, WO 96/38416, WO 96/41803, WO97/11940, WO98/00395, WO 98/18461, WO 94/12181, WO 97/36858, WO 97/36859, WO 97/36860, WO 97/36862, U.S. Pat. No. 5,639,765, WO 97/08145 and WO 97/36861. The contents of these specifications are completely inserted here by way of reference.

The abovementioned compounds having antagonistic action against $\alpha_v\beta_3$ or $\alpha_v\beta_5$ integrin receptors must be able to retain their property of addressing $\alpha_v\beta_3$ or $\alpha_v\beta_{35}$ integrin receptors in the conjugate. This means that these compounds must be linked to a toxophore in such a way that no or only a slight impairment of the abovementioned action of the compounds results thereby. In the normal case, the linkage with the linking unit will take place via a functional group suitable for this in the molecule, for example via an amino, hydroxyl or carboxyl function. If the abovementioned compounds have no functional group, one of these is easily insertable into the molecule by conventional processes known to the person in the art without the loss of the antagonistic action against $\alpha_v\beta_3$ or $\alpha_v\beta_5$ integrin receptors occurring here.

The conjugate according to the invention can release its toxophoric radical at its target site and this can thus make possible penetration into the tumour tissue. This is carried out by the specific choice of a unit linking the toxophoric radical to the moiety addressing $\alpha_v\beta_3$ or $\alpha_v\beta_5$ integrin receptors. In order to be able to release the toxophoric radical, the linking unit must be cleavable under physiological conditions. This means that the linking unit must be cleavable either hydrolytically or by endogenous enzymes.

It is particularly preferred if the linking unit is cleaved by tumour-associated enzymes. This leads to a further increase in the tissue selectivity of the action of the conjugates according to the invention.

A further suitable starting point for promoting the tissue selectivity of the action of the conjugates according to the invention consists in the so-called ADEPT approach. In this, conjugates are cleaved by certain enzymes. These enzymes are introduced into the body coupled to antibodies together with the conjugates according to the invention, the antibodies serving as vehicles specifically addressing tumour tissue. This leads to a selective concentration both of the conjugate and of the enzyme/antibody system in the tumour tissue, whereby the toxophore is released in the tumour tissue with even greater selectivity and can display its action there.

Suitable linking units according to the invention are all linking units which fulfil at least one of the abovementioned criteria and can be linked to the moiety addressing $\alpha_v\beta_3$ or $\alpha_v\beta_5$ integrin receptors in such a way that this retains its binding action to $\alpha_v\beta_3$ or $\alpha_v\beta_5$ integrin receptors.

In the conjugates according to the invention, toxophores used can be all cytotoxic radicals or radicals of a cytostatic or of a cytostatic derivative which are conventionally employed in tumour therapy.

According to a preferred embodiment, conjugates according to the invention which can be employed are compounds of the formula (I) in which a toxophore is linked via a linking unit consisting of 0 to 4 amino acids, preferably 1 to 3 amino acids and particularly preferably 2 amino acids, and, if appropriate, of a non-peptide spacer group, to a non-peptide moiety addressing $\alpha_v\beta_3$ integrin receptors from the group of radicals of the formulae (II) to (IV):

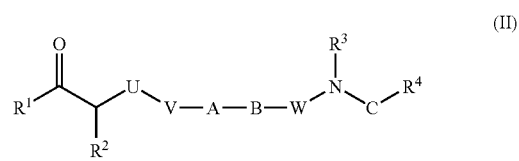

(II)

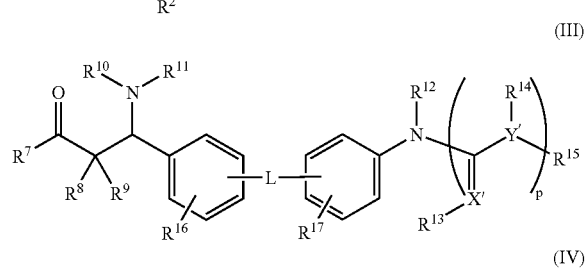

(III)

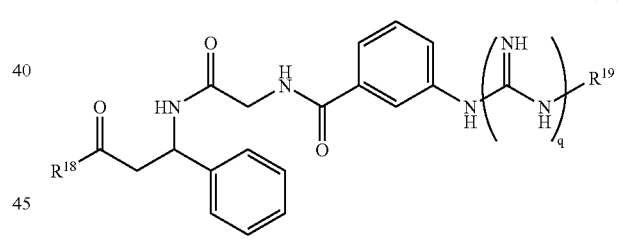

(IV)

where the radicals in the formulae (II) to (IV) have the meanings indicated above.

In the conjugates of the formula (I) according to the invention, the toxophore used can be cytostatic radicals or radicals of a cytostatic or of a cytostatic derivative which are conventionally employed in tumour therapy. Camptothecin or derivatives of camptothecin such as 9-aminocamptothecin are preferred here, which can be linked to the rest of the conjugate via the $C_{20}$—OH group or via a functional group which is optionally present in the molecule, such as the amino group in the case of 9-aminocamptothecin. According to this preferred embodiment, the camptothecin unit used as a starting compound can be present in the 20(R) or in the 20(S) configuration or as a mixture of these two stereoisomeric forms. The 20(S) configuration is preferred.

In the conjugates of the formula (I), the linking unit preferably consists of a unit of the formula -AA1-AA2-AA3-AA4-Spradicals AA1 to AA4, if they are present, each represent an amino acid in the D or L configuration, which can optionally carry protective groups or a radical Sp'. In this context, they are particularly preferably one of the naturally occurring amino acids glycine, alanine, valine, leucine, isoleucine, serine, threonine, cysteine, methionine, aspartate, glutamate, asparagine, glutamine, arginine, lysine, histidine, tryptophan, phenylalanine, tyrosine or proline. The amino acids used in the process according to the invention can occur in the L or in the D configuration or alternatively as a mixture of D and L form.

The term "amino acids" refers, according to the invention, in particular to the α-amino acids occurring in nature, but moreover also includes their homologues, isomers and derivatives. An example of isomers which can be mentioned is enantiomers. Derivatives can be, for example, amino acids provided with protective groups.

According to the present invention, the amino acids can each be linked to one another and to the toxophore or to the moiety addressing $\alpha_v\beta_3$ or $\alpha_v\beta_5$ integrin receptors via their α-carboxyl or α-amino functions, but also via functional groups optionally present in side chains, such as, for example, amino functions.

In the case of amino acids having functional groups in the side chains, these functional groups can be either deblocked or protected by conventional protective groups used in peptide chemistry. Protective groups employed for these functional groups of the amino acids can be the protective groups known in peptide chemistry, for example of the urethane, alkyl, acyl, ester or amide type.

Amino protective groups in the context of the invention are the customary amino protective groups used in peptide chemistry. These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, tert-butoxycarbonyl (Boc), allyloxycarbonyl, vinyloxycarbonyl, 3,4,5-trimethoxybenzyloxycarbonyl, phthaloyl, 2,2,2-trichloroethoxycarbonyl, 2,2,2-trichloro-tert-butoxycarbonyl, menthyloxycarbonyl, 4-nitro-phenoxycarbonyl, fluorenyl-9-methoxycarbonyl (Fmoc), formyl, acetyl, propionyl, pivaloyl, 2-chloroacetyl, 2-bromoacetyl, 2,2,2-trifluoroacetyl, 2,2,2-trichloroacetyl, benzoyl, benzyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl, 4-nitrophenyl or 2-nitrophenylsulphenyl. The Fmoc group and the Boc group are particularly preferred.

The removal of protective groups in appropriate reaction steps can be carried out, for example, by the action of acid or base, hydrogenolytically or reductively in another manner.

Furthermore, each of the amino acids AA1 to AA4 can carry a radical Sp', where Sp' represents an arylaminocarbonyl or an arylaminothiocarbonyl radical having 7–11 carbon atoms. Preferably, this radical Sp' is a phenylaminocarbonyl or a phenylaminothiocarbonyl radical.

The radical Sp' is preferably bonded to the side chain of the corresponding amino acid via the functional group. If, however, the linkage of the toxophore to the moiety addressing $\alpha_v\beta_3$ or $\alpha_v\beta_5$ integrin receptors in an amino acid takes place via the functional group in the side chain, the radical Sp' can also be linked to the carboxyl or α-amino function of the corresponding amino acid.

According to a preferred embodiment, AA1, if present, is selected from amino acids having sterically demanding or non-polar side chains. Examples which may be mentioned are glycine, alanine, valine, leucine, isoleucine, phenylalanine, proline, tryptophan and methionine. Valine, leucine and isoleucine are particularly preferred.

According to a preferred embodiment, AA2, if present, is selected from amino acids having basic side chains. Examples which may be mentioned are lysine, arginine, glutamate, histidine, ornithine, glycine, leucine or diaminobutyric acid. However, amino acids having non-polar side chains can also be used. Lysine, glutamate, histidine, leucine and glycine are particularly preferred.

According to a preferred embodiment, AA3, if present, is selected from amino acids having non-polar side chains. Examples which may be mentioned are glycine, alanine, valine, leucine, phenylalanine and isoleucine. Glycine, valine and leucine are particularly preferred.

According to a preferred embodiment, AA4, if present, is selected from amino acids having non-polar side chains. Examples which may be mentioned are alanine, valine, leucine, isoleucine, proline, tryptophan, phenylalanine and methionine. Alanine, valine and proline are particularly preferred.

According to the preferred embodiment according to the invention, the spacer unit Sp is an arylaminocarbonyl or an arylaminothiocarbonyl radical having 7–11 carbon atoms or an alkanedicarboxylic acid radical having 3 to 8 carbon atoms or a carbonyl or a thiocarbonyl radical. Particularly preferably, Sp is a phenylaminocarbonyl or a phenylaminothiocarbonyl radical or an alkanedicarboxylic acid radical having 3 to 6 carbon atoms or a carbonyl or a thiocarbonyl radical. In particular, a carbonyl or a thiocarbonyl radical and a succinic acid or glutaric acid radical are preferred.

It is preferred according to the invention that the linking unit consists of two amino acids AA1 and AA2 and the spacer unit Sp, it being possible, in particular, for the unit AA2 to be modified on the side chain by protective groups or the radical Sp'. However, it is also possible for the linking unit to consist of one, three or four amino acids AA1 to AA4 and a spacer unit Sp. In these cases, the linkage to the toxophore as a rule takes place via the carboxyl function of the amino acid AA1 and the linkage to the moiety addressing $\alpha_v\beta_3$ or $\alpha_v\beta_5$ integrin receptors via the spacer unit Sp takes place using an amino group or hydroxyl group of the moiety addressing $\alpha_v\beta_3$ or $\alpha_v\beta_5$ integrin receptors.

In the case in which the linkage is to take place via a carboxyl function of the moiety addressing $\alpha_v\beta_3$ or $\alpha_v\beta_3$ integrin receptors, it is preferred, however, to use linking units without the spacer unit Sp. In this case, the linkage between the linking unit and the moiety addressing $\alpha_v\beta_3$ or $\alpha_v\beta_5$ integrin receptors takes place via an amino function of an amino acid. In this case, a linking unit consisting of two amino acids AA1 and AA2 is particularly preferred.

If the toxophore contains an amino function, for example 9-aminocamptothecin, the linkage to the moiety addressing $\alpha_v\beta_3$ or $\alpha_v\beta_5$ integrin receptors can take place directly via a spacer unit Sp without any amino acids AA1 to AA4 being contained in the linking unit. It is particularly preferred in this case for Sp to represent a carbonyl or thiocarbonyl function, in particular a thiocarbonyl function.

The moiety addressing $\alpha_v\beta_3$ integrin receptors can be, for example, a radical of the formula (II):

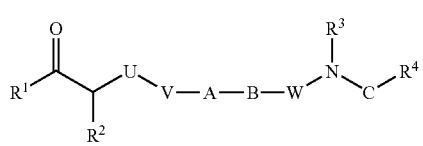

where the radicals in the formula (II) have the meaning defined above.

In the description below, bivalent substituents are indicated such that their respective left end is connected to the group indicated left of the corresponding substituent in formula (II) and their respective right end is connected to the group indicated right of the corresponding substituent in formula (II). If, for example, in formula (II) the radical V is equal to —$NR^{20}SO_2$—, the nitrogen atom is connected to the radical U and the sulphur atom to the radical A. The following embodiments additionally relate to the radical of the formula (II) in the unlinked state. The linkage of the radical of the formula (II) to the toxophore via the linking unit can take place either via the terminal carboxyl group, the terminal amino group, amide group, urea group, thioamide group, thiourea group, amidine group or guanidine group or via a functional group in the side chain of the radical of the formula (II), i.e. via the radical $R^2$ or a substituent on the group U or V, whereby in the linked state the terminal carboxyl group or the terminal amino group, amide group, urea group, thioamide group, thiourea group, amidine group or guanidine group is converted into corresponding bridging units.

The radicals of the formula (II) according to the invention are characterized in that they have, as a main structural element, a biphenyl nucleus which bridges a radical having a terminal carboxyl group with a radical including at least one nitrogen atom in the main chain, which is a constituent of an amino group, amide group, urea group, thioamide group, thiourea group, amidine group or guanidine group optionally incorporated into a cyclic ring system. The biphenyl nucleus can moreover carry further substituents in addition to the abovementioned radicals.

The terminal carboxyl unit, if the bonding of the radical of the formula (II) does not take place via this, can be present as a free carboxylic acid or as an ester. In the case in which the terminal carboxyl unit is esterified, fundamentally all carboxylic acid esters obtainable by conventional processes, such as the corresponding alkyl esters, cycloalkyl esters, aryl esters and hetereocyclic analogues thereof, can be used according to the invention, alkyl esters, cycloalkyl esters and aryl esters being preferred and it being possible for the alcoholic radical to carry further substituents. $C_{1-6}$-Alkyl esters such as the methyl ester, ethyl ester, propyl ester, isopropyl ester, butyl ester, isobutyl ester, t-butyl ester, pentyl ester, isopentyl ester, neopentyl ester, hexyl ester, cyclopropyl ester, cyclopropylmethyl ester, cyclobutyl ester, cyclopentyl ester, cyclohexyl ester, or aryl esters such as the phenyl ester, benzyl ester or tolyl ester are particularly preferred.

Preferably, however, the radicals of the formula (II) according to the invention are used in a form in which the terminal carboxyl unit is present as a free carboxylic acid.

The terminal carboxyl unit is connected to the biphenyl nucleus via an alkylene chain which can optionally carry further substituents. Within certain limits, it is possible to control the biological activity of the radicals of the formula (II) according to the invention against integrin receptors such as, in particular, the $\alpha_v\beta_3$ receptor, by means of the distance between the terminal carboxyl unit and the nitrogen atom of an amino group, amide group, urea group, thioamide group, thiourea group, amidine group or guanidine group which is found in the main chain of the radical linked to the phenyl ring B of the biphenyl nucleus, it being possible in the case in which more than one nitrogen atom is present in the main chain of the corresponding radical for the nitrogen atom found near to the phenyl ring B of the biphenyl nucleus to be decisive. In addition to the biphenyl nucleus, preferably not more than 6 atoms should be found in the main chain between these two structural elements. More preferred, however, are radicals of the formula (II), in which, additionally to the biphenyl nucleus in the main chain between the terminal carboxyl unit and the nitrogen atom of the amino group, amide group, urea group, thioamide group, thiourea group, amidine group or guanidine group which is found in the main chain of the radical linked to the phenyl ring B of the biphenyl nucleus, less than 6 additional atoms are found. According to the present invention, radicals of the formula (II) are particularly preferred in which the abovementioned nitrogen atom of the amino group, amide group, urea group, thioamide group, thiourea group, amidine group or guanidine group is bonded directly to the phenyl ring B of the biphenyl nucleus and at the same time the terminal carboxyl unit is separated from the phenyl ring A of the biphenyl nucleus by two to four atoms in the main chain.

The alkylene chain which connects the terminal carboxyl group to the phenyl ring A of the biphenyl nucleus can alternatively carry additional substituents of any of the carbon atoms forming the alkylene chain. These substituents can be selected from the group which consists of hydrogen, a substituted or unsubstituted alkyl or cycloalkyl radical, a substituted or unsubstituted aryl radical, a saturated or unsaturated, optionally substituted heterocyclic radical, an optionally substituted alkenyl radical, an optionally substituted alkinyl radical, —$NR^{2'}_2$, —$NR^{2'}SO_2R^{2''}$, —$NR^{2'}COOR^{2''}$, —$NR^{2'}COR^{2'}$, —$NR^{2'}CONR^{2'}_2$ or —$NR^{2'}CSNR^{2'}_2$, where $R^{2'}$ can be hydrogen, a substituted or unsubstituted alkyl or cycloalkyl radical, a substituted or unsubstituted aryl radical or a saturated or unsaturated, optionally substituted heterocyclic radical and $R^{2''}$ can be a substituted or unsubstituted alkyl or cycloalkyl radical, a substituted or unsubstituted aryl radical or a saturated or unsaturated, optionally substituted heterocyclic radical. The alkyl radical can preferably be a $C_{1-6}$-alkyl such as, for example, methyl, ethyl, propyl, isopropyl, butyl, isobutyl, t-butyl, pentyl, isopentyl, neopentyl or hexyl. The cycloalkyl radical can preferably be a $C_{3-7}$-cycloalkyl such as, for example, cyclopropyl, cyclopropylmethyl, cyclobutyl, cyclopentyl or cyclo-hexyl. The aryl radical can preferably be phenyl, benzyl or tolyl. The heterocyclic radical can preferably be pyrrole, pyridine, tetrahydrofuran, furan, thiophene, tetrahydrothiophene, oxathiazole, benzofuran, quinoline, isoquinoline or pyrimidine. The alkenyl radical can be a terminal or internal E- or Z-alkene unit. The abovementioned radicals can alternatively be substituted by one or more $C_{1-6}$alkyl radicals such as methyl, ethyl, propyl, isopropyl, butyl, isobutyl, t-butyl, pentyl, isopentyl, neopentyl or hexyl, $C_{3-7}$-cycloalkyl radicals such as cyclopropyl, cyclo-propylmethyl, cyclobutyl, cyclopentyl or cyclohexyl, aryl radicals such as phenyl, benzyl, tolyl, naphthyl, heterocyclic radicals such as pyrrole, pyridine, tetra-hydrofuran, furan, thiophene, tetrahydrothiophene, oxazole, thiazole, oxathiazole, benzofuran, benzoxazole, benzothiazole, quinoline, isoquinoline, or functional groups such as a double bond to a heteroatom such as oxygen, sulphur or nitrogen, an optionally substituted amino group, a nitro group, a halogen, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. Furthermore, one or more additionally saturated or unsaturated rings can be fused to the abovementioned cyclic radicals with formation of, for example, a naphthyl, benzofuranyl, benzoxazolyl, benzothiazolyl, quinolinyl or iso-quinolinyl unit or a partially or completely hydrogenated analogue thereof.

$-NR^{2'}_2$, $-NR^{2'}SO_2R^{2''}$, $-NR^{2'}COOR^{2''}$, $-NR^{2'}COR^{2'}$, $-NR^{2'}CONR^{2'}_2$ or $-NR^{2'}CSNR^{2'}_2$ are preferred among the substituents optionally found on the alkylene chain connecting the terminal carboxyl group to the phenyl ring A of the biphenyl nucleus, where $R^{2'}$ can be hydrogen, a substituted or unsubstituted alkyl or cycloalkyl radical, a substituted or unsubstituted aryl radical or a saturated or unsaturated, optionally substituted heterocyclic radical and $R^{2''}$ can be a substituted or unsubstituted alkyl or cycloalkyl radical, a substituted or unsubstituted aryl radical or a saturated or unsaturated, optionally substituted heterocyclic radical. Preferably, $R^{2'}$ is selected from the group which consists of hydrogen, a $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclobutyl, cyclopentyl, cyclohexyl, phenyl, benzyl, tolyl or a substituted derivative thereof, while $R^{2''}$ is preferably selected from the group which consists of a $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclobutyl, cyclopentyl, cyclohexyl, phenyl, benzyl, tolyl or a substituted derivative thereof, $-C_6H_2(CH_3)_3$, 2-chlorophenyl, 4-chlorophenyl, 2,5-dichlorophenyl, 4-trifluoromethylphenyl, camphor-10-yl, 4-methoxyphenyl, 4-t-butylphenyl, 2,5-dimethylphenyl, 3-chlorophenyl, 2-methoxy-5-methylphenyl, 2,3,5,6-tetramethylphenyl, 2,3-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-aminophenyl, 4-aminophenyl, 3-(N-acetyl-6-methoxy)aniline or 8-quinolinyl.

According to the invention, particularly preferred radicals of the formula (II) are those in which an amide, urea, sulphonamide or carbamate group is found in the alkylene chain which connects the terminal carboxyl group to the phenyl ring A of the biphenyl nucleus. Preferably, the amide, urea, sulphonamide or carbamate group is found in the α- or β-position to the terminal carboxyl group. However, there can also be more than 2 carbon atoms between the carboxyl carbon of the terminal carboxyl group and the nitrogen atom of the sulphonamide or carbamate unit. According to the present invention, the sulphonamide group, if present, particularly preferably carries a radical $R^{2''}$ on the sulphur atom, which is selected from the group consisting of phenyl, benzyl, tolyl or a substituted derivative thereof, $-C_6H_2(CH_3)_3$, 2-chlorophenyl, 4-chlorophenyl, 2,5-dichlorophenyl, 4-trifluoromethylphenyl, 3-aminophenyl, 4-aminophenyl, camphor-10-yl, 4-methoxyphenyl, 4-t-butylphenyl, 2,5-dimethylphenyl, 3-chlorophenyl, 2-methoxy-5-methylphenyl, 2,3,5,6-tetramethylphenyl, 2,3-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 3-aminobenzyl, 4-aminobenzyl, 2-trifluoromethylphenyl, 2-alkylsulphonylphenyl, 2-arylsulphonylphenyl, 3-(N-acetyl-6-methoxy)aniline or 8-quinolinyl. The carbamate group, if present, particularly preferably carries a radical $R^{2''}$ as an alcoholic portion, which is selected from the group consisting of phenyl, benzyl, tolyl or a substituted derivative thereof, and particularly preferably a benzyl radical, 3-aminobenzyl or 4-aminobenzyl.

According to a further embodiment, the present invention relates to radicals of the formula (II), in which the terminal carboxyl group is bonded to the phenyl ring A of the biphenyl nucleus via an alkylenesulphonamide unit or an alkyleneamide unit, i.e. an $-NRSO_2-$ or $-NR-CO$ group is inserted between the alkylene chain and the phenyl ring A of the biphenyl nucleus, the phenyl ring A of the biphenyl nucleus being bonded to the sulphur atom of the sulphonamide unit or the carboxyl carbon atom of the amide unit. The alkylene chain between the terminal carboxyl group and the sulphonamide or amide unit can in this case optionally carry further substituents in accordance with the above details, where a $C_{1-6}$-alkyl such as, for example, methyl, ethyl, propyl, isopropyl, butyl, isobutyl, t-butyl, pentyl, isopentyl, neopentyl or hexyl, a $C_{3-7}$-cycloalkyl such as, for example, cyclopropyl, cyclopropylmethyl, cyclobutyl, cyclopentyl or cyclohexyl, an aryl such as, for example, phenyl, benzyl, phenylethyl or tolyl, a heterocyclic radical such as pyrrole, pyridine, tetrahydrofuran, furan, thiophene, tetrahydrothiophene, oxathiazole, benzofuran, quinoline, iso-quinoline or pyrimidine, or a terminal or internal E- or Z-alkene unit is preferred, which can alternatively be substituted by one or more $C_{1-6}$-alkyl radicals such as methyl, ethyl, propyl, isopropyl, butyl, isobutyl, t-butyl, pentyl, isopentyl, neopentyl or hexyl, $C_{3-7}$-cycloalkyl radicals such as cyclopropyl, cyclopropylmethyl, cyclo-butyl, cyclopentyl or cyclohexyl, aryl radicals such as phenyl, benzyl, tolyl, naphthyl, heterocyclic radicals such as pyrrole, pyridine, tetrahydrofuran, furan, thiophene, tetrahydrothiophene, oxathiazole, benzofuran, quinoline, isoquinoline or pyrimidine, or functional groups such as a double bond to a heteroatom such as oxygen, sulphur or nitrogen, an optionally substituted amino group, a nitro group, a halogen, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. Furthermore, one or more additionally saturated or unsaturated rings can be fused to the abovementioned cyclic radicals with formation of, for example, a naphthyl, benzofuranyl, benzoxazolyl, benzothiazolyl, quinolinyl or isoquinolinyl unit or a partially or completely hydrogenated analogue thereof.

Particularly preferred radicals of the formula (II) according to this embodiment are those in which the alkylene chain which connects the terminal carboxyl group and the bridging sulphonamide or amide unit has an optionally substituted phenyl or benzyl radical such as, for example, β-3-aminophenyl, β-4-aminophenyl or α-4-aminobenzyl in the α- or β-position relative to the terminal carboxyl unit.

In the radicals of the formula (II) of this embodiment, in which a sulphonamide or amide unit is inserted between the corresponding alkylene chain and the phenyl ring A of the biphenyl nucleus, the alkylene chain between the terminal carboxyl group and the bridging sulphonamide or amide unit should preferably include not more than two carbon atoms in this main chain in order that, as mentioned above, in addition to the biphenyl nucleus preferably not more than five atoms are present between the terminal carboxyl group and the nitrogen atom of the amino group, amide group, urea group, thioamide group, thiourea group, amidine group or guanidine group which is next to the phenyl ring B in the main chain of the radical linked to the phenyl ring B of the biphenyl nucleus.

The nitrogen atom of the bridging sulphonamide or amide unit can optionally be substituted by a radical which is selected from the group consisting of hydrogen, a $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclopropylmethyl, cyclobutyl, cyclopentyl, cyclohexyl, an aryl such as, for example, phenyl, benzyl, tolyl or a substituted derivative thereof such as, for example, phenylethyl, phenylpropyl or phenoxyethyl.

The biphenyl nucleus is the central structural element of the radicals of the formula (II) according to the invention. In the unlinked state, it bridges the radical including the terminal carboxyl group on the phenyl ring A to the radical on the phenyl ring B which includes at least one nitrogen atom of an amino group, amide group, urea group, thioamide group, thiourea group, amidine group or guanidine group in its main chain. Preferably, it moreover carries no further substituents. Each of the two phenyl rings, however, can carry additional substituents. Preferably, the phenyl ring A, i.e. the ring connected to the radical including the terminal carboxyl group, carries one or more additional alkoxy radicals, preferably a $C_{1-6}$-alkoxy radical such as methoxy, ethoxy, propoxy, butoxy, pentoxy or hexoxy, particularly preferably one or more methoxy radicals, and the phenyl ring B, i.e. the ring to which the radical including at least one nitrogen atom of an amino group, amide group, urea group, thioamide group, thiourea group, amidine group or guanidine group is bonded in its main chain, carries one or more alkyl radicals, preferably a $C_{1-6}$-alkyl radical such as methyl, ethyl, propyl, isopropyl, butyl, isobutyl, t-butyl, pentyl, isopentyl, neopentyl, hexyl, a $C_{3-7}$-cycloalkyl radical such as cyclopropyl, cyclobutyl, cyclopentyl, cyclohexyl, and particularly preferably one or more methyl groups. In this case, the phenyl rings A and B can independently of one another carry one or more of the abovementioned additional substituents.

The two phenyl rings can be 1,3- or 1,4-linked to one another and to the radical including the terminal carboxyl group and the radical including at least one nitrogen atom of an amino group, amide group, urea group, thioamide group, thiourea group, amidine group or guanidine group in its main chain, i.e. the radical including the terminal carboxyl group and the phenyl ring B can be substituted in the meta- or para-position relative to one another in the phenyl ring A, and at the same time the phenyl ring A and the radical including at least one nitrogen atom of an amino group, amide group, urea group, thioamide group, thiourea group, amidine group or guanidine group in its main chain can be substituted in the meta- or para-position on the phenyl ring B relative to one another, each combination of the abovementioned substitution patterns being possible for the biphenyl nucleus of the radicals of the formula (II) according to the invention. According to the present invention, particularly preferred radicals of the formula (II) are those whose biphenyl nucleus consists according to the above definition of a p-substituted phenyl ring A and a p-substituted phenyl ring B, a p-substituted phenyl ring A and an m-substituted phenyl ring B, an m-substituted phenyl ring A and a p-substituted phenyl ring B, or an m-substituted phenyl ring A and an m-substituted phenyl ring B. According to the present invention, particularly preferred radicals of the formula (II) are those whose biphenyl nucleus consists according to the present definition of a p-substituted phenyl ring A and an m-substituted phenyl ring B.

As a third structural element, the radicals of the formula (II) according to the invention in the unlinked state contain, in addition to the biphenyl nucleus and the radical including a terminal carboxyl group, a group which in its main chain comprises at least one nitrogen atom of an amino group, amide group, urea group, thioamide group, thiourea group, amidine group or guanidine group. This nitrogen atom can be bonded to the phenyl ring B of the biphenyl nucleus directly or via an alkylene chain. This alkylene chain preferably consists of at most 4 carbon atoms in the main chain, where, from the abovementioned considerations, not more than 6 further atoms should be present in addition to the biphenyl nucleus between the terminal carboxyl group and the nitrogen atom of the amino group, amide group, urea group, thioamide group, thiourea group, amidine group or guanidine group which is next to the phenyl ring B. Alternatively, this alkylene chain can carry further substituents which are selected from the group consisting of hydrogen, a $C_{1-6}$-alkyl such as, for example, methyl, ethyl, propyl, isopropyl, butyl, isobutyl, t-butyl, pentyl, isopentyl, neopentyl or hexyl, a $C_{3-7}$-cycloalkyl such as, for example, cyclopropyl, cyclopropylmethyl, cyclobutyl, cyclopentyl or cyclohexyl, an aryl such as, for example, phenyl, benzyl or tolyl, a heterocyclic radical such as pyrrole, pyridine, tetrahydrofuran, furan, thiophene, tetrahydrothiophene, oxathiazole, benzofuran, quinoline, isoquinoline or pyrimidine, or a terminal or internal E- or Z-alkene unit, and can alternatively be substituted by one or more $C_{1-6}$-alkyl radicals such as methyl, ethyl, propyl, isopropyl, butyl, isobutyl, t-butyl, pentyl, isopentyl, neopentyl or hexyl, cycloalkyl radicals such as cyclopropyl, cyclopropylmethyl, cyclobutyl, cyclopentyl or cyclohexyl, aryl radicals such as phenyl, benzyl, tolyl, naphthyl, indolyl, heterocyclic radicals such as pyrrole, pyridine, tetrahydrofuran, furan, thiophene, tetrahydrothiophene, oxathiazole, benzofuran, quinoline, isoquinoline or pyrimidine, or functional groups such as a double bond to a heteroatom such as oxygen, sulphur or nitrogen, an optionally substituted amino group, a nitro group, a halogen, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. Furthermore, one or more additionally saturated or unsaturated rings can be fused to the abovementioned cyclic radicals with formation of, for example, a naphthyl, indolyl, benzofuranyl, benzoxazolyl, benzothiazolyl, benzimidazolyl, quinolinyl or isoquinolinyl unit or a partially or completely hydrogenated analogue thereof.

The nitrogen atom found in the main chain of the radical bonded to the phenyl ring B of the biphenyl nucleus, which is next to the phenyl ring B, can, if the bonding of the radical of the formula (II) does not take place via this, either be a constituent of an optionally substituted amino group or be in the direct vicinity of a —C=O unit, —CONR$_2$ unit, —C=S unit, —CSNR$_2$ unit, —C=NR unit or a —CNRNR$_2$ unit and thus be a constituent of an amide group, urea group, thioamide group, thiourea group, amidine group or guanidine group.

In the case in which the nitrogen atom found in the main chain of the radical bonded to the phenyl ring B of the biphenyl nucleus, which is next to the phenyl ring B, is a constituent of an amino group, it can be unsubstituted or can carry one or two substituents, i.e. be a constituent of a primary, secondary or tertiary amino group. These substituents can be independent of one another or, simultaneously, hydrogen, a substituted or unsubstituted alkyl or cycloalkyl radical, a substituted or unsubstituted aryl radical, a saturated or unsaturated, optionally substituted heterocyclic radical, an alkylamine radical, an alkylamide radical or can be connected to one another and thus form, together with the nitrogen atom to which they are bonded, a heterocyclic ring system. In this case, preferred substituents are those which are selected from the group consisting of hydrogen, a $C_{1-6}$-alkyl such as, for example, methyl, ethyl, propyl, isopropyl, butyl, isobutyl, t-butyl, pentyl, isopentyl, neopentyl or hexyl, a $C_{3-7}$-cycloalkyl such as, for example, cyclopropyl, cyclopropylmethyl, cyclobutyl, cyclopentyl or cyclohexyl, an aryl such as, for example, phenyl, benzyl or tolyl, a heterocyclic radical such as, for example, pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, oxathiazole, benzofuran, benzoxazole, benzothiazole, benzimidazole, quinoline, isoquinoline, tetra-hydroquinoline, tetrahydroisoquinoline, triazole, tetrazole, pyrimidine, purine, cytosine, thymine, uracil, adenine, guanine or xanthine, or a terminal or internal E- or Z-alkene unit, and can alternatively be substituted by one or more $C_{1-6}$-alkyl radicals such as methyl, ethyl, propyl, isopropyl, butyl, isobutyl, t-butyl, pentyl, isopentyl, neopentyl or hexyl, $C_{3-7}$-cycloalkyl radicals such as cyclopropyl, cyclopropylmethyl, cyclobutyl, cyclopentyl or cyclohexyl, aryl radicals such as phenyl, benzyl, tolyl, naphthyl, indolyl, heterocyclic radicals such as pyrrolidine, piperidine, piperazine, pyrrole, pyridine, tetrahydrofuran, furan, thiophene, tetrahydrothiophene, imidazoli-dine, imidazole, oxazolidine, oxazole, thiazolidine, thiazole, oxathiazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or functional groups such as a double bond to a heteroatom such as oxygen, sulphur or nitrogen, an optionally substituted amino group, a nitro group, a halogen, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. Furthermore, one or more additionally saturated or unsaturated rings can be fused to the abovementioned cyclic radicals with formation of, for example, a naphthyl, indolyl, benzofuranyl, benzoxazolyl, benzothiazolyl, benzimidazolyl, quinolinyl or isoquinolinyl unit or a partially or completely hydrogenated analogue thereof. Particularly preferred substituents are those such as hydrogen, methyl, ethyl, propyl, isopropyl, butyl, isobutyl, t-butyl, pentyl, isopentyl, neopentyl, hexyl, cyclopropyl, cyclo-propyl-methyl, cyclobutyl, cyclopentyl, cyclohexyl, 4-methylcyclohexyl, 3,3,5-trimeth-ylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl,

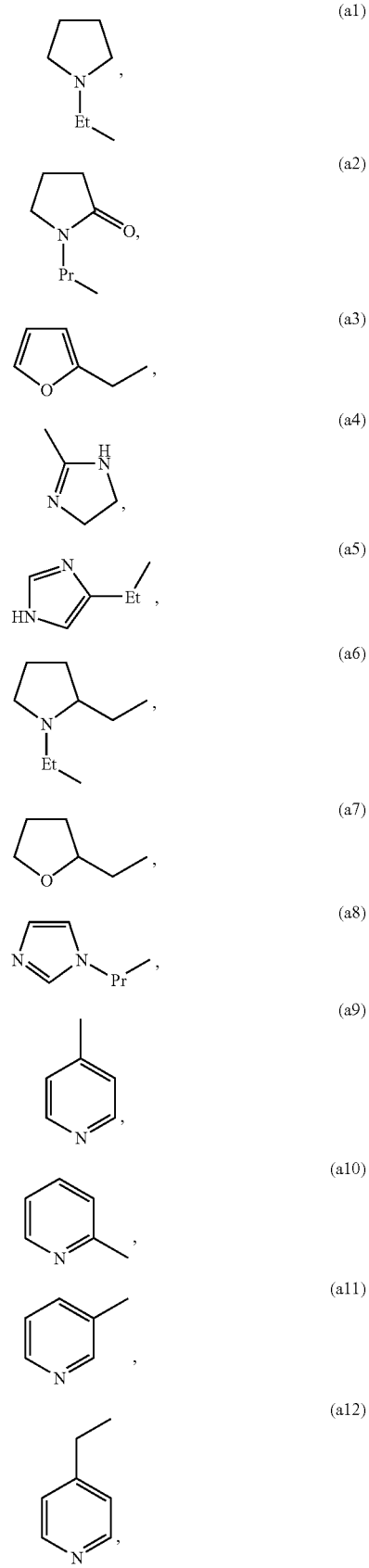

-continued
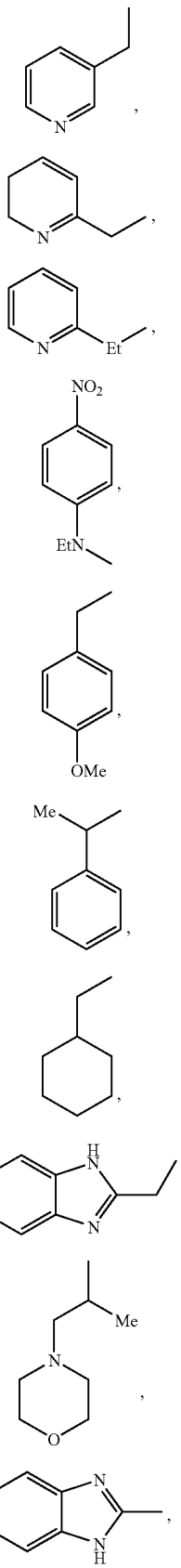
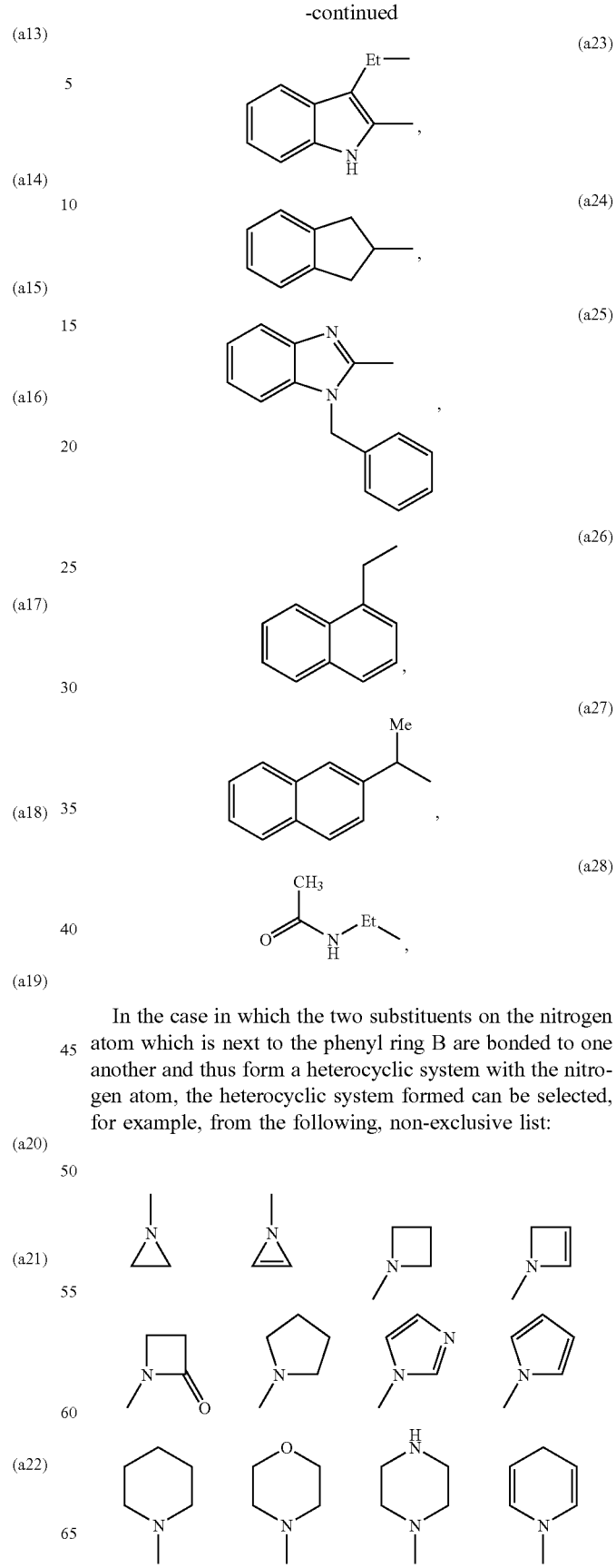
In the case in which the two substituents on the nitrogen atom which is next to the phenyl ring B are bonded to one another and thus form a heterocyclic system with the nitrogen atom, the heterocyclic system formed can be selected, for example, from the following, non-exclusive list:

-continued

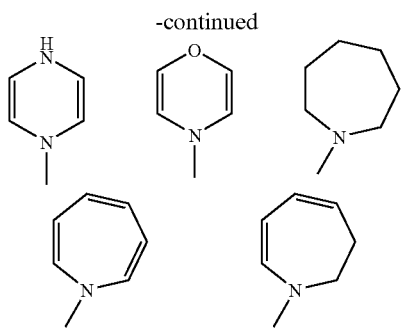

where the ring systems shown can carry one or more radicals which are selected from the group consisting of hydrogen, a $C_{1-6}$-alkyl such as, for example, methyl, ethyl, propyl, isopropyl, butyl, isobutyl, t-butyl, pentyl, isopentyl, neopentyl or hexyl, a $C_{3-7}$-cycloalkyl such as, for example, cyclopropyl, cyclopropylmethyl, cyclobutyl, cyclopentyl or cyclohexyl, an aryl such as, for example, phenyl, benzyl or tolyl, a heterocyclic radical such as, for example, pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, oxathiazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or a terminal or internal E- or Z-alkene unit, and can alternatively be substituted by one or more $C_{1-6}$-alkyl radicals such as methyl, ethyl, propyl, isopropyl, butyl, isobutyl, t-butyl, pentyl, isopentyl, neopentyl or hexyl, $C_{3-7}$-cycloalkyl radicals such as cyclopropyl, cyclopropylmethyl, cyclobutyl, cyclopentyl or cyclohexyl, aryl radicals such as phenyl, benzyl, tolyl, naphthyl, indolyl, heterocyclic radicals such as pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, oxathiazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or functional groups such as a double bond to a heteroatom such as oxygen, sulphur or nitrogen, an optionally substituted amino group, a nitro group or a halogen, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. Furthermore, one or more additionally saturated or unsaturated rings can be fused to the abovementioned cyclic radicals with formation of, for example, a naphthyl, indolyl, benzofuranyl, benzoxazolyl, benzothiazolyl, benzimidazolyl, quinolinyl or isoquinolinyl unit or a partially or completely hydrogenated analogue thereof.

Of the ring systems shown above, the four- to six-membered ring systems are preferred.

As mentioned above, the nitrogen atom in the main chain of the radical bonded to the phenyl ring B of the biphenyl nucleus, which is next to the phenyl ring B, can also be a constituent of one of the following preferred functional units:

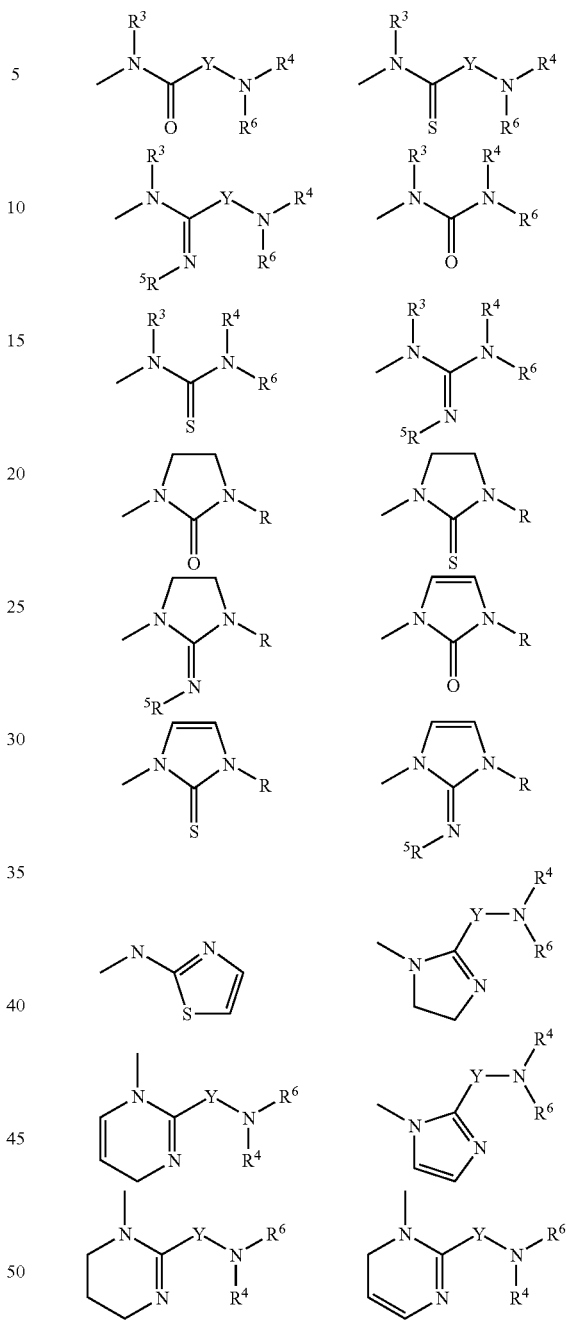

where the above list is not an exclusive enumeration of all possible structural units.

According to the invention, in addition to the abovementioned preferred structural units, their analogues are also included in which one or more 4- to 6-membered ring systems are fused to the heterocycle, such as, for example, the corresponding benzofused analogues of the above structural units.

In the structural units shown above, $R^3$, $R^4$ and $R^6$ can each be hydrogen, a $C_{1-6}$-alkyl such as, for example, methyl, ethyl, propyl, isopropyl, butyl, isobutyl, t-butyl, pentyl, isopentyl, neopentyl or hexyl, a $C_{3-7}$-cycloalkyl such as, for example, cyclopropyl, cyclopropylmethyl, cyclobutyl, cyclopentyl or cyclohexyl, an aryl such as, for example, phenyl, benzyl or tolyl, a heterocyclic radical such as, for example, pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, oxathiazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or a terminal or internal E- or Z-alkene unit and can alternatively be substituted by one or more $C_{1-6}$-alkyl radicals such as methyl, ethyl, propyl, isopropyl, butyl, isobutyl, t-butyl, pentyl, isopentyl, neopentyl or hexyl, $C_{3-7}$-cycloalkyl radicals such as cyclopropyl, cyclopropylmethyl, cyclobutyl, cyclopentyl or cyclohexyl, aryl radicals such as phenyl, benzyl, tolyl, naphthyl, indolyl, heterocyclic radicals such as pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, oxathiazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or functional groups such as a double bond to a heteroatom such as oxygen, sulphur or nitrogen, an optionally substituted amino group, a nitro group, a halogen, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. Particularly preferred substituents are those such as hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, or one of the abovementioned radicals (a1) to (a28).

In the above structural units, $R^4$ and $R^6$, however, can also be bonded to one another and, with the nitrogen atom to which they are bonded, form a heterocyclic ring system. Examples of this which can be mentioned are:

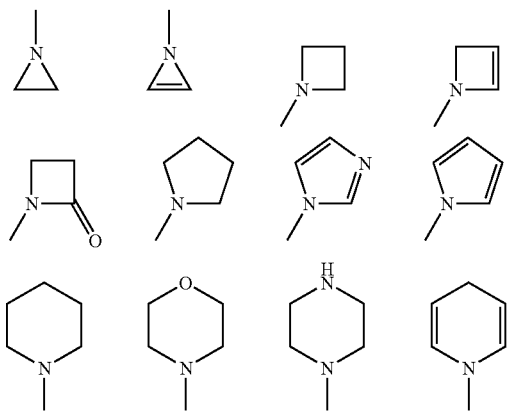

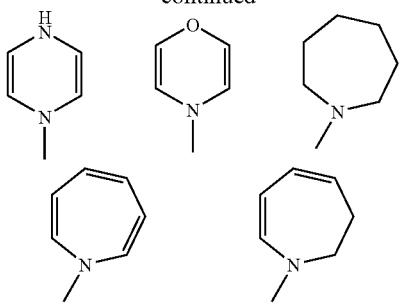

where the above enumeration is non-exclusive and the ring systems formed from the combination of $R^4$ and $R^6$ can carry one or more radicals which are selected from the group consisting of hydrogen, a $C_{1-6}$-alkyl such as, for example, methyl, ethyl, propyl, isopropyl, butyl, isobutyl, t-butyl, pentyl, isopentyl, neopentyl or hexyl, a $C_{3-7}$-cycloalkyl such as, for example, cyclopropyl, cyclopropylmethyl, cyclobutyl, cyclopentyl or cyclohexyl, an aryl such as, for example, phenyl, benzyl or tolyl, a heterocyclic radical such as, for example, pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, oxathiazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or a terminal or internal E- or Z-alkene unit, and can alternatively be substituted by one or more $C_{1-4}$-alkyl radicals such as methyl, ethyl, propyl, isopropyl, butyl, isobutyl, t-butyl, pentyl, isopentyl, neopentyl or hexyl, $C_{3-7}$-cycloalkyl radicals such as cyclopropyl, cyclopropylmethyl, cyclobutyl, cyclopentyl or cyclohexyl, an aryl radical such as phenyl, benzyl, tolyl, naphthyl, indolyl, heterocyclic radicals such as pyrrolidine, piperidine, piperazine, pyrrole, pyridine, tetrahydrofuran, furan, thiophene, tetrahydrothiophene, imidazo-lidine, imidazole, oxazolidine, oxazole, thiazolidine, thiazole, oxathiazole, benzo-furan, benzoxazole, benzothiazole, benzimidazole, quinoline, isoquinoline, tetra-hydroquinoline, tetrahydroisoquinoline, triazole, tetrazole, pyrimidine, purine, cytosine, thymine, uracil, adenine, guanine or xanthine, or functional groups such as a double bond to a heteroatom such as oxygen, sulphur or nitrogen, an optionally substituted amino group, a nitro group, a halogen, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. Furthermore, one or more additionally saturated or unsaturated rings can be fused to the abovementioned cyclic radicals with formation of, for example, a naphthyl, indolyl, benzofuranyl, benzoxazolyl, benzothiazolyl, benzimidazolyl, quinolinyl or isoquinolinyl unit or a partially or completely hydrogenated analogue thereof. Of the ring systems formed from the combination of $R^4$ and $R^6$, the four- to six-membered ring systems are preferred.

Furthermore, in the above structural units $R^5$ can be —$NO_2$, —CN, —$COR^5$ or —$COOR^{5'}$, where $R^{5''}$ can be a substituted or unsubstituted alkyl or cycloalkyl radical, a substituted or unsubstituted aryl radical or a saturated or unsaturated, optionally substituted heterocyclic radical, which can be saturated or unsaturated and/or can contain further heteroatoms, and is preferably a $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclobutyl, cyclopentyl, cyclohexyl, an aryl such as, for example, phenyl, benzyl or tolyl or a substituted derivative thereof.

Furthermore, in the above structural units Y can be absent or can be an alkylene or alkine unit which in its main chain carries 1 to 5 carbon atoms. According to the invention, Y, if present, preferably has a main chain consisting of one carbon atom. Y can moreover carry one or more radicals which are selected from the group consisting of hydrogen, a $C_{1-6}$-alkyl such as, for example, methyl, ethyl, propyl, isopropyl, butyl, isobutyl, t-butyl, pentyl, isopentyl, neopentyl or hexyl, a $C_{3-7}$-cycloalkyl such as, for example, cyclopropyl, cyclopropylmethyl, cyclobutyl, cyclo-pentyl or cyclohexyl, an aryl such as, for example, phenyl, benzyl or tolyl, a heterocyclic radical such as, for example, pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, oxathiazole, benzofuran, benzoxazole, benzothiazole, benzimidazole, quinoline, isoquinoline, tetrahydro-quinoline, tetrahydroisoquinoline, triazole, tetrazole, pyrimidine, purine, cytosine, thymine, uracil, adenine, guanine or xanthine, or a terminal or internal E- or Z-alkene unit, and can alternatively be substituted by one or more $C_{1-6}$-alkyl radicals such as methyl, ethyl, propyl, isopropyl, butyl, isobutyl, t-butyl, pentyl, isopentyl, neopentyl or hexyl, $C_{3-7}$-cycloalkyl radicals such as cyclopropyl, cyclopropylmethyl, cyclobutyl, cyclopentyl or cyclohexyl, aryl radicals such as phenyl, benzyl, tolyl, naphthyl, indolyl, heterocyclic radicals such as pyrrolidine, piperidine, piperazine, pyrrole, pyridine, tetrahydrofuran, furan, thiophene, tetrahydrothiophene, imidazoli-dine, imidazole, oxazolidine, oxazole, thiazolidine, thiazole, oxathiazole, benzofuran, benzoxazole, benzothiazole, benzimidazole, quinoline, isoquinoline, tetrahydro-quinoline, tetrahydroisoquinoline, triazole, tetrazol, pyrimidine, purine, cytosine, thymine, uracil, adenine, guanine or xanthine, or functional groups such as a double bond to a heteroatom such as oxygen, sulphur or nitrogen, an optionally substituted amino group, a nitro group, a halogen, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. Furthermore, one or more additionally saturated or unsaturated rings can be fused to the abovementioned cyclic radicals with formation of, for example, a naphthyl, indolyl, benzofuranyl, benzoxazolyl, benzothiazolyl, benzimidazolyl, quinolinyl or isoquinolinyl unit or a partially or completely hydrogenated analogue thereof.

According to the invention, particularly preferred radicals of the formula (II) are those in which, if the linkage to the rest of the conjugate does not take place via this, the nitrogen atom found in the main chain of the radical bonded to the phenyl ring B, which is next to the phenyl ring B, is a constituent of the urea or thiourea unit. Particularly preferred radicals of the formula (II) in this case are those in which a urea or thiourea unit is bonded directly to the phenyl ring B of the biphenyl nucleus.

The moiety addressing $\alpha_v\beta_3$ integrin receptors can furthermore be a radical of the formula (III):

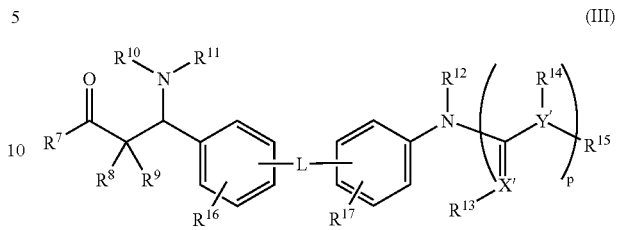

(III)

where the radicals in the formula (III) have the meaning defined above.

In the description below, bivalent substituents are indicated such that their respective left end is connected to the group indicated left of the corresponding substituent in formula (III) and their respective right end is connected to the group indicated right of the corresponding substituent in formula (III). If, for example, the radical L is equal to —$(CH_2)_m NHSO_2(CH_2)_n$— in formula (III), the nitrogen atom is connected to the phenylene group found left of the radical L in formula (III) via the group $(CH_2)_m$. The following details additionally relate to the radical of the formula (III) in the unlinked state. The linkage of the radical of the formula (III) to the toxophore via the linking unit can take place either via the terminal carboxyl group, the terminal amino group, urea group, thiourea group, guanidine group or the group $NR^{12}CX'R^{13}S$— or via a functional group in the side chain of the radical of the formula (III), i.e. via the amino group or a substituent attached thereon in the β-position relative to the terminal carboxyl group, whereby in the linked state the terminal carboxyl group and the terminal amino group, urea group, thiourea group, guanidine group or the group $NR^{12}CX'R^{13}S$— are converted into corresponding bridging units.

The radicals of the formula (III) according to the invention are characterized in that they have, as a main structural element, two phenyl units connected via a linker group L, one phenylene group of which has a radical derived from a β-amino acid, while the other phenylene group has an amino group, urea group, thiourea group or guanidine group optionally incorporated into a cyclic ring system. The phenylene units connected via a linker group L can moreover carry further substituents in addition to the abovementioned radicals.

The terminal carboxyl units included in the radical derived from a β-amino acid can, if the linkage to the radical of the conjugate does not take place via this, be present as a free carboxylic acid or as an ester. In the case in which the terminal carboxyl unit is esterified, fundamentally all carboxylic acid esters obtainable by conventional processes, such as the corresponding alkyl esters, cycloalkyl esters, aryl esters and heterocyclic analogues thereof can be used according to the invention, where alkyl esters, cycloalkyl esters and aryl esters are preferred and the alcoholic radical can carry further substituents. Particularly preferred $C_{1-6}$-alkyl esters are those such as the methyl ester, ethyl ester, propyl ester, isopropyl ester, butyl ester, isobutyl ester, t-butyl ester, pentyl ester, isopentyl ester, neopentyl ester, hexyl ester, cyclopropyl ester, cyclopropylmethyl ester, cyclobutyl ester, cyclopentyl ester, cyclohexyl ester, or aryl esters such as the phenyl ester, benzyl ester or tolyl ester.

Preferably, the radicals of the formula (III) according to the invention are used in a form in which the terminal carboxyl unit is present as a free carboxylic acid.

The radical bonded to one of the two central phenylene units and derived from a β-amino acid can alternatively carry one or two additional substituents in the α-position relative to the carboxyl group. These substituents can each be selected from the group which consists of hydrogen, a substituted or unsubstituted alkyl or cycloalkyl radical, a substituted or unsubstituted aryl radical, a saturated or unsaturated, optionally substituted heterocyclic radical, an optionally substituted alkenyl radical, an optionally substituted alkinyl radical, a hydroxyl radical or an alkoxy radical. The alkyl radical can preferably be a $C_{1-6}$-alkyl such as, for example, methyl, ethyl, propyl, isopropyl, butyl, isobutyl, t-butyl, pentyl, isopentyl, neopentyl or hexyl. The cycloalkyl radical can preferably be a $C_{3-7}$-cycloalkyl such as, for example, cyclopropyl, cyclopropylmethyl, cyclobutyl, cyclopentyl, cyclohexyl or cycloheptyl. The aryl radical can preferably be phenyl, benzyl or tolyl. The heterocyclic radical can preferably be pyrrole, pyridine, tetrahydrofuran, furan, thiophene, tetrahydrothiophene, oxathiazole, benzofuran, quinoline, isoquinoline or pyrimidine. The alkenyl radical can be a terminal or internal E- or Z-alkene unit. The alkoxy radical can preferably be a $C_{1-6}$-alkoxy radical such as, for example, methoxy, ethoxy, propoxy, butoxy, pentoxy, hexoxy or benzyloxy. The abovementioned radicals can alternatively be substituted by one or more $C_{1-6}$-alkyl radicals such as methyl, ethyl, propyl, isopropyl, butyl, isobutyl, t-butyl, pentyl, isopentyl, neopentyl or hexyl, $C_{3-7}$-cycloalkyl radicals such as cyclopropyl, cyclopropylmethyl, cyclobutyl, cyclopentyl or cyclohexyl, aryl radicals such as phenyl, benzyl, tolyl, naphthyl, heterocyclic radicals such as pyrrole, pyridine, tetrahydrofuran, furan, thiophene, tetrahydrothiophene, oxazole, thiazole, oxathiazole, benzofuran, benzoxazole, benzothiazole, quinoline, isoquinoline, or functional groups such as a double bond to a heteroatom such as oxygen, sulphur or nitrogen, an optionally substituted amino group, a nitro group, a halogen group, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. Furthermore, one or more additionally saturated or unsaturated rings can be fused to the abovementioned cyclic radicals with formation of, for example, a naphthyl, benzofuranyl, benzoxazolyl, benzothiazolyl, quinolinyl or isoquinolinyl unit or a partially or completely hydrogenated analogue thereof.

Furthermore, the two substituents in the α-position relative to the terminal carboxyl group can, if present, be connected to one another and thus, together with the α-carbon atom of the radical derived from a β-amino acid, form a carbocyclic or heterocyclic ring system. This ring system can optionally carry further substituents and/or contain further heteroatoms. According to the invention, the above ring system, if present, is preferably a 3- to 6-membered carbocyclic or heterocyclic ring system such as, for example, a cyclopropane ring, cyclobutane ring, cyclopentane ring, cyclohexane ring, dihydrofuran ring, tetrahydrofuran ring, dihydropyran ring, tetrahydropyran ring, dioxane ring, dihydrothiophene ring, tetrahydrothiophene ring or a substituted derivative thereof.

In the groups according to the invention, the amino group included in the radical derived from a β-amino acid, if the linkage to the rest of the conjugate does not take place via this, is substituted by one of the radicals —$SO_2R^{10'}$, —$COOR^{10''}$, —$COR^{10'}$, —$CONR^{10'}{}_2$ or —$CSNR^{10'}{}_2$, where $R^{10'}$ can be hydrogen, a substituted or unsubstituted alkyl or cycloalkyl radical, a substituted or unsubstituted aryl radical or a saturated or unsaturated, optionally substituted heterocyclic radical and $R^{10'''}$ can be a substituted or unsubstituted alkyl or cycloalkyl radical, a substituted or unsubstituted aryl radical or a saturated or unsaturated, optionally substituted heterocyclic radical. Preferably, the alkyl radical in this case is a $C_{1-6}$-alkyl such as, for example, methyl, ethyl, propyl, isopropyl, butyl, isobutyl, t-butyl, pentyl, isopentyl, neopentyl, hexyl, the cycloalkyl radical is a $C_{3-7}$-cycloalkyl such as, for example, cyclopropyl, cyclobutyl, cyclopentyl, cyclohexyl, cycloheptyl, the aryl radical is an aryl such as phenyl, benzyl, tolyl or a substituted derivative thereof such as —$C_6H_2(CH_3)_3$, —$C_6(CH_3)_5$, —$CH_2C_6H_2(CH_3)_3$, 3-aminophenyl, 4-aminophenyl, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methylthiazol-5-yl, phenylethyl, 1-phenylpropyl, (S)-(+)-camphor-10-yl, (R)-(–)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethyl-phenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methylbenzothiazol-2-yl, N-methoxycarbonylpiperidin-3-yl, thiophen-2-yl, isoxazol-5-yl, ethoxy, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridin-5-methyl, 5,7-dimethyl-1,3,4-triazaindolizin-2-yl, (S)-camphan-1-yl, (R)-camphan-1-yl or 8-quinolinyl.

According to the invention, the amino group included in the radical derived from a β-amino acid is particularly preferably substituted by —$SO_2R^{10'}$, —$COOR^{10'''}$, —$CONR^{10'}{}_2$ or —$COR^{10'}$, where $R^{10'}$ and $R^{10'''}$ are as defined above. In particular, radicals of the formula (III) are preferred here in which the radical derived from a β-amino acid has no substituent in the α-position relative to the carboxyl unit and the amino group included in this radical is substituted by —$SO_2R^{10'}$, —$CONR^{10'}{}_2$ or —$COR^{10'}$, where $R^{10'}$ is as defined above.

In addition to one of the abovementioned radicals, the nitrogen atom of the amino group found in the β-position can have a substituent which is selected from the group consisting of hydrogen, a substituted or unsubstituted alkyl or cycloalkyl radical, a substituted or unsubstituted aryl radical, a saturated or unsaturated, optionally substituted heterocyclic radical or are bonded to one another and thus, together with the nitrogen atom to which they are bonded, form a heterocyclic ring system. Preferred substituents here are those which can be selected from the group consisting of hydrogen, a $C_{1-6}$-alkyl such as, for example, methyl, ethyl, propyl, isopropyl, butyl, isobutyl, t-butyl, pentyl, isopentyl, neopentyl or hexyl, a $C_{3-7}$-cycloalkyl such as, for example, cyclopropyl, cyclopropylmethyl, cyclobutyl, cyclopentyl, cyclohexyl or cycloheptyl, an aryl such as, for example, phenyl, benzyl or tolyl, a heterocyclic radical such as, for example, pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, oxathiazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine and can alternatively be substituted by one or more $C_{1-6}$-alkyl radicals such as methyl, ethyl, propyl, isopropyl, butyl, isobutyl, t-butyl, pentyl, isopentyl, neopentyl or hexyl, $C_{3-7}$-cycloalkyl radicals such as cyclopropyl, cyclo-propylmethyl, cyclobutyl, cyclopentyl or cyclohexyl, aryl radicals such as phenyl, benzyl, tolyl, naphthyl, indolyl, heterocyclic radicals such as pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, oxathiazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or functional groups such as a double bond to a heteroatom such as oxygen, sulphur or nitrogen, an optionally substituted amino group, a nitro group, a halogen, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. Furthermore, one or more additionally saturated or unsaturated rings can be fused to the abovementioned cyclic radicals with formation of, for example, a naphthyl, indolyl, benzofuranyl, benzoxazolyl, benzothiazolyl, benzimidazolyl, quinolinyl or isoquinolinyl unit or a partially or completely hydrogenated analogue thereof. The additional substituent on the nitrogen atom of the β-amino group is particularly preferably hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl,

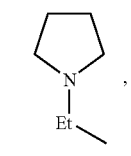

(a1)

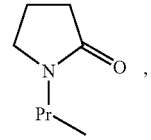

(a2)

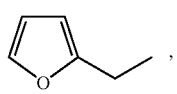

(a3)

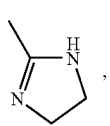

(a4)

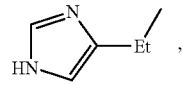

(a5)

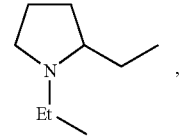

(a6)

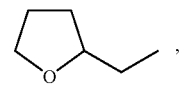

(a7)

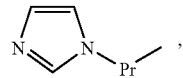

(a8)

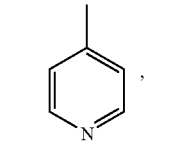

(a9)

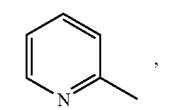

(a10)

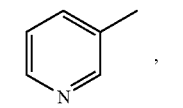

(a11)

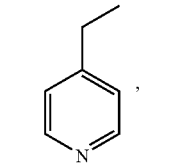

(a12)

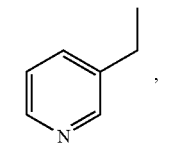

(a13)

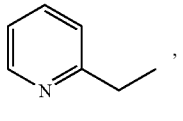

(a14)

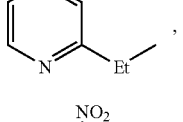

(a15)

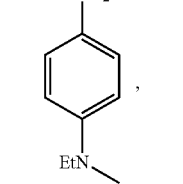

(a16)

-continued

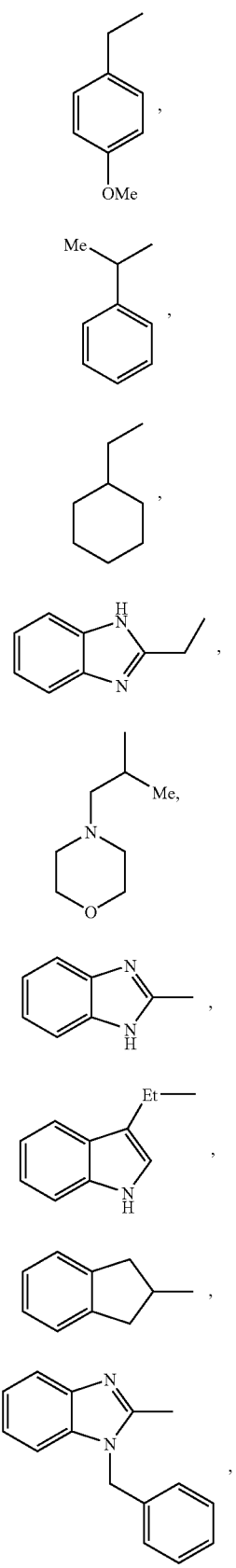

(a17)
(a18)
(a19)
(a20)
(a21)
(a22)
(a23)
(a24)
(a25)

-continued

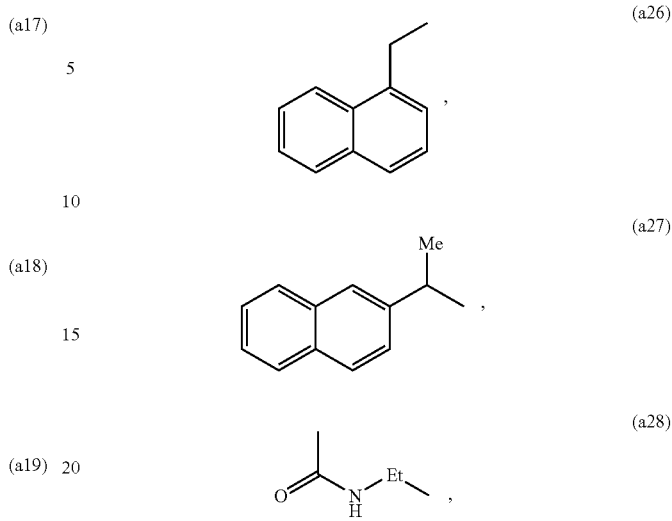

(a26)
(a27)
(a28)

The radical derived from a β-amino acid is bonded to one of the two central phenylene units connected via a linker group L, which is to be designated here as phenylene unit A. In addition to the radical derived from a β-amino acid and the linker group L, the phenylene unit A preferably carries no further substituents, but can have one or more radicals which are selected from the group consisting of hydrogen, CN, a substituted or unsubstituted alkyl or cycloalkyl radical, a substituted or unsubstituted alkoxy radical or a halogen atom. The alkyl radical(s) is/are preferably $C_{1-6}$alkyl radicals such as methyl, ethyl, propyl, isopropyl, butyl, isobutyl, t-butyl, pentyl, isopentyl, neopentyl, hexyl. The cycloalkyl radical(s) is/are preferably $C_{3-7}$-cycloalkyl radicals such as cyclopropyl, cyclobutyl, cyclopentyl, cyclohexyl, cycloheptyl. The alkoxy radical(s) is/are preferably $C_{1-6}$-alkoxy radicals such as methoxy, trifluoromethoxy, ethoxy, propoxy, butoxy, pentoxy or hexoxy, and the halogen atom(s) is/are preferably F, Cl, Br or I.

With respect to the linker group L and the radical derived from a β-amino acid or the amino, guanidine, urea or thiourea unit, the two central phenylene units can be 1,3- or 1,4-linked, i.e. the radical derived from a β-amino acid and the linker group L can be substituted in the meta- or para-position relative to one another in the phenylene unit A, and at the same time the linker group L and the amino, guanidine, urea or thiourea unit in the phenylene unit B can be substituted in the meta- or para-position relative to one another, where each combination of the abovementioned substitution patterns is possible for the central A-linker L-phenylene B unit of the radicals of the formula (III) according to the invention. Particularly preferred according to the present invention are those radicals of the formula (III) whose central phenylene A-linker L-phenylene B unit consists according to the above definition of a p-substituted phenylene unit A and a p-substituted phenylene unit B, a p-substituted phenylene unit A and an m-substituted phenylene unit B, an m-substituted phenylene unit A and a p-substituted phenylene unit B or an m-substituted phenylene unit A and an m-substituted phenylene unit B. Particularly preferred according to the present invention are radicals of the formula (III) whose central phenylene A-linker L-phenylene B unit consists according to the present definition of an m-substituted phenylene unit A and an m-substituted phenylene unit B.

According to the present invention, the linker group L is selected from the group which consists of the elements —(CH$_2$)$_m$NHSO$_2$(CH$_2$)$_n$—, —(CH$_2$)$_m$SO$_2$NH(CH$_2$)$_n$—, —(CH$_2$)$_m$NHCO(CH$_2$)$_n$—, —(CH$_2$)$_m$CONH(CH$_2$)$_n$—, —(CH$_2$)$_m$OCH$_2$(CH$_2$)$_n$—, —(CH$_2$)$_m$CH$_2$O(CH$_2$)$_n$—, —(CH$_2$)$_n$COO(CH$_2$)$_n$—, —(CH$_2$)$_m$OOC(CH$_2$)$_n$—, —(CH$_2$)$_m$CH$_2$CO(CH$_2$)$_n$—, —(CH$_2$)$_m$COCH$_2$(CH$_2$)$_n$—, —NHCONH—, —(CH$_2$)$_m$SCH$_2$(CH$_2$)$_n$—, —(CH$_2$)$_m$CH$_2$S(CH$_2$)$_n$—, —(CH$_2$)$_m$CH$_2$SO(CH$_2$)$_n$—, —(CH$_2$)$_m$SOCH$_2$(CH$_2$)$_n$, —(CH$_2$)$_m$CH$_2$SO$_2$(CH$_2$)$_n$— or —(CH$_2$)$_m$SO$_2$CH$_2$(CH$_2$)$_n$—, where m and n each are an integer of 0 or 1 and m+n ≦ 1.

According to the invention, the linker group L is preferably —NHSO$_2$—, —CH$_2$NHSO$_2$—, —NHSO$_2$CH$_2$—, —SO$_2$NH—, —CH$_2$SO$_2$NH—, —SO$_2$NHCH$_2$—, —NHCO—, —CH$_2$NHCO—, —NH—COCH$_2$—, —CONH—, —CH$_2$CONH—, —CONHCH$_2$—, —OCH$_2$—, —CH$_2$OCH$_2$, —OCH$_2$CH$_2$—, —CH$_2$O—, —CH$_2$CH$_2$O—, —COO—, —CH$_2$COO—, —COOCH$_2$—, —OOC—, —OOCCH$_2$—, —CH$_2$OOC—, —CH$_2$CO—, —COCH$_2$—, —CH$_2$CH$_2$CO—, —COCH$_2$CH$_2$—, —CH$_2$COCH$_2$—, —NHCONH—, —SCH$_2$—, —CH$_2$S—, —CH$_2$SCH$_2$, —SCH$_2$CH$_2$—, CH$_2$CH$_2$S—, —SOCH$_2$—, —CH$_2$SO—, —CH$_2$SOCH$_2$—, —SOCH$_2$CH$_2$—, —CH$_2$CH$_2$SO—, —SO$_2$CH$_2$—, —CH$_2$SO$_2$—, —CH$_2$SO$_2$CH$_2$—, —CH$_2$CH$_2$—SO$_2$— or —SO$_2$CH$_2$CH$_2$—. Particularly preferred linker groups L here are —NHSO$_2$—, —CH$_2$NHSO$_2$—, —NHSO$_2$CH$_2$—, —SO$_2$NH—, —CH$_2$SO$_2$NH—, —SO$_2$NHCH$_2$—, —NHCO—, —CH$_2$NHCO—, —NHCOCH$_2$—, —CONH—, —CH$_2$CONH—, —CONHCH$_2$—, —OCH$_2$—, —CH$_2$OCH$_2$, —OCH$_2$CH$_2$—, —CH$_2$O— or —CH$_2$CH$_2$O—.

The central phenylene unit B carries as a substituent a radical which, if the linkage to the radical of the conjugate does not take place via this, is selected from the group consisting of a group NR$^{12}$CX'R$^{13}$S—, an amino, guanidine, urea or thiourea unit. This group NR$^{12}$CX'R$^{13}$S—, amino, guanidine, urea or thiourea unit can be either open-chain or a constituent of a cyclic system. The nitrogen atoms of the respective unit, which are optionally both present and bonded only via single bonds, can carry additional substituents R$^{12}$, R$^{14}$ and R$^{15}$. These substituents can independently of one another or simultaneously be hydrogen, a substituted or unsubstituted alkyl or cycloalkyl radical, a substituted or unsubstituted aryl radical, a saturated or unsaturated, optionally substituted heterocyclic radical or can be bonded to one another and thus, together with the nitrogen atom(s) to which they are bonded, form a heterocyclic ring system. Preferred substituents here are those which are selected from the group consisting of hydrogen, a C$_{1-6}$-alkyl such as, for example, methyl, ethyl, propyl, isopropyl, butyl, isobutyl, t-butyl, pentyl, isopentyl, neopentyl or hexyl, a C$_{3-7}$-cycloalkyl such as, for example, cyclopropyl, cyclopropylmethyl, cyclobutyl, cyclopentyl, cyclohexyl or cycloheptyl, an aryl such as, for example, phenyl, benzyl or tolyl, a heterocyclic radical such as, for example, pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, oxathiazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine and can alternatively be substituted by one or more C$_{1-6}$-alkyl radicals such as methyl, ethyl, propyl, isopropyl, butyl, isobutyl, t-butyl, pentyl, isopentyl, neopentyl or hexyl, C$_{3-7}$-cycloalkyl radicals such as cyclopropyl, cyclopropylmethyl, cyclobutyl, cyclopentyl or cyclohexyl, aryl radicals such as phenyl, benzyl, tolyl, naphthyl, indolyl, heterocyclic radicals such as pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, oxathiazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or functional groups such as a double bond to a heteroatom such as oxygen, sulphur or nitrogen, an optionally substituted amino group, a nitro group, a halogen, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. Furthermore, one or more additionally saturated or unsaturated rings can be fused to the abovementioned cyclic radicals with formation of, for example, a naphthyl, indolyl, benzofuranyl, benzoxazolyl, benzothiazolyl, benzimidazolyl, quinolinyl or isoquinolinyl unit or a partially or completely hydrogenated analogue thereof. Particularly preferred substituents are those such as hydrogen, methyl, ethyl, propyl, isopropyl, butyl, isobutyl, t-butyl, pentyl, isopentyl, neopentyl, hexyl, cyclopropyl, cyclo-propylmethyl, cyclobutyl, cyclopentyl, cyclohexyl, 4-methylcyclohexyl, 3,3,5-trimethylcyclohexyl, 5-methyl-2-hexyl, phenyl, benzyl, tolyl or a substituted derivative thereof, C$_{1-4}$-alkylamino-C$_{1-4}$-alkyl, C$_{1-4}$-dialkylamino-C$_{1-4}$-alkyl, amino-C$_{1-4}$alkyl, C$_{1-4}$-alkyloxy-C$_{1-4}$-alkyl or one of the abovementioned radicals (a1) to (a28). If the linkage of the radical of the formula (III) to the rest of the conjugate takes place via this group, the radical R$^{15}$ represents a direct bond via which the corresponding linkage between the radical of the formula (III) and the rest of the conjugate takes place.

The two radicals R$^{14}$ and R$^{15}$ or the radicals R$^{12}$ and R$^{15}$, if p in the formula (III) represents 0, can be connected to one another and thus with the nitrogen atom form a heterocyclic ring system which can be selected, for example, from the following, non-exclusive list:

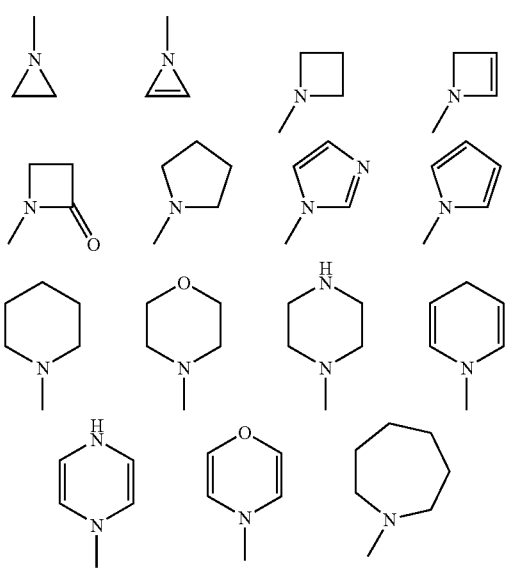

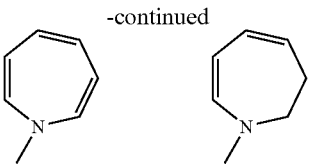

where the ring systems shown can carry one or more radicals which are selected from the group consisting of hydrogen, a $C_{1-6}$-alkyl such as, for example, methyl, ethyl, propyl, isopropyl, butyl, isobutyl, t-butyl, pentyl, isopentyl, neopentyl or hexyl, a $C_{3-7}$-cycloalkyl such as, for example, cyclopropyl, cyclopropylmethyl, cyclobutyl, cyclopentyl or cyclohexyl, an aryl such as, for example, phenyl, benzyl or tolyl, a heterocyclic radical such as, for example, pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, oxathiazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or a terminal or internal E- or Z-alkene unit, and can alternatively be substituted by one or more $C_{1-6}$-alkyl radicals such as methyl, ethyl, propyl, isopropyl, butyl, isobutyl, t-butyl, pentyl, isopentyl, neopentyl or hexyl, $C_{3-7}$-cycloalkyl radicals such as cyclopropyl, cyclopropylmethyl, cyclobutyl, cyclopentyl or cyclohexyl, aryl radicals such as phenyl, benzyl, tolyl, naphthyl, indolyl, heterocyclic radicals such as pyrrolidine, piperidine, piperazine, pyrrole, pyridine, tetrahydrofuran, furan, thiophene, tetrahydrothiophene, imida-zolidine, imidazole, oxazolidine, oxazole, thiazolidine, thiazole, oxathiazole, benz-ofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or functional groups such as a double bond to a heteroatom such as oxygen, sulphur or nitrogen, an optionally substituted amino group, a nitro group, a halogen, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. Furthermore, one or more additionally saturated or unsaturated rings can be fused to the abovementioned cyclic radicals with formation of, for example, a naphthyl, indolyl, benzofuranyl, benzoxazolyl, benzothiazolyl, benzimidazolyl, quinolinyl or isoquinolinyl unit or a partially or completely hydrogenated analogue thereof.

Of the ring systems shown above, the four- to six-membered ring systems are preferred.

As mentioned above, the group $NR^{12}CX'R^{13}S—$, the amino, urea, thiourea or guanidine unit can be open-chain or incorporated into a cyclic system and thus be a constituent of one of the following preferred functional units:

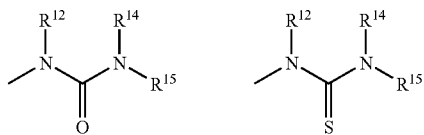

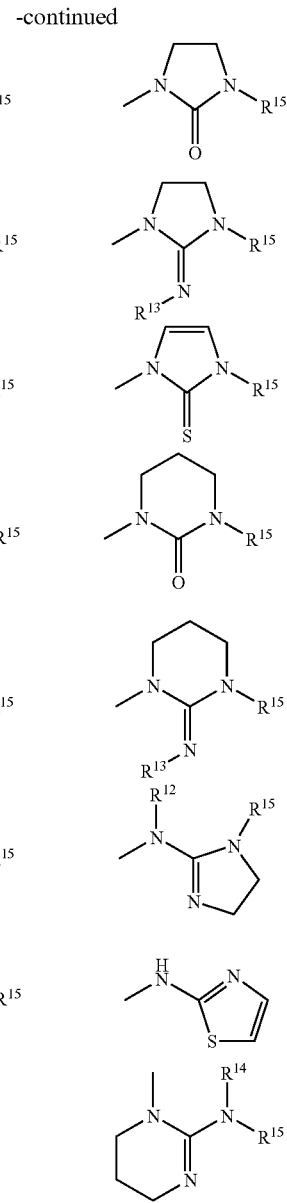

where the above list represents a non-exclusive enumeration of all possible structural units.

According to the invention, in addition to the abovementioned preferred structural units, their analogues are also included in which one or more 4- to 6-membered ring systems are fused to the heterocycle, such as, for example, the corresponding benzofused analogues of the above structural units.

In the structural units shown above, $R^{12}$, $R^{14}$ and $R^{15}$ are as defined above.

Furthermore, in the above structural units $R^{13}$ can be absent, hydrogen, a substituted or unsubstituted alkyl or cycloalkyl radical such as, for example, a $C_{1-6}$-alkyl such as methyl, ethyl, propyl, isopropyl, butyl, isobutyl, t-butyl, pentyl, isopentyl, neopentyl, hexyl or a $C_{3-7}$-cycloalkyl such as cyclopropyl, cyclobutyl, cyclopentyl, cyclohexyl, $—NO_2$, $—CN$, $—COR^{3'}$ or $—COOR^{13'}$, where $R^{13'}$ can be hydrogen, a substituted or unsubstituted alkyl or cycloalkyl radical, a substituted or unsubstituted aryl radical or a saturated or unsaturated, optionally substituted heterocyclic radical, which can be saturated or unsaturated and/or can contain further heteroatoms, and is preferably a $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclobutyl, cyclopentyl, cyclohexyl, an aryl such as, for example, phenyl, benzyl, tolyl or a substituted derivative.

According to the invention, particularly preferred radicals of the formula (III) are those in which the amino group included in the radical derived from a β-amino acid carries a radical-$SO_2R^{10'}$, where $R^{10'}$ is preferably methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —$C_6H_2(CH_3)_3$, —$C_6(CH_3)_5$, —$CH_2C_6H_2(CH_3)_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 3-aminophenyl, 4-aminophenyl, 4-chlorophenylmethyl, 2,4-dichlorophenylmethyl, 2,6-dichlorophenylmethyl, 2-methoxycarbonylphenylmethyl, 3-trifluoro-methyl-phenyl, 4-trifluoromethylphenyl, 3,5-bis(trifluoromethyl)phenyl, 4-trifluoromethoxyphenyl, phenylmethyl, 2-acetamido-4-methylthiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propyl-phenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methyl-benzothiazol-2-yl, N-methoxycarbonylpiperidin-3-yl, thiophen-2-yl, isoxazol-5-yl, ethoxy, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridin-5-methyl, 5,7-dimethyl-1,3,4-triazaindolizin-2-yl, (S)-camphan-1-yl, (R)-camphan-1-yl or 8-quinolinyl, the linker group L is —$NHSO_2$—, —$CH_2NHSO_2$—, —$NHSO_2CH_2$—, and the radical found on the phenylene unit is an open-chain or cyclic guanidine unit, a cyclic guanidine unit such as, for example, a 4,5-dihydro-1H-imidazol-2-ylamino unit being particularly preferred.

Furthermore, according to the present invention radicals of the formula (III) are particularly preferred in which the amino group included in the radical derived from a β-amino acid carries a radical-$SO_2R^{10'}$ or a radical —$COOR^{10''}$, where $R^{10'}$ or $R^{10''}$ is preferably methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —$C_6H_2(CH_3)_3$, —$C_6(CH_3)_5$, —$CH_2C_6H_2(CH_3)_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 3-aminophenyl, 4-aminophenyl, 4-chloro-phenyl-methyl, 2,4-dichlorophenylmethyl, 2,6-dichlorophenylmethyl, 2-methoxycarbonyl-phenylmethyl, 3-trifluoromethylphenyl, 4-trifluoromethylphenyl, 3,5-bis(trifluoro-methyl)phenyl, 4-trifluoromethoxyphenyl, phenylmethyl, 2-acetamido-4-methylthiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetra-methylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methyl-benzo-thiazol-2-yl, N-methoxycarbonyl-piperidin-3-yl, thiophen-2-yl, isoxazol-5-yl, ethoxy, 2-chloro-pyridin-3-yl, pyridin-3-yl, benzyloxy, 5-methylisoxazol-3-yl, 1-adamantyl, 4-chlorophenoxymethyl, 2,2-dimethylethenyl, 2-chloropyridin-5-methyl, 5,7-dimethyl-1,3,4-triazaindolizin-2-yl, (S)-camphan-1-yl, (R)-camphan-1-yl or 8-quinolinyl, the linker group L is —$NHSO_2$—, —$CH_2NHSO_2$—, —$NHSO_2CH_2$— or —$OCH_2$—, —$CH_2O$—, —$CH_2OCH_2$—, —$CH_2CH_2O$—, —$OCH_2CH_2$—, and the radical found on the phenylene unit is an open-chain or cyclic guanidine unit, a cyclic guanidine unit such as, for example, a 4,5-dihydro-1H-imidazol-2-ylamino unit being particularly preferred.

Moreover, according to the present invention radicals of the formula (III) are particularly preferred in which the amino group included in the radical derived from a β-amino acid carries a radical —$COR^{10'}$, where $R^{10'}$ is preferably hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —$C_6H_2(CH_3)_3$, —$C_6(CH_3)_5$, —$CH_2C_6H_2(CH_3)_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 3-aminophenyl, 4-aminophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methylthiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methyl-benzothiazol-2-yl, N-methoxycarbonyl-piperidin-3-yl, thiophen-2-yl, isoxazol-5-yl, ethoxy, 2-chloropyridin-3-yl, pyridin-3-yl, benzyloxy, 5-methylisoxazol-3-yl, 1-adamantyl, 4-chloro-phenoxymethyl, 2,2-dimethylethenyl, 2-chloropyridin-5-methyl, 5,7-dimethyl-1,3,4-triazaindolizin-2-yl, (S)-camphan-1-yl, (R)-camphan-1-yl or 8-quinolinyl, the linker group L is —$NHSO_2$—, —$CH_2NHSO_2$—, —$NHSO_2CH_2$—, and the radical found on the phenylene unit is an open-chain or cyclic guanidine unit, a cyclic guanidine unit such as, for example, a 4,5-dihydro-1H-imidazol-2-ylamino unit being particularly preferred.

Moreover, according to the present invention radicals of the formula (III) are particularly preferred in which the amino group included in the radical derived from a β-amino acid carries a radical —$COR^{10'}$, where $R^{10'}$ is preferably hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof, —$C_6H_2$(CH$_3$)$_3$, —$C_6$(CH$_3$)$_5$, —CH$_2$C$_6$H$_2$(CH$_3$)$_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 3-aminophenyl, 4-aminophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methylthiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methylbenzothiazol-2-yl, N-methoxycarbonyl-piperidin-3-yl, thiophen-2-yl, isoxazol-5-yl, ethoxy, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridin-5-methyl, 5,7-dimethyl-1,3,4-triazaindolizin-2-yl, (S)-camphan-1-yl, (R)-camphan-1-yl or 8-quinolinyl, the linker group L is —NHSO$_2$—, —CH$_2$NHSO$_2$—, —NHSO$_2$CH$_2$—, and the radical found on the phenylene unit is an open-chain or cyclic guanidine unit, a cyclic guanidine unit such as, for example, a 4,5-dihydro-1H-imidazol-2-ylamino unit being particularly preferred.

The moiety addressing α$_v$β$_3$ integrin receptors can furthermore be a radical of the formula (IV):

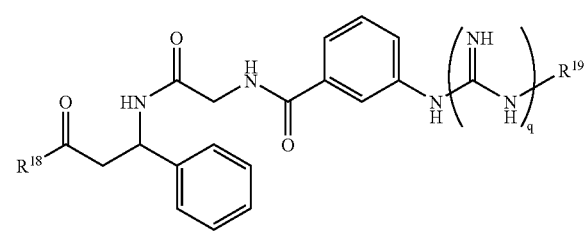

(IV)

where the radicals in the formula (IV) have the meaning defined above.

The terminal carboxyl unit can, if the linkage to the rest of the conjugate does not take place via this, be present as a free carboxylic acid or as an ester. In the case in which the terminal carboxyl unit is esterified, fundamentally all carboxylic esters obtainable by conventional processes, such as the corresponding alkyl esters, cycloalkyl esters, aryl esters and hetereocyclic analogues thereof can be used according to the invention, where alkyl esters, cycloalkyl esters and aryl esters are preferred and the alcoholic radical can carry further substituents. Particularly preferred C$_{1-6}$-alkyl esters are those such as the methyl ester, ethyl ester, propyl ester, isopropyl ester, butyl ester, isobutyl ester, t-butyl ester, pentyl ester, isopentyl ester, neopentyl ester, hexyl ester, cyclopropyl ester, cyclopropylmethyl ester, cyclobutyl ester, cyclopentyl ester, cyclohexyl ester, or aryl esters such as the phenyl ester, benzyl ester or tolyl ester.

The radicals of the formula (IV) according to the invention are preferably used in a form in which the terminal carboxyl unit is present as the free carboxylic acid.

The radicals of the formula (IV) according to the invention can contain a terminal guanidine or amino unit. The radical R$^{19}$ here can be hydrogen, a substituted or unsubstituted alkyl or cycloalkyl radical, a substituted or unsubstituted aryl radical or a saturated or unsaturated, optionally substituted heterocyclic radical. A substituent is preferred here which is selected from the group consisting of hydrogen, a C$_{1-6}$-alkyl such as, for example, methyl, ethyl, propyl, isopropyl, butyl, isobutyl, t-butyl, pentyl, isopentyl, neopentyl or hexyl, a C$_{3-7}$-cycloalkyl such as, for example, cyclopropyl, cyclopropylmethyl, cyclobutyl, cyclopentyl, cyclohexyl or cycloheptyl, an aryl such as, for example, phenyl, benzyl or tolyl, a heterocyclic radical such as, for example, pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, oxathiazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine and can alternatively be substituted by one or more C$_{1-6}$-alkyl radicals such as methyl, ethyl, propyl, isopropyl, butyl, isobutyl, t-butyl, pentyl, isopentyl, neopentyl or hexyl, C$_{3-7}$-cycloalkyl radicals such as cyclopropyl, cyclopropylmethyl, cyclobutyl, cyclopentyl or cyclohexyl, aryl radicals such as phenyl, benzyl, tolyl, naphthyl, indolyl, heterocyclic radicals such as pyrrolidine, piperidine, piperazine, pyrrole, pyridine, tetrahydrofuran, furan, thiophene, tetrahydrothiophene, imidazolidine, imidazole, oxazolidine, oxazole, thiazolidine, thiazole, oxathiazole, benzofuran, benzoxazole, benzothiazole, benzimidazole, quinoline, isoquinoline, tetrahydroquinoline, tetrahydroisoquinoline, triazole, tetrazole, pyrimidine, purine, cytosine, thymine, uracil, adenine, guanine or xanthine, or functional groups such as a double bond to a heteroatom such as oxygen, sulphur or nitrogen, an optionally substituted amino group, a nitro group, a halogen, a hydroxyl group, an ether group, a sulphide group, a mercaptan group, a cyano group, an isonitrile group, an alkenyl group, an alkinyl group, an aldehyde group, a keto group, a carboxyl group, an ester group, an amide group, a sulphoxide group or a sulphone group. Furthermore, one or more additionally saturated or unsaturated rings can be fused to the abovementioned cyclic radicals with formation of, for example, a naphthyl, indolyl, benzofuranyl, benzoxazolyl, benzothiazolyl, benzimidazolyl, quinolinyl or isoquinolinyl unit or a partially or completely hydrogenated analogue thereof. Particularly preferred substituents are those such as hydrogen, methyl, ethyl, propyl, isopropyl, butyl, isobutyl, t-butyl, pentyl, isopentyl, neopentyl, hexyl, cyclopropyl, cyclo-propyl-methyl, cyclobutyl, cyclopentyl, cyclohexyl, 4-methylcyclohexyl, 3,3,5-trimeth-ylcyclohexyl, 5-methyl-2-hexyl, phenyl, benzyl, tolyl or a substituted derivative thereof, C$_{1-4}$-alkylamino-C$_{1-4}$-alkyl, C$_{1-4}$-dialkylamino-C$_{1-4}$-alkyl, amino-C$_{1-4}$alkyl, C$_{1-4}$-alkyloxy-C$_{1-4}$-alkyl or one of the abovementioned radicals (a1) to (a28). If the linkage of the radical of the formula (IV) to the rest of the conjugate takes place via this group, the radical R$^{17}$ represents a direct bond, via which the corresponding linkage between the radical of the formula (IV) and the rest of the conjugate takes place.

The novel conjugates according to claim 1 can be prepared by linkage of the toxophore to the linking unit and subsequent linkage to the moiety addressing $\alpha_v\beta_3$ integrin receptors. However, it is also possible to first connect the moiety addressing $\alpha_v\beta_3$ integrin receptors to the linking unit and then to bind the toxophore to the linking unit.

The combination of the individual units of the conjugates according to the invention can preferably be carried out by means of functional groups which can be reacted with one another and, as a result, can be linked by conventional processes known to the person skilled in the art. For example carboxyl functions can be reacted with amino functions with formation of an amide bond. It is also possible to synthesize the linking unit stepwise on one of the two radicals to be connected, i.e. the toxophore or the moiety addressing $\alpha_v\beta_3$ integrin receptors, by conventional processes known to the person skilled in the art and then to link the finished linking unit to the radical which is still to be bound.

The present invention in particular relates to a process for the preparation of conjugates according to formula (1), comprising

[A] the reaction of a compound from the group of compounds of the formulae (II), (III) and (IV), which has a free or optionally activated carboxyl function, with a compound of the formula (Ia) which has a free primary or secondary amino group CT-AA1-AA2-AA3-AA4-Sp  (Ia)

in which all radicals have the meaning indicated in claim 5,
in the presence of a base;

or

[B] the reaction of a compound from the group of compounds of the formulae (II), (III) and (IV), which has a free primary or secondary amino function, with a carbonic acid derivative such as, for example, phosgene, thiophosgene or a chloroformic acid ester, if appropriate in the presence of a base, followed by the reaction with a compound of the formula (Ia) which has a free primary or secondary amino group CT-AA1-AA2-AA3-AA4-Sp  (Ia)

in which all radicals have the meaning indicated in claim 5,
and
if appropriate the removal of protective groups and/or derivatization of nitrogen atoms present at preferred points of time in the preparation process and/or conversion of the compound obtained into the free acid and/or conversion of the compound obtained into one of its physiological salts by reaction with an inorganic or organic base or acid;

or

[C] the reaction of a cytotoxic compound or of a cytostatic or of a cytostatic derivative CT which contains a free primary or secondary amino group, with a carbonic acid derivative such as, for example, phosgene, thiophosgene or a chloroformic acid ester in the presence of a base, followed by the reaction with a compound from the group of compounds of the formulae (II), (III) and (IV), which has a free primary or secondary amino function, and
if appropriate the removal of protective groups and/or derivatization of nitrogen atoms present at preferred points of time in the preparation process and/or conversion of the compound obtained into the free acid and/or conversion of the compound obtained into one of its physiological salts by reaction with an inorganic or organic base or acid;

or

[D] the reaction of a compound from the group of compounds of the formulae (II), (III) and (IV), which contains a free primary or secondary amino function, with a compound of the formula (Ia) which contains a free or optionally activated carboxyl function CT-AA1-AA2-AA3-AA4-Sp  (Ia)

in which all radicals have the meaning indicated in claim 5,
in the presence of a base;
and
if appropriate the removal of protective groups and/or derivatization of nitrogen atoms present at preferred points in time in the preparation process and/or conversion of the compound obtained into the free acid and/or conversion of the compound obtained into one of its physiological salts by reaction with an inorganic or organic base or acid.

According to a preferred embodiment, all steps of the preparation process are carried out on a solid phase.

In variant [A] of the preparation process according to the invention, a moiety addressing $\alpha_v\beta_3$ integrin receptors from the group of radicals of the formulae (II), (III) or (IV) is linked via its free carboxyl function to the amino function of a toxophore-linking unit conjugate (Ia) with formation of an amide bond. This reaction can be carried out by conventional methods known to the person skilled in the art (cf., for example, J. March, Advanced organic chemistry, $3^{rd}$ ed., Wiley, p. 370 ff.). It is preferred according to the invention to activate the carboxyl function of the moiety addressing $\alpha_v\beta_3$ integrin receptors and then to react with the compound (Ia) in an organic solvent in the presence of a base.

For the activation of the carboxyl group, the coupling reagents known in peptide chemistry can be used, such as are described, for example, in Jakubke/Jeschkeit: Aminosäuren, Peptide, Proteine [Amino acids, Peptides, Proteins]; Verlag Chemie 1982 or Tetrahedr. Lett. 34, 6705 (1993). Examples mentioned are N-carboxylic acid anhydrides, acid chlorides or mixed anhydrides, adducts with carbodiimides, e.g. N,N'-diethyl-, N,N'-diisopropyl- or N,N'-dicyclohexyl-carbodiimide, N-(3-dimethylaminopropyl)N'-ethyl-carbodiimide hydrochloride, N-cyclohexyl-N'-(2-morpholinoethyl)-carbodiimide metho-p-toluenesulphonate, or carbonyl compounds such as carbonyldiimidazole, or 1,2-oxazolium compounds such as 2-ethyl-5-phenyl-1,2-oxazolium-3-sulphate or 2-tert-butyl-5-methyl-isoxazolium perchlorate, or acylamino compounds such as 2-ethoxy-1-ethoxycarbonyl-1,2-dihydroquinoline or propane-phosphonic anhydride or isobutyl chloroformate or benzotriazolyloxy-tris-(dimethylamino)-phosphonium hexafluorophosphate, 1-hydroxybenzotriazole or N-hydroxysuccinimide esters. It is furthermore proposed to employ the acid components in the form of a Leuchs' anhydride.

Variant [A] of the above preparation process according to the invention can be carried out under various pressure and temperature conditions, for example 0.5 to 2 bar and preferably under normal pressure, or −30 to +100° C. and preferably −10 to +80° C., in suitable solvents such as dimethylformamide (DMF), tetrahydrofuran (THF), dichloromethane, chloroform, lower alcohols, acetonitrile, dioxane, water or in mixtures of the solvents mentioned. As a rule, reaction in DMF, dichloromethane, THF, dioxane/ water or THF/dichloromethane at room temperature or with ice-cooling and under normal pressure is preferred.

Bases which can be employed in variant [A] of the preparation process according to the invention are, for example, triethylamine, ethyl-diisopropylamine, pyridine, N,N-dimethylaminopyridine or other bases conventionally used in steps of this type such as, for example, Hünig's base.

In variant [B] of the process according to the invention, a moiety addressing $\alpha_v\beta_3$ integrin receptors from the group of radicals of the formulae (II), (III) and (IV) is reacted via its free amino function first with a carbonic acid derivative with formation of a corresponding isocyanate, isothiocyanate or carbamate, which is then linked to the amino function of a toxophore-linking unit conjugate (Ia) with formation of the conjugate (I).

The reaction of the moiety addressing $\alpha_v\beta_3$ integrin receptors from the group of radicals of the formulae (II), (III) or (IV) via its free amino function with a carbonic acid derivative can be carried out by conventional methods known to the person skilled in the art (cf., for example, J. March, Advanced organic chemistry, $3^{rd}$ ed., Wiley, p. 370 ff.). According to the invention, the reaction is preferably carried out with phosgene or a substitute for phosgene such as, for example, trichloromethyl chloroformate, thiophosgene or a chloroformic acid ester in a solvent such as dimethylformamide (DMF) or a mixture of dioxane and water (1:1) or of tetrahydrofuran (THF) and dichloromethane (DCM) (1:1) at room temperature or with cooling, preferably at room temperature, and stirring for approximately 10 minutes up to approximately 3 hours, if appropriate in the presence of a base.

The subsequent reaction of the isocyanate, isothiocyanate or carbamate thus obtained with the amino function of a toxophore-linking unit conjugate (Ia) with formation of a corresponding thiourea or urea bond can be carried out by conventional methods known to the person skilled in the art (cf., for example, J. March, Advanced organic chemistry, $3^{rd}$ ed., Wiley, p. 802 ff.).

According to the invention, the carbamate or thiocyanate or isothiocyanate is preferably reacted with the amino function of the compound (Ia) at room temperature with stirring for approximately 1 to 5 hours, preferably approximately 2 to 3 hours, in the presence of a base in a solvent such as dimethylformamide (DMF).

Bases which can be employed in variant [B] of the preparation process according to the invention are, for example, triethylamine, ethyldiisopropylamine, pyridine, N,N-dimethylaminopyridine or other bases conventionally used in steps of this type, such as, for example, Hünig's base.

In variant [C] of the process according to the invention, an amino function of a cytotoxic compound or of a cytostatic or of a cytostatic derivative CT is first reacted with a carbonic acid derivative with formation of a corresponding isocyanate, isothiocyanate or carbamate, which is then reacted with an amino function of a moiety addressing $\alpha_v\beta_3$ integrin receptors from the group of radicals of the formulae (II), (III) and (IV) with formation of the conjugate (1).

The reaction of the amino function of a cytotoxic compound or of a cytostatic or of a cytostatic derivative CT with a carbonic acid derivative can be carried out by conventional methods known to the person skilled in the art (cf., for example, J. March, Advanced organic chemistry, $3^{rd}$ ed., Wiley, p. 370 ff.). According to the invention, the reaction with phosgene or a substitute for phosgene such as, for example, trichloromethyl chloroformate, thiophosgene or a chloroformic acid ester is preferably carried out in a solvent such as dimethylformamide (DMF) or a mixture of dioxane and water (1:1) or of tetrahydrofuran (THF) and dichloromethane (DCM) (1:1) at room temperature or with cooling, preferably at room temperature, and stirring for approximately 10 minutes up to approximately 3 hours, if appropriate in the presence of a base.

The subsequent reaction of the isocyanate, isothiocyanate or carbamate thus obtained with the amino function of a moiety addressing $\alpha_v\beta_3$ integrin receptors from the group of radicals of the formulae (II), (III) and (IV) with formation of a corresponding thiourea or urea bond can be carried out by conventional methods known to the person skilled in the art (cf., for example, J. March, Advanced organic chemistry, $3^{rd}$ ed., Wiley, p. 802 ff.).

According to the invention, the carbamate or thiocyanate or isothiocyanate is preferably reacted with the amino function of a moiety addressing $\alpha_v\beta_3$ integrin receptors from the group of radicals of the formulae (H), (III) and (IV) at room temperature with stirring for approximately 1 to 5 hours, preferably approximately 2 to 3 hours, in the presence of a base in a solvent such as dimethylformamide (DMF).

Bases which can be employed in variant [C] of the preparation process according to the invention are, for example, triethylamine, ethyldiisopropylamine, pyridine, N,N-dimethylaminopyridine or other bases conventionally used in steps of this type, such as, for example, Hünig's base.

In variant [D] of the preparation process according to the invention, a moiety addressing $\alpha_v\beta_3$ integrin receptors from the group of radicals of the formulae (II), (III) and (IV) is linked via its free amino function to the carboxyl function of a toxophore-linking unit conjugate (Ia) with formation of an amide bond. This reaction can be carried out by conventional methods known to the person skilled in the art (cf., for example, J. March, Advanced organic chemistry, $3^{rd}$ ed., Wiley, p. 370 ff.). It is preferred according to the invention to activate the carboxyl function of the compound (Ia) and then to react it with a moiety addressing $\alpha_v\beta_3$ integrin receptors from the group of radicals of the formulae (II), (III) and (IV) in an organic solvent in the presence of a base.

For activation of the carboxyl group, the coupling reagents known in peptide chemistry can be used, such as are described, for example, in Jakubke/Jeschkeit: Aminosäuren, Peptide, Proteine [Amino acids, Peptides, Proteins]; Verlag Chemie 1982 or Tetrahedr. Lett. 34, 6705 (1993). Examples mentioned are N-carboxylic anhydrides, acid chlorides or mixed anhydrides, adducts with carbodiimides, e.g. N,N'-diethyl-, N,N'-diisopropyl- or N,N'-dicyclohexylcarbodiimide, N-(3-dimethyl-aminopropyl)-N'-ethyl-carbodiimide hydrochloride, N-cyclohexyl-N'-(2-morpholinoethyl)-carbodiimide metho-p-toluenesulphonate, or carbonyl compounds such as carbonyldiimidazole, or 1,2-oxazolium compounds such as 2-ethyl-5-phenyl-1,2-oxazolium-3-sulphate or 2-tert-butyl-5-methyl-isoxazolium perchlorate, or acylamino compounds such as 2-ethoxy-1-ethoxycarbonyl-1,2-dihydroquinoline, or propane-phosphonic anhydride, or isobutyl chloroformate, or benzotriazolyloxy-tris-(dimethylamino)-phosphonium hexafluorophosphate, 1-hydroxybenzotriazole or N-hydroxysuccinimide esters. It is furthermore proposed to employ the acid components in the form of a Leuchs' anhydride.

Variant [D] of the above preparation process according to the invention can be carried out under various pressure and temperature conditions, for example 0.5 to 2 bar and preferably under normal pressure, or –30 to +100° C. and preferably –10 to +80° C., in suitable solvents such as dimethylformamide (DMF), tetrahydrofuran (THF), dichloromethane, chloroform, lower alcohols, acetonitrile, dioxane, water or in mixtures of the solvents mentioned. As a rule, reaction in DMF, dichloromethane, THF, dioxane/water or THF/dichloromethane at room temperature or with ice-cooling and at normal pressure is preferred.

Bases which can be employed in variant [D] of the preparation process according to the invention are, for example, triethylamine, ethyldiisopropylamine, pyridine, N,N-dimethylaminopyridine or other bases conventionally used in steps of this type such as, for example, Hünig's base.

The compounds obtained according to the process explained above can furthermore be derivatized by removal of protective groups which may be present, further substitution of nitrogen atoms present at preferred positions in the preparation process and/or conversion of the compound obtained into the free acid and/or its physiologically acceptable salts. By way of example, the t-butoxymethoxycarbonyl groups conventionally used as protective groups for nitrogen atoms are removed in acidic medium, for example by addition of trifluoroacetic acid. Suitable alkylating agents for the derivatization of nitrogen atoms in this step are reagents conventionally used for this purpose, using which, for example, a substituted or unsubstituted alkyl or cycloalkyl radical, a substituted or unsubstituted aryl radical or a saturated or unsaturated, optionally substituted heterocyclic radical can be bonded to the appropriate nitrogen atom. With respect to the substituents preferably bonded to the respective nitrogen atoms, reference is made to the above description of the compounds according to the invention. The above reactions and their implementation are well known to the person skilled in the art and are described in detail in standard works such as, for example, Houben-Weyl, Methoden der organischen Chemie [Methods of Organic Chemistry], Georg Thieme Verlag, Stuttgart.

The ester derivatives according to the invention can be converted into the corresponding free carboxylic acids in a conventional manner, such as, for example, by basic ester hydrolysis.

If desired, the compounds according to the invention can be converted into their physiologically acceptable salts. This can be carried out either by reaction with an organic or inorganic base such as, for example, an alkali metal hydroxide or alkaline earth metal hydroxide such as KOH, NaOH, LiOH, $Mg(OH)_2$ or $Ca(OH)_2$, as a result of which the terminal carboxyl group is deprotonated and the corresponding carboxylate is formed, or by reaction with an organic or inorganic acid such as, for example, hydrochloric acid, sulphuric acid, phosphoric acid, mandelic acid, oleic acid, linoleic acid or p-toluenesulphonic acid, as a result of which one or more of the nitrogen atoms present are protonated.

The compounds of the formula (Ia) serving as starting substances can be prepared by conventional methods. The linkage of the toxophore to amino acid units can be carried out by conventional methods of peptide chemistry (cf., for example, Jakubke/Jeschkeit: Aminosäuren, Peptide, Proteine [Amino acids, Peptides, Proteins]; Verlag Chemie 1982, Houben-Weyl, Methoden der Organischen Chemie [Methods of Organic Chemistry], Georg Thieme Verlag Stuttgart, Fourth Edition; Volume 15.1 and 15.2, edited by E. Wünsch) and is also described, for example, in WO 96/31532 and WO 98/51703, whose contents are inserted here by means of reference.

If appropriate, a spacer unit Sp should be bonded to an appropriate toxophore-amino acid conjugate or a toxophore or a side-chain modification of amino acids which can be present should be carried out by bonding of a spacer unit Sp'. Possible spacer units Sp according to the present invention are an arylaminocarbonyl or an arylaminothiocarbonyl radical having 7–11 carbon atoms or an alkanedicarboxylic acid radical having 3 to 8 carbon atoms or a carbonyl or a thiocarbonyl radical. Possible side-chain radicals Sp' according to the present invention are an arylaminocarbonyl or an arylaminothiocarbonyl radical having 7–11 carbon atoms.

The bonding of the appropriate arylaminocarbonyl or arylaminothiocarbonyl radicals can be carried out as described above by reaction of the toxophore or of the toxophore-amino acid conjugate with an appropriate aryl isocyanate or aryl isothiocyanate. Reactions of this type are also described, for example, in WO 96/31532.

The bonding of the appropriate carbonyl or thiocarbonyl radicals can be carried out as described above by reaction of the toxophore or of the toxophore-amino acid conjugate with phosgene or a substitute for phosgene such as, for example, trichloromethyl chloroformate or thiophosgene.

The bonding of the appropriate alkanedicarboxylic acid radicals can be carried out by conventional methods known to the person skilled in the art, such as are described, for example, in Houben-Weyl, Methoden der Organischen Chemie [Methods of Organic Chemistry], Georg Thieme Verlag Stuttgart, fourth edition; Volume 15.1 and 15.2, edited by E. Wünsch. For example, free amino functions of the toxophore or of the toxophore-amino acid conjugate can be reacted with appropriate alkanedicarboxylic acids optionally activated as described above or alkanedicarboxylic anhydrides such as succinic or glutaric anhydride in the presence of a base in a solvent such as dichloromethane.

Bases which can be employed here are, for example, triethylamine, ethyldiisopropylamine, pyridine, N,N-dimethylaminopyridine or other bases conventionally used in steps of this type such as, for example, Hünig's base.

Although according to the invention it is preferred to first synthesize the toxophore-linking unit conjugate (Ia), it is also possible, of course, to build up the linking unit in series first on the moiety addressing $\alpha_v\beta_3$ integrin receptors or to bond it as a whole and then to connect the conjugate thus obtained to the toxophore.

According to a preferred embodiment of the present invention, the synthesis of the compounds according to the invention is carried out on a solid phase such as a polystyrene resin, particularly preferably a commercially available Wang polystyrene resin. The resin is in this case first swollen in a solvent such as dimethylformamide (DMF). The moiety of the formula (II), (III) or (IV) addressing $_{v\ 3}$ integrin receptors is then bonded to the resin via its carboxyl function by standard processes. For example, the bonding of the carboxylic acid to the resin can be carried out in the presence of a base such as pyridine and a reagent activating the carboxyl unit, such as an acid halide, for example dichlorobenzoyl chloride, in a solvent such as dimethylformamide (DMF). However, other reagents conventionally used for this purpose can also be employed. The reaction mixture is stirred at room temperature and normal pressure for at least 2 hours, preferably 12 hours, particularly preferably approximately 24 hours, the carboxylic acid being employed in an excess with respect to the loading of the solid phase, preferably in a two- to three-fold excess. All reactions described herein can then be carried out on the moiety of the formula (II), (III) or (IV) bound to the resin and addressing $\alpha_v\beta_3$ integrin receptors, as described here.

According to a preferred embodiment of the present invention, the toxophore is camptothecin or a camptothecin derivative such as 9-aminocamptothecin. The linkage of these toxophores to the linking unit can be carried out via the C20 OH group or, in the case of 9-aminocamptothecin, via the free amino group.

The camptothecin unit used as a starting compound can be present in the 20(R) or in the 20(S) configuration or as a mixture of these two stereoisomeric forms. The 20(S) configuration is preferred.

After linkage of the first amino acid to camptothecin, diastereomer mixtures can be formed. Pure diastereomers of the compounds according to the invention can be prepared by the processes indicated above, for example, by separating the diastereomers in a suitable manner after coupling of the first amino acid unit to the camptothecin and subsequent protective group removal.

The radical of the formula (II) addressing $\alpha_v\beta_3$ integrin receptors can be prepared from commercially obtainable starting compounds by the following steps:

a) reaction of a carboxylic acid derivative of the formula (IIa)

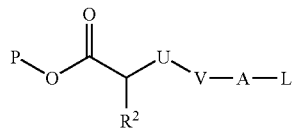

(IIa)

where

P is a conventional protective group, a solid phase conventionally used for carrying out a solid-phase reaction or $R^1$ as defined above;

A is a phenylene group optionally containing additional radicals, which is 1,3- or 1,4-substituted with respect to V and L;

L is —H, —F, —Cl, —Br, —I, —SCN, —$N_2^+$ or an organometallic radical;

and the other radicals are as defined above;

with a phenyl compound of the formula (IIb)

M-B-W-D          (IIb)

where

M is —H, —I, —$N_2^+$, —COOOCOBNO$_2$ or an organometallic radical;

B is a phenylene group optionally containing additional radicals, which is 1,3- or 1,4-substituted with respect to M and W-D;

W is as defined in claim 1;

D is —NO$_2$, —NH$_2$ or —CHO;

to give a biphenyl compound of the formula (IIc)

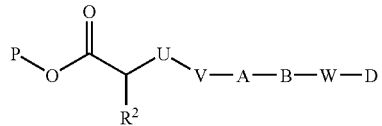

(IIc)

where the radicals are as defined above;

b) conversion of the radical D into the corresponding amino group, if D is not —NH$_2$; and c) if appropriate, derivatization of nitrogen atoms present at preferred points of time in the preparation process and/or the conversion of the compound obtained into the free acid and/or the conversion of the compound obtained to one of its physiological salts by reaction with an inorganic or organic base or acid.

According to a preferred embodiment, in the process according to the invention all steps are carried out during the binding of the carboxylic acid derivative of the formula (IIa) to a solid phase.

Furthermore, according to an embodiment of the process which is preferred according to the invention, a carboxylic acid derivative of the formula (IIa), in which L is —F, —Cl, —Br or —I and the other radicals are as defined above, is reacted with a phenyl compound of the formula (IIb), in which M is an organometallic radical;

and the other radicals are as defined above, in the presence of a palladium(II) compound and of triphenylphosphane.

Preferably, in the above process according to the invention a carboxylic acid derivative of the formula (IIa) is employed which contains a sulphonamide or carbamate group which was formed by reaction of an amino group of the corresponding precursor of the carboxylic acid derivative of the formula (IIa) with a sulphonyl halide or a carbamoyl halide.

It is furthermore preferred that in the above process according to the invention in the case in which the compound of the formula (IIc) D is equal to —NO$_2$, the conversion of D into an amino group is carried out in the presence of a Tin(II) compound.

It is furthermore preferred that in the above process according to the invention in the case in which the compound of the formula (IIc) D is equal to —CHO, the conversion of D into an amino group is carried out by reaction of an amine under reducing conditions.

It is moreover preferred that the compound of the formula (IIc) in which D is an amino group is converted, by a reaction of this amino group with a carbonic acid derivative or thiocarbonic acid derivative and a reaction following this with an amine of the formula NHR$^4$R$^6$, into a urea or thiourea unit, where R$^4$ and R$^6$ are as defined above.

The essential steps of the preparation process for the radical of the formula (II) are the reaction of a carboxylic acid, whose carboxyl group is protected and which has at least one aryl group provided with a radical accessible to an aryl—aryl coupling reaction, with a phenyl compound having at least one radical accessible to an aryl—aryl coupling reaction, which furthermore has a radical D which is an amino group or can be converted into an amino group in a simple manner, and the conversion of the radical D into the corresponding amino group, if it is not already an amino group. Further process steps which can be included are the derivatization of nitrogen atoms present in the molecule at preferred points in time in the preparation process and/or the conversion of the compound thus obtained into the free acid and/or the conversion of the compound thus obtained into one of its physiologically acceptable salts by reaction with an inorganic or organic acid or base.

The carboxylic acids to be employed as starting compounds are either commercially accessible or accessible in a simple manner by chemical standard processes, such as are known to any person skilled in the art and are described in standard works such as Houben-Weyl, Methoden der organischen Chemie [Methods of Organic Chemistry], Georg Thieme-Verlag, Stuttgart.

According to a preferred embodiment, the process for the preparation of radicals of the formula (II) starts from the following carboxylic acid derivatives:

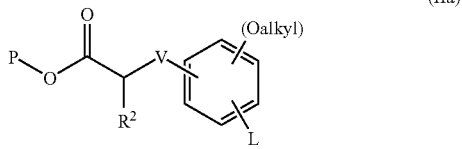

For the preparation process, the carboxyl group is in this case blocked by a conventional protective group P. Protective groups of this type are known to the person skilled in the art and do not have to be expressly mentioned here. The carboxyl group is particularly preferably esterified, P being a $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclo-propyl-methyl, cyclobutyl, cyclopentyl, cyclohexyl, an aryl such as, for example, phenyl, benzyl or tolyl or a substituted derivative thereof. Particularly preferably, however, the preparation process for the radicals of the formula (II) is carried out on a solid phase in order to achieve an implementation of the process which is as economical as possible. In this case, the carboxyl radical can be connected to any solid phase conventionally used for reactions of this type. According to the invention, a solid phase particularly preferably used is a polystyrene resin and, in particular, a commercially obtainable Wang polystyrene resin.

According to the present preferred embodiment, $R^2$ can be as described above and V can be an optionally substituted $C_{1-5}$-alkylene group. Thus the starting compounds of this preferred embodiment can be interpreted as derivatives of propanoic acid, butanoic acid, pentanoic acid, hexanoic acid or heptanoic acid. In the α-position to the carboxyl group, these carboxylic acid derivatives can have a substituent such as, for example, hydrogen, a $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclobutyl, cyclopentyl, cyclohexyl, an aryl such as, for example, phenyl, benzyl or tolyl or a substituted derivative thereof, an optionally substituted alkenyl radical, an optionally substituted alkinyl radical, —$NR^{2'}SO_2R^{2'}$, —$NR^{2'}COOR^{2'}$, —$NR^{2'}COR^{2''}$, —$NR^{2'}CONR^{2'}_2$ or —$NR^2$ $CSNR^{2'}_2$. The alkyl and cycloalkyl radicals and the benzyl radical can be introduced, for example, by reaction of the ester of the starting compounds with the appropriate alkyl, cycloalkyl or benzyl halides in basic medium if the corresponding derivatives are not commercially obtainable. The alkinyl radical can be introduced, for example, by reaction of the α-bromo ester of the present starting compound, which is accessible via the Reformatski reaction, with an appropriate acetylide anion. In the case of the phenyl radical, of the alkenyl radical and of the nitrogen-containing substituents, the corresponding α-phenyl- or α-aminocarboxylic acid derivatives are preferably used as starting materials and, if necessary, the other substituents on the α-C atom relative to the terminal carboxyl group are introduced by means of the corresponding alkyl halide. The above reactions and their implementation are well known to the person skilled in the art and are described in detail in standard works such as, for example, Houben-Weyl, Methoden der organischen Chemie [Methods of Organic Chemistry], Georg Thieme Verlag, Stuttgart.

For the introduction of a substituent in the β-position relative to the carboxyl group, it suggests itself, for example, to start from the corresponding α,β-unsaturated carboxylic acid derivatives and to react these with the respective alkyl, cycloalkyl or aryl cuprates in the sense of a Michael addition. It is then possible, if desired, to additionally introduce a substituent in the α-position relative to the carboxyl group as described above. These reactions and their implementation are also well known to the person skilled in the art and are described in detail in standard works such as, for example, Houben-Weyl, Methoden der organischen Chemie [Methods of Organic Chemistry], Georg Thieme Verlag, Stuttgart.

The radicals —$NR^{2'}SO_2R^{2'}$, —$NR^{2'}COOR^{2''}$, $NR^{2'}COR^{2'}$, —$NR^{2'}CONR^{2'}_2$ or —$NR^{2'}CSNR^{2'}_2$ preferably found in the α- or β-position relative to the carboxyl group are preferably prepared from the respective α- or β-amino acid. The α-amino acids used according to the invention are commercially obtainable, for example, from Novabiochem or Bachem. The β-amino acids can in some cases also be obtained from these companies or can be prepared according to the procedures of T. B. Johnson, Journal of the American Chemical Society, 1936, 58, or of V. A. Soloshonok, Tetrahedron Assymetry, 1995, 1601. These amino acids can be converted into the desired carboxyl-protected amino acid derivative, for example by protection of the amino group, subsequent protection of the carboxylic acid unit and subsequent deprotection of the amino group. Protective groups which can be used here for the amino group are all groups known for this purpose. Particularly preferred according to the invention is the use of a 9-fluorenylmethoxycarbonyl group (FMOC) as a protective group for the amino unit. The carboxylic acid group is protected or derivatized as described above. The carboxyl-protected α- or β-amino acids accessible in this way are reacted with a, suitable sulphonating, carbamoylating or acylating reagent in order to obtain the corresponding sulphonamide, carbamate or amide derivatives. A sulphonating reagent used is preferably a sulphonyl chloride of the formula $R^{2''}$-$SO_2Cl$ or a carbamoyl chloride of the formula $R^{2''}$-$OCOCl$, where $R^{2''}$ is a $C_{1-0}$-alkyl such as methyl, ethyl, propyl, isopropyl, butyl, isobutyl, t-butyl, pentyl, isopentyl, neopentyl, hexyl, heptyl, octyl, nonyl, decyl, cyclopropyl, cyclobutyl, cyclopentyl, cyclohexyl, or camphor-10-yl, an aryl such as phenyl, benzyl, tolyl, mesityl or substituted derivatives of these such as 2-chlorophenyl, 4-chlorophenyl, 2,5-dichlorophenyl, 4-trifluoromethylphenyl, 4-methoxyphenyl, 4-t-butylphenyl, 2,5-dimethylphenyl, 3-chlorophenyl, 3-aminophenyl, 4-aminophenyl, 2-methoxy-5-methylphenyl, 2,3,5,6-tetramethylphenyl, 2,3-dichlorophenyl, 2,6-dichlorophenyl, 2-naphthyl, 3-trifluoromethylphenyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline or 8-quinolinyl, or a heterocyclic analogue of the abovementioned cyclic radicals. Particularly preferably, $R^{2''}$ is a mesityl radical, a benzyl radical, a 2-chlorophenyl radical, a 4-chlorophenyl radical, a 2,5-dichlorophenyl radical, a 3-aminophenyl radical, a 4-aminophenyl radical, a 4-trifluoromethylphenyl radical or a camphor-10-yl radical. Instead of the abovementioned sulphonyl or carbamoyl chlorides, it is also possible to employ the corresponding fluorides, bromides or iodides. As acylating reagents, the appropriate carboxylic acid halides or carboxylic anhydrides are reacted with the amino group, the corresponding $C_{1-6}$-alkylcarbonyl chlorides such as the methyl-, ethyl-, propyl-, isopropyl-, butyl-, isobutyl-, t-butyl-, pentyl-, isopentyl-, neopentyl-, hexyl-, $C_{3-7}$-cycloalkyl- such as cyclopropyl-, cyclobutyl-, cyclopentyl-, cyclohexyl-, aryl- such as phenyl-, benzyl- or tolylcarboxylic acid chlorides or substituted derivatives thereof being preferred according to the invention. For the preparation of the urea or thiourea radicals, the amino group is preferably first reacted with a carbonic acid or thiocarbonic acid derivative such as a chloroformic acid ester or thiophosgene and then with a suitable amine $NHR^{2'}_2$. The above reactions and their implementation are well known to the person skilled in the art and are described in detail in standard works such as, for example, Houben-Weyl, Methoden der organischen Chemie [Methods of Organic Chemistry], Georg Thieme Verlag, Stuttgart.

The starting compounds to be employed according to the above preferred embodiment have a terminal phenyl unit which must carry at least one substituent L. This substituent L must be substitutable by another phenyl group by means of one of the known aryl—aryl coupling processes. According to the present invention, L can be equal to —H, —F, —Cl, —Br, —I, —SCN, —$N_2^+$ or an organometallic radical. Preferred organometallic radicals which may be mentioned are, for example, a magnesium, copper, boron, tin, lithium or lithium cuprate radical.

In addition to the radicals V and L, the terminal phenyl unit can have one or more further substituents, preferably one or more alkoxy radicals, particularly preferably one or more methoxy radicals.

If the appropriate starting compounds are not commercially obtainable, the terminal phenyl unit can be connected to the appropriate carboxylic acid derivative by standard processes such as, for example, a Friedel-Crafts alkylation, Friedel-Crafts acylation or by organometallic synthesis processes such as, for example, a palladium-assisted coupling, which are optionally followed by further derivatization steps which are known to the person skilled in the art and are described in detail in standard works such as, for example, Houben-Weyl, Methoden der organischen Chemie [Methods of Organic Chemistry], Georg Thieme Verlag, Stuttgart.

With respect to the radicals V and L, the terminal phenyl unit can be 1,3- or 1,4-substituted. Each of these isomers is, if not commercially obtainable, accessible in the manner known to the person skilled in the art.

According to a further preferred embodiment, the process for the preparation of compounds of the formula (II) starts from the following carboxylic acid derivatives:

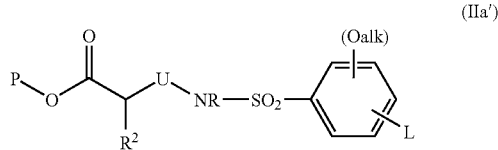

(IIa')

In this case, P and $R^2$ are as described above and can be introduced in the manner explained above if they are not already contained in the commercial starting compound. U represents an optionally substituted alkylene group and preferably an optionally substituted $C_{1-3}$-alkylene group. With respect to the possible substituents on U, reference is made to the above explanations for the compounds according to the invention.

In the case in which U is an optionally substituted methylene group, the preparation of the compound shown above starts from the optionally additionally substituted 3-aminopropanoic acid and this is reacted with an arylsulphonyl halide, preferably an arylsulphonyl chloride. The arylsulphonyl chloride is selected according to the desired presence and position of the radicals L and Oalk, L having the same meaning as described above and Oalk representing one or more alkoxy radicals, preferably one or more methoxy radicals. The preferred aryl sulphonyl halides are commercially obtainable or can be prepared by standard reactions familiar to the person skilled in the art. The above reactions and their implementation are well known to the person skilled in the art and described in detail in standard works such as, for example, Houben-Weyl, Methoden der organischen Chemie [Methods of Organic Chemistry], Georg Thieme Verlag, Stuttgart.

The biphenyl nucleus is produced in all embodiments according to the invention by an aryl—aryl coupling. Formally, in this connection the radical L on the terminal phenyl group of the carboxylic acid derivative serving as a starting compound is replaced by a phenyl compound of the following formula M-B-W-D  (IIb)

where
M is —H, —I, —$N_2^+$, —COOOCOBNO$_2$ or an organometallic radical;
B is a phenylene group which is 1,3- or 1,4-substituted with respect to M and W-D and optionally contains additional radicals;
W is as defined above;
D is —$NO_2$, —$NH_2$ or —CHO;

Possible coupling reactions are, for example, the reaction of two unsubstituted phenyl groups (i.e. L and M are equal to hydrogen) in the presence of $AlCl_3$ and an acid (Scholl reaction), the coupling of two phenyl iodides in the presence of copper (Ullmann reaction), the reaction of the unsubstituted carboxylic acid derivative with a phenyldiazonium compound under basic conditions (Gomberg-Bachmann reaction) or coupling with involvement of organometallic reagents. In this connection, the coupling of two phenyl-Grignard compounds in the presence of thallium bromide, the coupling of two organoboron compounds in the presence of silver nitrate and sodium hydroxide, the reaction of a diphenyllithium cuprate in the presence of oxygen and palladium-assisted couplings of a phenyl halide by an organometallic phenyl compound are worthy of mention. The implementation of these reactions is described in detail in standard works such as Houben-Weyl, Methoden der organischen Chemie [Methods of Organic Chemistry], Thieme-Verlag, Stuttgart. The choice of the coupling reaction is directed by the presence of optionally interfering or sensitive substances in the reactants. For the preferred radicals of the formula (II) according to the invention, however, it has proven particularly advantageous to prepare the biphenyl nucleus by coupling of a phenyl halide with an organometallic phenyl compound in the presence of a palladium-(II) compound and triphenyl-phosphane.

The phenyl halide used here can be the corresponding phenyl fluoride, chloride, bromide or iodide, the corresponding bromide being particularly preferred. The organometallic phenyl compound used is preferably a substance in which a metallic element such as, for example, zinc, magnesium, boron, lithium, copper, tin or another element conventionally used for these purposes is bonded directly to the aryl ring. According to the invention, organoboron compounds are particularly preferred. Further substituents can additionally be bonded to the aryl ring in addition to the radical —W—D and the metallic element. Preferably, these substituents are one or more alkyl radicals, preferably a $C_{1-6}$-alkyl radical such as methyl, ethyl, propyl, isopropyl, butyl, isobutyl, t-butyl, pentyl, isopentyl, neopentyl, hexyl, a $C_{3-7}$-cycloalkyl radical such as cyclopropyl, cyclobutyl, cyclopentyl, cyclohexyl, and particularly preferably one or more methyl groups. If W is present, i.e. the radical D is bonded to the phenyl ring B via an optionally substituted alkylene group, the length of the main chain of this alkylene chain must be selected for the reasons described above such that in the resulting compound of the formula (IIc) not more than 6 atoms are present between the terminal carboxyl unit and the radical D in addition to the biphenyl nucleus.

Particularly preferred aryl reagents according to the invention are 3-nitrobenzeneboronic acid or 3-formylbenzeneboronic acid.

The radical D introduced into the compound is converted into an amino group, if it is not already an amino group. In the case in which D is a nitro group, this is reduced to the corresponding amino group by conventional reducing agents such as, for example, tin chloride. In the case in which D is an aldehyde group, the conversion into the amino group is carried out by reaction with an amine under reducing conditions, for example in the presence of an orthoester and of a reducing agent such as a metal hydride, for example a borohydride. The amino group thus formed can subsequently be derivatized, for example by reaction with, for example, alkyl or cycloalkyl halides. With respect to the preferred substituents which can be introduced in this way on the nitrogen atom, reference is made to the above description of the radicals of the formula (II) according to the invention.

According to a preferred embodiment of the present invention, the synthesis of the radicals of the formula (II) according to the invention is carried out on a solid phase such as a polystyrene resin, particularly preferably a commercially obtainable Wang polystyrene resin. In this connection, the resin is first swollen in a solvent such as dimetbylformamide (DMF). The appropriate carboxylic acid serving as a starting compound is then bonded to the resin by standard processes. For example, the bonding of the carboxylic acid to the resin can be carried out in the presence of a base such as pyridine and a reagent activating the carboxyl unit, such as an acid halide, for example dichlorobenzoyl chloride, in a solvent such as dimethyl-formamide (DMF). However, other reagents conventionally used for this purpose can also be employed. The reaction mixture is stirred at room temperature and normal pressure for at least 2 hours, preferably 12 hours, particularly preferably approximately 24 hours, the carboxylic acid being employed in an excess, preferably in a two- to three-fold excess, with respect to the loading of the solid phase.

After removal of reagents which may be unreacted, if desired a derivatization of the carboxylic acid bonded to the resin can be carried out without this previously needing to be removed from the resin. According to a preferred embodiment according to the invention, for example, an amino acid as described above whose amino group is protected is bonded to the solid phase and then, after liberation of the amino group, a substituent is introduced into the latter. The amino group is preferably sulphonylated or carbamoylated. For this, the amino acid bonded to the solid phase is treated with an excess of a solution of the appropriate sulphonylating or carbamoylating agent, preferably a two- to four-fold excess, particularly preferably an approximately threefold excess, in a solvent such as, for example, tetrahydrofuran (THF) in the presence of an auxiliary base such as diisopropylethylamine and the reaction mixture is stirred at room temperature and normal pressure for at least 2 hours, preferably 12 hours, particularly preferably approximately 24 hours. The sulphonamide or carbamate obtained does not have to be removed from the resin, but can immediately be reacted further after removal of unreacted reactants which are possibly present.

The aryl—aryl coupling is preferably carried out according to the invention by treating the optionally derivatized, for example sulphonylated or carbamoylated as described above, carboxylic acid bonded to the solid phase in aqueous medium in the presence of a base such as sodium carbonate with the appropriate aryl coupling reagent of the formula (IIb) and a catalyst conventionally used for this purpose, for example a palladium-(II) salt, preferably bis-(triphenylphosphane)-palladium-(II) chloride in combination with triphenylphosphane. In this connection, preferably an approximately 3- to 8-fold, preferably an approximately 4- to 6-fold, excess of the aryl coupling agent is employed, which according to the invention is in particular 3-nitrobenzeneboronic acid or 3-formylbenzeneboronic acid, and catalytically active amounts of the palladium compound, for example an approximately 10-fold excess with respect to the carboxylic acid, and the reaction mixture is heated after briefly stirring at room temperature, for example for 5 to 10 minutes, for approximately 2–24 hours, preferably 6–24 hours and particularly preferably 12–24 hours at a temperature in the range from 40 to 110° C., preferably 50 to 100° C. and particularly preferably 60 to 90° C. The biphenyl compound obtained can immediately be reacted further without purification after unreacted reactants which may be present have been removed by washing with an acidic solution, for example a hydrochloric acid solution.

If the radical D is a nitro group, its conversion into an amino group according to the invention is preferably carried out by addition of a customary reducing agent such as tin-(II) chloride to the intermediate obtained as above bonded to the solid phase, if appropriate in the presence of solvents such as N-methylpyrrolidone (NMP) by stirring the reaction mixture at room temperature and normal pressure for at least 2 hours, preferably 12 hours, particularly preferably approximately 24 hours.

If the radical D is an aldehyde group, its conversion into an amino group is carried out by reductive amination. For this, the intermediate obtained as above and bonded to the solid phase is treated with an approximately 3- to 6-fold, preferably a 4- to 5-fold, excess of an amine in the presence of a neutralizing agent such as diisopropylethylamine and of an orthoester which is present in an approximately 6- to 10-fold excess. After stirring at room temperature for a number of hours, preferably 1 to 3 hours, an approximately 3- to 6-fold, preferably 4- to 5-fold, excess of an acidic solution of a metal hydride such as, for example, tetrabutylammonium borohydride is added to the reaction mixture and it is again stirred for a number of hours, preferably 12–24 hours, at room temperature.

The product obtained above can optionally be reacted further by derivatization of the radical D representing an amino group of the compound of the formula (IIc) or introduction of further substituents onto nitrogen atoms present in the molecule or directly removed from the resin. Removal from the resin is carried out in a conventional manner in an acidic medium. The product removed from the resin can be purified by known purification processes such as, for example, chromatographic processes after removal of solvents which may be present.

Furthermore, the radical D representing an amino group of the compound of the formula (IIc) can be converted into an amide group, urea group, thioamide group, thiourea group, amidine group or guanidine group. These structural units can be prepared by standard reactions familiar to the person skilled in the art, such as are described, for example, in Houben-Weyl, Methoden der organischen Chemie [Methods of Organic Chemistry], Georg Thieme Verlag, Stuttgart.

It is particularly preferred according to the invention to convert the radical D representing an amino group of the compound of the formula (IIc) into a urea or thiourea unit. For this, the above amino group of the carboxylic acid bonded to the solid phase is first preferably reacted with a 2- to 5-fold, preferably 3- to 4-fold, excess of a carbonic acid ester or thiocarbonic acid ester derivative in an inert solvent such as tetrahydrofuran (THF), dichloromethane or a mixture of both (preferably a 1:1 mixture) at room temperature and stirring for approximately 1 hour, preferably approximately 45 minutes. The carbonic acid ester or thiocarbonic acid ester derivative used can preferably be phosgene, triphosgene, thiophosgene or chloro-formic acid esters, commercially available chloroformic acid esters being preferred for the preparation of the urea derivatives and thiophosgene being preferred for the preparation of the thiourea derivatives.

The carbamates or isothiocyanates formed in this way can be converted into the corresponding urea and thiourea derivatives by reaction with suitable amines. The amines used can be substances of the formula HNRR', where R and R' independently of one another or simultaneously can be hydrogen, a substituted or unsubstituted alkyl or cycloalkyl radical, a substituted or unsubstituted aryl radical, a saturated or unsaturated, optionally substituted heterocyclic radical, an alkylamine radical, an alkylamide radical or can be connected to one another and together with the nitrogen atom can form an optionally substituted heterocyclic ring system which can be saturated or unsaturated and/or can contain further heteroatoms. With respect to the preferred radicals on the amine, reference is made to the above description of the radicals of the formula (II) according to the invention. According to the invention, the carbamate or isothiocyanate bonded to a solid phase is preferably reacted with a distinct excess of amine, preferably a 3- to 10-fold excess and particularly preferably a 5- to 10-fold excess, at room temperature with stirring for approximately 1 to 5 hours, preferably approximately 2 to 3 hours, in the presence of an auxiliary base such as diisopropylethylamine in an inert solvent such as dimethylformamide (DMF).

The radical of the formula (III) addressing $\alpha_v\beta_3$ integrin receptors can be prepared from commercially obtainable starting compounds via the following steps:

The essential steps of the preparation process according to the invention are the reaction of a β-amino acid of the formula (IIIa)

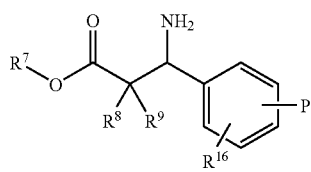
(IIIa)

where
P is $-(CH_2)_mNO_2$, $-(CH_2)_mO-C_{1-6}$-alkyl, $-(CH_2)_mSO_2P'$, $-(CH_2)_mCOP'$, $-(CH_2)_mCH_2O-C_{1-6}$-alkyl, where m is in each case an integer of 0 or 1;
P' is $-OH$, $-O-C_{1-6}$-alkyl,
and the other radicals are as defined above, where $R^7$ can additionally be a solid phase conventionally used for carrying out a solid-phase reaction;

with a compound $R^{10}$-A to give a compound of the formula (IIIb)

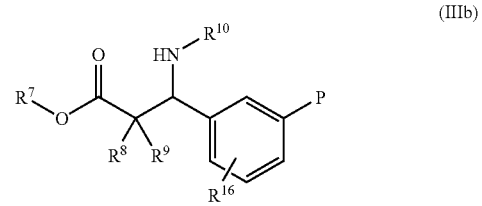
(IIIb)

where
$R^{10}$ is $-SO_2R^{10'}$, $-COOR^{10''}$ or $-COR^{10'}$; $R^{10'}$ and $R^{10''}$ are as defined above;
A is $-Cl$, $-Br$, $-I$, $-O$-triflyl, $-O$-tosyl, $-O-C_{1-6}$-alkyl, $-O-CO-C_{1-6}$alkyl, $-O-CO-O-C_{1-6}$-alkyl, $-OC(CH_3)=CH_2$;
and the other radicals are as defined above;

the conversion of the radical P into the radical Q, where
Q is $-(CH_2)_mNH_2$, $-(CH_2)_mOH$, $-(CH_2)_nCH_2OH$, $-(CH_2)_mSO_2A$, $-(CH_2)_mCOA$,
A is as defined above;
m is an integer of 0 or 1;

the reaction of the compound (IIIb) obtained above with a compound of the formula (IIIc)

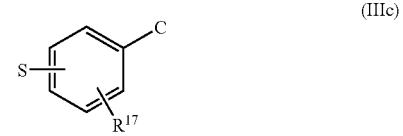
(IIIc)

where
S is $ASO_2(CH_2)_n-$, $NH_2(CH_2)_n-$, $ACO(CH_2)_n-$, $HOCH_2(CH_2)_n-$, $M(CH_2)_n-$, $MCH_2(CH_2)_n-$, $HSCH_2(CH_2)_n-$ or $HS(CH_2)_n-$,
where
n is an integer of 0 or 1;
M is a radical including Mg, Li, Cd or Sn;
A is as defined above; and

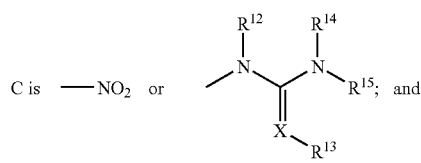

X, $R^{12}$, $R^{13}$, $R^{14}$ and $R^{15}$ are as defined above;
to give a compound of the formula (IIId)

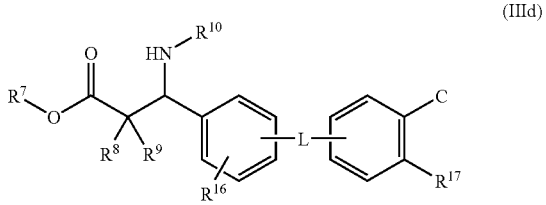

where the radicals are as defined above;

if appropriate the conversion of C, if C is a nitro group, into an optionally cyclic urea, thiourea or guanidine unit with retention of the radical (III); and if appropriate the removal of protective groups and/or derivatization of nitrogen atoms present at preferred points of time in the preparation process and/or conversion of the compound obtained into the free acid and/or conversion of the compound obtained into one of its physiological salts by reaction with an inorganic or organic base or acid.

The β-amino acid derivatives of the formula (IIIa) are either commercially obtainable or are accessible in a simple manner by standard chemical processes, such as are known to any person skilled in the art and are described in standard works such as Houben-Weyl, Methoden der organischen Chemie [Methods of Organic Chemistry], Georg Thieme-Verlag, Stuttgart. In particular, reference is made to the preparation processes for β-amino acid derivatives described by Rodionow et al., J. Am. Chem. Soc. 51, 1929, 844–846, Kunz et al., Angew. Chem. 101, 1989, 1042–1043 and Ishihara et al., Bull. Chem. Soc. Jpn., 68, 6, 1995, 1721–1730.

According to a preferred embodiment of the present invention, the -amino acid derivatives of the formula (IIa) are obtained by reaction of malonic acid with a benzaldehyde derivative of the formula (IIIa')

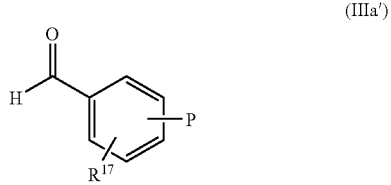

where $R^{17}$ and P are as defined above, in the presence of ammonia, ammonium compounds or amines. Instead of malonic acid, an ester, if appropriate with addition of a base conventionally employed for these purposes, such as NaH or a sodium alkoxide, preferably sodium methoxide or sodium ethoxide, can also be used. Preferably, an ammonium compound such as, for example, ammonium acetate is employed as the nitrogen compound.

The benzaldehyde derivatives (IIIa') are either commercially obtainable or are accessible in a simple manner by standard chemical processes, such as are known to any person skilled in the art and are described in standard works such as Houben-Weyl, Methoden der organischen Chemie [Methods of Organic Chemistry], Georg Thieme-Verlag, Stuttgart.

According to a preferred embodiment of the present invention, a nitrobenzaldehyde derivative such as 3- or 4-nitrobenzaldehyde or an alkoxybenzaldehyde derivative such as 3- or 4-methoxybenzaldehyde is employed as the compound of the formula (IIIa').

According to a preferred embodiment of the present invention, the β-amino acid of the formula (IIIa) is obtained by reaction of approximately equimolar amounts of malonic acid, ammonium acetate and 3-nitrobenzaldehyde or 3-methoxybenzaldehyde in a solvent such as isopropanol with heating for a number of hours, preferably 2 to 6 hours, at 50 to 110° C., preferably with reflux of the solvent, in the surrounding atmosphere (i.e. in the air and under normal pressure).

For the following reaction steps, the carboxyl group is blocked by a conventional protective group P. Protective groups of this type are known to the person skilled in the art and do not have to be expressly mentioned here. The carboxyl group is particularly preferably esterified, where P is a $C_{1-6}$-alkyl such as, for example, methyl, ethyl, propyl, isopropyl, butyl, isobutyl, t-butyl, pentyl, isopentyl, neopentyl, hexyl, a $C_{3-7}$-cycloalkyl such as, for example, cyclopropyl, cyclopropylmethyl, cyclobutyl, cyclopentyl, cyclohexyl, an aryl such as, for example, phenyl, benzyl, tolyl or a substituted derivative thereof.

Furthermore, the preparation process according to the invention for the radicals of the formula (III) can be carried out on a solid phase as described above for radicals of the formula (II). In this case, the carboxyl radical can be connected to any solid phase conventionally used for reactions of this type, such as a polystyrene resin, for example a Wang polystyrene resin.

According to a preferred embodiment according to the invention, the carboxyl group of the above β-amino acid is esterified by reaction with an alcohol such as ethanol or a polymer conventionally used for carrying out a solid-phase reaction. This can be carried out under conditions known to the person skilled in the art, such as acid catalysis and, if appropriate, addition of a dehydrating agent such as dicyclohexyl-carbodiimide. Preferably, however, the β-amino acid is suspended in the appropriate alcohol present in an excess, such as ethanol, HCl is passed through for a period of approximately 30 minutes to approximately 2 hours and the mixture is then heated in a surrounding atmosphere for a number of hours, preferably approximately 1 to 6 hours and particularly preferably approximately 3 to 5 hours, at approximately 50 to approximately 100° C., preferably under reflux of the alcohol.

The carboxyl-protected β-amino acids accessible in this way are reacted with a suitable sulphonating, carbamoylating or acylating reagent in order to obtain the corresponding sulphonamide, carbamate or amide derivatives. The sulphonating reagent used is preferably a sulphonyl chloride of the formula $R^{10'''}$-$SO_2Cl$ or a carbamoyl chloride of the formula $R^{10'''}$-OCOCl, where $R^{10'''}$ is a $C_{1-10}$-alkyl such as methyl, ethyl, propyl, isopropyl, butyl, isobutyl, t-butyl, pentyl, isopentyl, neopentyl, hexyl, heptyl, octyl, nonyl, decyl, cyclopropyl, cyclobutyl, cyclopentyl, cyclohexyl, or camphor-10-yl, an aryl such as phenyl, benzyl, tolyl, mesityl or substituted derivatives of these such as —$C_6H_2(CH_3)_3$, —$C_6(CH_3)_5$, —$CH_2C_6H_2(CH_3)_3$, 2-chlorophenyl, 3-chlorophenyl, 4-chlorophenyl, 3-aminophenyl, 4-aminophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4- methyl-thiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-meth-ylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methyl-benzothiazol-2-yl, N-methoxycarbonyl-piperidin-3-yl, thiophen-2-yl, isoxazol-5-yl, 2-chloropyridin-3-yl, pyridin-3-yl, 5-methylisoxazol-3-yl, 1-adamantyl, 4-chlorophenoxymethyl, 2,2-dimethylethenyl, 2-chloropyridin-5-methyl, 5,7-dimethyl-1,3,4-triazaindolizin-2-yl, (S)-camphan-1-yl, (R)-camphan-1-yl, 8-quinolinyl, or a heterocyclic analogue of the abovementioned cyclic radicals. Instead of the abovementioned sulphonyl or carbamoyl chlorides, it is also possible to employ the corresponding fluorides, bromides or iodides. As acylating reagent, the appropriate carboxylic acid halides or carboxylic acid anhydrides are reacted with the amino group, the appropriate $C_{1-6}$-alkyl carboxylic acid chlorides such as methyl-, ethyl-, propyl-, isopropyl-, butyl-, isobutyl-, t-butyl-, pentyl-, isopentyl-, neopentyl-, hexyl-, $C_{3-7}$-cycloalkyl such as cyclopropyl-, cyclobutyl-, cyclopentyl-, cyclohexyl-, aryl such as phenyl-, benzyl-, tolylcarboxylic acid chlorides or substituted derivatives thereof being preferred according to the invention. For the preparation of the urea or thiourea radicals, the amino group is preferably first reacted with a carbonic acid or thiocarbonic acid derivative such as a chloroformic acid ester or thiophosgene and then with a desired amine. The above reactions and their implementation are well known to the person skilled in the art and are described in detail in standard works such as, for example, Houben-Weyl, Methoden der organischen Chemie [Methods of Organic Chemistry], Georg Thieme Verlag, Stuttgart.

According to a preferred embodiment of the invention, the carboxyl-protected β-amino acid of the formula (IIa) is treated with an equimolar amount or a slight excess of the appropriate sulphonylating agent, for example phenylsulphonyl chloride, or acylating agent, for example mesitylacetyl chloride, with cooling, preferably at 0° C., in a solvent such as pyridine or dioxane in a surrounding atmosphere in the presence of a base such as an amine, preferably triethylamine or diisopropylethylamine, and the mixture is stirred at this temperature for a period of approximately 10 minutes to approximately 2 hours. In the case of sulphonylation, this is followed by stirring at room temperature for a number of hours, preferably approximately 2 to 6 hours.

Before the synthesis of the linker group L, the radical P of the compound of the formula (IIIb) must be converted into a group Q which can participate in a nucleophilic substitution either as a nucleophilic reagent or as a substrate. If P includes a nitro group, this will be reduced to the corresponding amino group, which according to the present invention can preferably be carried out by addition of Tin(II) chloride to a solution of the compound of the formula (IIIb) in a solvent such as ethanol and subsequent heating to approximately 50 to 110° C., preferably under reflux of the solvent, for a number of hours, preferably approximately 1 to 4 hours, in a surrounding atmosphere. If P includes an ether group, the liberation of the corresponding hydroxyl group is preferably carried out by addition of a Lewis acid such as boron tribromide in a solvent such as dichloromethane with cooling, preferably at −78° C., and subsequent stirring for a number of hours, preferably 6 to 24 hours, at room temperature. If P includes a sulphonic acid or carboxylic acid group, a conversion into the corresponding sulphonyl or carboxylic acid halide is preferably carried out. This can be carried out in a manner known to the person skilled in the art, for example by reaction of the corresponding sulphonic or carboxylic acid with thionyl chloride.

The compound prepared in this way is then reacted with a compound of the formula (IIIc)

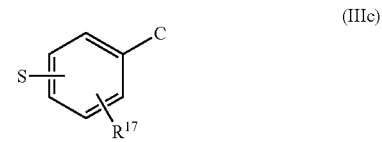

where

S is $ASO_2(CH_2)_n-$, $NH_2(CH_2)_n-$, $ACO(CH_2)_n-$, $HOCH_2(CH_2)_n-$, $M(CH_2)_n-$, $MCH_2(CH_2)_n-$, $HSCH_2(CH_2)_n-$ or $HS(CH_2)_n-$, where n is an integer of 0 or 1;

M is a radical including Mg, Li, Cd or Sn;

A is as defined above; and

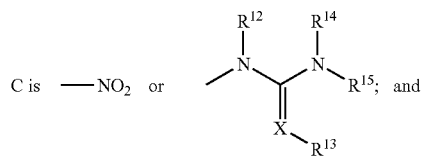

$X$, $R^{12}$, $R^{13}$, $R^{14}$ and $R^{15}$ are as defined above; to give a compound of the formula (IIId)

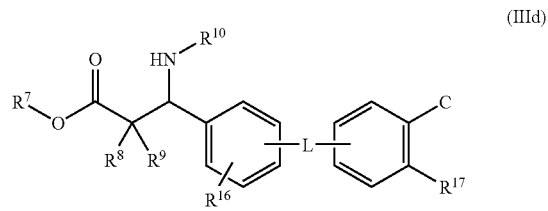

where the radicals are as defined above. This reaction formally represents the substitution of a leaving group in one of the starting compounds by a nucleophilic unit in the other starting compound in each case.

According to a preferred embodiment of the present invention, the reactants are mixed together in approximately equimolar amounts in the presence of a base such as pyridine or sodium hydride and, if appropriate, in a solvent such as, for example, tetrahydrofuran (THF) or dimethylformamide (DMF) in a surrounding atmosphere at room temperature or with cooling, preferably at approximately 0° C., and stirred for a number of hours, preferably approximately 1 h to approximately 24 hours, at room temperature or with cooling, for example at 0° C.

The compounds of the formula (IIId) thus obtained are converted into the radicals of the formula (III) according to the invention by conversion of the terminal nitro group into an open-chain or cyclic guanidine, urea or thiourea unit.

For this, the nitro group is first converted according to the invention into an amino group, preferably by addition of a customary reducing agent such as tin-(II) chloride, if appropriate in the presence of solvents such as ethanol, by stirring the reaction mixture with heating at approximately 50 to 110° C., preferably under reflux of the solvent, in a surrounding atmosphere for approximately 2 hours.

The amino group thus obtained is then converted into a guanidine, urea or thiourea unit. For this, the above amino group is first preferably reacted with a carbonic acid ester or thiocarbonic acid ester derivative in a solvent such as dimethylformamide (DMF) in the presence of mercury-(II) chloride with cooling, preferably at approximately 0° C., and stirring for approximately 10 minutes to approximately 3 hours with cooling, preferably at approximately 0° C., and if appropriate subsequently at room temperature. The carbonic acid ester or thiocarbonic acid ester derivative employed can preferably be phosgene, triphosgene, thiophosgene, chloroformic acid esters or thiopseudourea derivatives, commercially obtainable chloroformic acid esters being preferred for the preparation of the urea derivatives, thiophosgene being preferred for the preparation of the thiourea derivatives and thiopseudourea derivatives being preferred for the preparation of guanidine derivatives.

The carbamates or isothiocyanates formed in this way can be converted into the corresponding urea, thiourea and guanidine derivatives by reaction with appropriate amines. The amines used can be substances of the formula HNRR', where R and R' independently of one another or simultaneously can be hydrogen, a substituted or unsubstituted alkyl or cycloalkyl radical, a substituted or unsubstituted aryl radical, a saturated or unsaturated, optionally substituted heterocyclic radical, an alkylamine radical, an alkylamide radical or can be connected to one another and together with the nitrogen atom can form an optionally substituted heterocyclic ring system which can be saturated or unsaturated and/or can contain further heteroatoms. With respect to the preferred radicals on the amine, reference is made to the above description of the compounds according to the invention. According to the invention, the carbamate or isothiocyanate is preferably reacted with an amine at room temperature with stirring for approximately 1 to 5 hours, preferably approximately 2 to 3 hours, in the presence of an auxiliary base such as diisopropylethylamine in a solvent such as dimethylformamide (DMF). In the case of the preparation of cyclic guanidine derivatives, the corresponding isothiocyanate is preferably first heated in ethanol for a number of hours, preferably approximately 12 to 24 hours, and then heated with a diamine such as diaminoethane in a solvent such as toluene, dimethylformamide (DMF) or a mixture of both.

According to a further preferred embodiment of the present invention, it is also possible to generate the above guanidine, urea or thiourea group on the compound of the formula (IIIc) in the above manner and then to react the compound of the formula (IIIc) thus obtained with the compound of the formula (IIIb) in the manner described above.

The compounds obtained according to the process explained above can furthermore be derivatized by removal of protective groups which may be present, further substitution of nitrogen atoms present at preferred positions in the preparation process and/or conversion of the compound obtained into the free acid and/or its physiologically acceptable salts. For example, the t-butoxymethoxycarbonyl groups conventionally used as protective groups for nitrogen atoms are removed in an acidic medium, for example by addition of trifluoroacetic acid. Suitable alkylating agents for derivatization of nitrogen atoms are reagents conventionally used for this purpose in this step, to which, for example, a substituted or unsubstituted alkyl or cycloalkyl radical, a substituted or unsubstituted aryl radical or a saturated or unsaturated, optionally substituted heterocyclic radical can be bonded to the corresponding nitrogen atom. With respect to the substituents preferably bonded to the respective nitrogen atoms, reference is made to the above description of the compounds according to the invention. The above reactions and their implementation are well known to the person skilled in the art and are described in detail in standard works such as, for example, Houben-Weyl, Methoden der organischen Chemie [Methods of Organic Chemistry], Georg Thieme Verlag, Stuttgart.

The ester derivatives according to the invention can be converted into the corresponding free carboxylic acids in a conventional manner, such as, for example, by basic ester hydrolysis.

If desired, the compounds according to the invention can be converted into their physiologically acceptable salts. This can be carried out either by reaction with an organic or inorganic base such as, for example, an alkali metal hydroxide or alkaline earth metal hydroxide such as KOH, NaOH, LiOH, $Mg(OH)_2$ or $Ca(OH)_2$, whereby the terminal carboxyl group is deprotonated and the corresponding carboxylate is formed, or by reaction with an organic or inorganic acid such as, for example, hydrochloric acid, sulphuric acid, phosphoric acid, mandelic acid, oleic acid, linoleic acid or p-toluenesulphonic acid, whereby one or more of the above nitrogen atoms are protonated.

The radical of the formula (IV) addressing $\alpha_v\beta_3$ integrin receptors can be prepared from commercially obtainable starting compounds as explained in Example II.2.

The conjugates according to the invention can be used as active compound components for the production of medicaments against carcinomatous disorders. For this, they can be converted into the customary formulations such as tablets, coated tablets, aerosols, pills, granules, syrups, emulsions, suspensions and solutions in a known manner using inert, non-toxic, pharmaceutically suitable excipients or solvents. Preferably, the compounds according to the invention are used here in an amount such that their concentration in the total mixture is approximately 0.5 to approximately 90% by weight, the concentration, inter alia, being dependent on the corresponding indication of the medicament.

The abovementioned formulations are produced, for example, by extending the active compounds with solvents and/or excipients having the above properties, where, if appropriate, additionally emulsifiers or dispersants and, in the case of water as the solvent, alternatively an organic solvent, have to be added.

The medicaments according to the invention can be administered in a customary manner.

The present invention is illustrated below with the aid of non-restricting examples and comparison examples.

EXAMPLES

In the examples below, all quantitative data, if not stated otherwise, relate to percentages by weight. The mass determinations were carried out by high-performance liquid chromatography-mass spectrometry (HPLC-MS) using the electron spray ionization (ESI) method or by FAB or MALDI mass spectroscopy.

List of the Abbreviations Used

| HPLC | high-performance liquid chromatography |
| --- | --- |
| RP | reverse phase |
| ACN | acetonitrile |
| DMF | dimethylformamide |
| DCM | dichloromethane |
| THF | tetrahydrofuran |
| DIEA | diisopropylethylamine (Hünig's base) |
| NMP | N-methylpyrrolidone |
| TFA | trifluoroacetic acid |
| Fmoc | 9-fluorenylmethoxycarbonyl |
| RT | room temperature |
| MTBE | methyl tert-butyl ether |
| Boc | tert-butyloxycarbonyl |
| TLC | thin-layer chromatography |
| DMAP | dimethylaminopyridine |
| DMSO | dimethyl sulphoxide |

I. Preparation of Camptothecin Conjugates

I.1. 20-O-L-Valyl-camptothecin trifluoroacetate

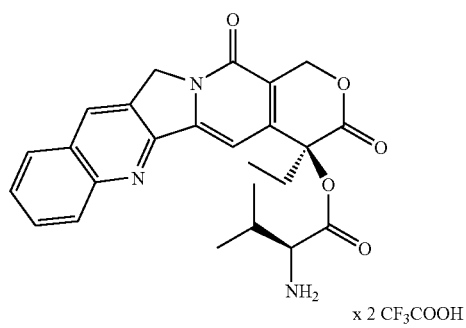

A suspension of 10 g (28.7 mmol) of 20(S)-camptothecin in 500 ml of absolute dichloromethane is treated with stirring with 14 g (2 eq.) of N-(tert-butoxycarbonyl)-valine-N-carboxyanhydride and 1 g of 4-(N,N-dimethylamino)-pyridine. After heating under reflux for 4 days, the mixture is concentrated in vacuo. The residue is stirred with 100 ml of MTBE for 20 min. 200 ml of petroleum ether are then added and the mixture is filtered. 14.9 g of the Boc-protected intermediate compound are obtained, which can contain small amounts of D-valine epimer which, however, can be removed without problems after removal of the protective group.

11.65 g of this Boc-protected intermediate compound are then stirred at 5° C. for 1 h in a mixture of 300 ml of dichloromethane and 70 ml of anhydrous trifluoroacetic acid. After concentrating in vacuo to a small volume, the product is precipitated with diethyl ether and thoroughly washed with diethyl ether. The product is again precipitated from dichloromethane/methanol using diethyl ether. If appropriate, the crude product is again taken up in 40 ml of methanol, and the solution is treated with 120 ml of MTBE and cooled to 0° C. The precipitate is filtered off and 9.4 g (80%) of 20-O-(valyl)-camptothecin trifluoroacetate are obtained after drying.

[TLC: acetonitrile/water (20:1); $R_f$=0.39].

I.2-[L-Valyl-camptothecin]-benzyl L-glutamate trifluoroacetate

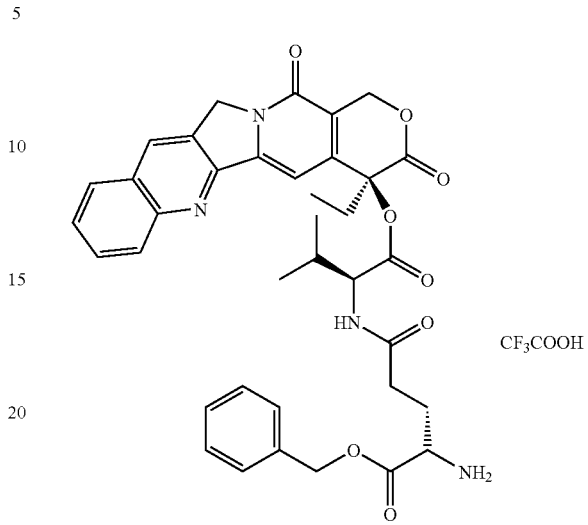

400 mg (1.185 mmol) of benzyl N-tert-butoxycarbonyl-glutamate are dissolved in 40 ml of DMF and treated with 273 mg (1.2 eq) of N-(3-dimethylaminopropyl)-N'-ethylcarbodiimide hydrochloride and with 240 mg (1.5 eq) of hydroxybenzotriazole. After 1 h, 665 mg (1.185 mmol) of the compound from Example I.1 and 811 µl of Hünig's base are added. The coupling reaction is complete after 2 h. The reaction mixture is concentrated in vacuo. The residue is taken up in dichloromethane, the mixture is extracted twice with water and then the organic phase is dried and concentrated again. The residue is then taken up in dichloromethane/methanol, a little ether is added and it is then precipitated with petroleum ether. This purification process is repeated and the intermediate is filtered off and dried (yield: 752 mg=83%).

100 mg (0.13 mmol) of this Boc-protected intermediate compound are then stirred at room temperature for 1 h with 10 ml of dichloromethane and 1 ml of anhydrous trifluoroacetic acid. After concentrating in vacuo, the product is taken up in dichloromethane/methanol, precipitated with diethyl ether and thoroughly washed with diethyl ether. The product is again precipitated from dichloromethane/methanol using diethyl ether. The precipitate is filtered off and 85 mg (84%) of the target compound are obtained after drying.

[TLC: acetonitrile/water 10:1 $R_f$=0.4].

Analogously, the following, partially protected camptothecin-peptide conjugates were prepared by reaction of appropriate camptothecin-amino acid conjugates with further partially protected amino acids. If appropriate, protective groups are removed according to known methods:

| Example | Compound | $R_f$ value |
| --- | --- | --- |
| I.3 | 20-O-[L-Histidyl-L-valyl]-camptothecin trifluoroacetate | 0.4[1] |
| I.4 | 20-O-{N$^\varepsilon$-[Fluorenyl-9-methoxycarbonyl]-L-lysyl-L-valyl}-camptothecin trifluoroacetate | 0.4[2] |
| I.5 | 20-O-[L-Glutamic acid L-valyl]-camptothecin | 0.28[1] |
| I.6 | 20-O-(Glutaryl-glycyl-L-valyl)-camptothecin | 0.7[1] |

83

-continued

| Example | Compound | $R_f$ value |
|---|---|---|
| I.7 | 20-O-(Glutaryl-glycyl-L-leucyl)-camptothecin | 0.25[3)] |
| I.8 | 20-O-(Glutaryl-L-leucyl-glycyl-L-leucyl)-camptothecin | 0.68[1)] |
| I.9 | 20-O-(Glutaryl-glycyl-L-leucyl-L-valyl)-camptothecin | 0.4[4)] |
| I.10 | 20-O-(Glutaryl-L-prolyl-L-leucyl-glycyl-L-leucyl)-camptothecin | 0.2[3)] |

[1)]Acetonitrile/water/glacial acetic acid 5:1:0.2
[2)]Dichloromethane/methanol 10:1
[3)]Acetonitrile/water 10:1
[4)]Dichloromethane/methanol/glacial acetic acid 10:1/0.1

I.11 20-O-Succinylcamptothecin 1 g (2.9 mmol) of camptothecin is initially introduced into 50 ml of dichloromethane and treated with 100 mg of dimethylaminopyridine (DMAP) and 600 mg of succinic anhydride. After a reaction time of 44 h, equal amounts of DMAP and succinic anhydride are again added and the mixture is stirred for a further 48 h. It is purified by flash chromatography on silica gel (acetonitrile—>acetonitrile/water (20:1)). The corresponding fractions are concentrated and the product is precipitated from dichloromethane/methanol using ether. Yield: 160 mg (13%). [TLC: (acetonitrile/water (10:1); $R_f$=0.6].

I.12. 20-O-[N$^\alpha$-(Phenylamino-thiocarbonyl)-L-lysyl-L-valyl]-camptothecin

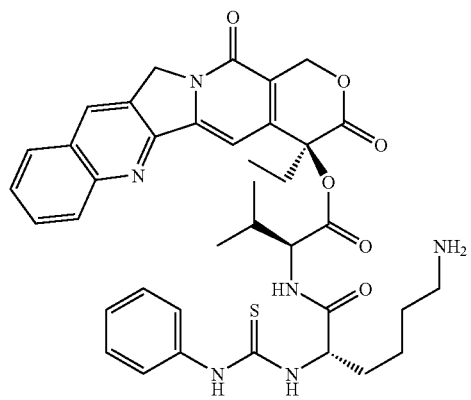

666 mg (0.73 mmol) of the compound from Example I.4 are dissolved in 40 ml of DMF and treated with 500 µl of Hünig's base. 87 µl (1 eq) of commercially obtainable phenyl isothiocyanate are then added and the mixture is stirred overnight. It is then concentrated and the residue is precipitated twice from dichloro-methane/methanol using ether. The precipitate is filtered off and after drying 614 mg (90%) of the protected intermediate are obtained. [TLC: (acetonitrile) $R_f$=0.66].

614 mg (0.658 mmol) of this intermediate compound are dissolved in 20 ml of DMF and treated with 2 ml of piperidine. After stirring at RT for 45 minutes, the mixture is concentrated. The residue is precipitated twice from dichloromethane/methanol using ether. It is filtered off and 365 mg (78%) of the target compound are obtained after drying. [TLC: (acetonitrile/water/glacial acetic acid 5:1:0.2) $R_f$=0.46].

84

II. Preparation of Non-Peptide Integrin Ligands or Intermediates Suitable for Linkage

II.1 Ethyl-3-amino-(3-(3-[N,N'-bis-t-butoxycarbonyl-guanidino]-benzene-sulphonylamino)-phenyl]-3-propanoic acid

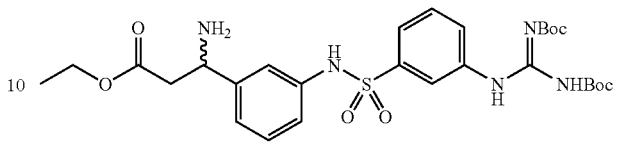

II.1a: 3-Amino-3-nitrophenylpropionic acid hydrochloride

3-Nitrobenzaldehyde (151 g), ammonium acetate (94 g) and malonic acid (127 g) were heated under reflux in isopropanol (1 l) for 5 h. The solution was filtered and the precipitate was washed with hot isopropanol (0.7 l). The crude product was dried in vacuo (yield: 146 g).

$^1$H-NMR (D$_4$-MeOH): 3.09 (m, 2H), 4.88 (m, 1H), 7.74 (t, 1H), 7.90 (d, 1H), 8.33 (d, 1H), 8.43 (s, 1H).

II.1b: 3-Amino-3-(3-nitrophenyl)-propionate hydrochloride

3-Amino-3-nitrophenylpropionic acid hydrochloride from II.1 a (60 g) were suspended in 660 ml of ethanol and gaseous HCl was passed in for 1 h. The reaction mixture was then heated under reflux for 4 h and was cooled and concentrated. A white solid was obtained (yield: 62 g).

$^1$H-NMR (D$_4$-MeOH): 1.22 (t, 3H), 3.12 (dd, 1H), 3.20 (dd, 1H), 4.18 (q, 2H), 4.95 (t, 1H), 7.77 (t, 1H), 7.94 (d, 1H), 8.35 (d, 1H), 8.43 (s, 1H).

II.1c: Ethyl 3-allyloxycarbonylamino-3-(3-nitrophenyl)-propionate

Diisopropylethylamine (66 ml) and allyl chloroformate (22 ml) in 150 ml of methylene chloride were added at 0° C. to a solution of ethyl 3-amino-3-(3-nitrophenyl)-propionate hydrochloride from II.1b (47 g) in 350 ml of methylene chloride. After a reaction time of 30 min, HCl (1N, 100 ml) was added. The organic phase was separated off, washed with water, dried over MgSO$_4$ and concentrated. A white solid was obtained (yield: 56.4 g).

$^1$H-NMR (CDCl$_3$): 1.19 (t, 3H), 2.91 (d, 2H), 4.09 (q, 2H), 4.57 (m, 2H), 5.18–5.26 (m, 3H), 5.92 (m, 1H), 6.04 (m, 1H), 7.52 (t, 1H), 7.68 (d, 1H), 8.14 (d, 1H), 8.20 (s, 1H).

II.1d::Ethyl 3-allyloxycarbonylamino-3-(3-aminophenyl)-propionate

Tin(II) chloride (64.6 g) was added to a solution of ethyl 3-allyloxycarbonylamino-3-(3-nitrophenyl)-propionate from II.1c (18.8 g) in 245 ml of ethanol, and the reaction mixture was heated under reflux for 2 h. After cooling the solution, it was adjusted to pH=7 using 2N NaOH, briefly heated, cooled again and filtered. It was then extracted with dichloromethane, and the org. phase was dried (MgSO$_4$) and concentrated. 10.9 g of product were obtained.

$^1$H-NMR (CDCl$_3$): 1.18 (t, 3H), 2.80 (m, 2H), 4.08 (q, 2H), 4.56 (m, 2H), 5.06 (m, 1H), 5.20 (d, 1H), 5.30 (d, 1H), 5.70 (m, 1H), 5.90 (m, 1H), 6.57 (d, 1H), 6.62 (s, 1H), 6.68 (d, 1H), 7.11 (t, 1H).

II.1e: Ethyl 3-allyloxycarbonylamino-3-(3-[3-nitrophenyl-sulphonylamino]-phenyl)-propionate 3-Nitrobenzenesulphonyl chloride (9.9 g) was added at 0° C. to a solution of ethyl 3-allyloxycarbonylamino-3-(3-aminophenyl)-propionate from II.1d (10.9 g) in 100 ml of pyridine. After a reaction time of 2 h at 0° C., the mixture was concentrated, treated with 1 N HCl (150 ml) and extracted with dichloromethane. After drying (MgSO$_4$), the solvent was removed, and 16.8 g of product were obtained.

$^1$H-NMR (CDCl$_3$): 1.18 (t, 3H), 2.78 (m, 2H), 4.06 (q, 2H), 4.53 (m, 2H), 5.04 (q, 1H), 5.18–5.35 (m, 2H), 5.80–5.95 (m, 2H), 6.79 (d, 2H), 7.00 (d, 1H), 7.03 (s, 1H), 7.11 (d, 1H), 7.24 (t, 1H), 7.65 (t, 1H), 8.03 (d, 1H), 8.38 (d, 1H), 8.61 (s, 1H).

II.1f: Ethyl 3-allyloxycarbonylamino-3-(3-[3-aminophenyl-sulphonylamino]-phenyl)-propionate Tin(II) chloride (39.7 g) was added to a solution of ethyl 3-allyloxycarbonylamino-3(3-[3-nitrophenylsulphony-lamino]-phenyl)-propionate from II.1e (16.8 g) in 155 ml of ethanol and the reaction mixture was heated under reflux for 2 h. After cooling, the solution was adjusted to pH=7 using 2N NaOH, briefly heated, cooled again and filtered. It was then extracted with dichloromethane, and the org. phase was dried (MgSO$_4$) and concentrated. 7.3 g of product were obtained.

$^1$H-NMR (CDCl$_3$): 1.12 (t, 3H), 2.73 (m, 2H), 3.91 (s, 2H), 4.02 (q, 2H), 4.49 (m, 2H), 5.01 (q, 1H), 5.15 (d, 1H), 5.24 (d, 1H), 5.75 (m, 1H), 5.84 (m, 1H), 6.47 (s, 1H), 6.69 (d, 1H), 6.81 (d, 1H), 6.88 (s, 1H), 6.99 (d, 1H), 7.03 (d, 1H), 7.08–7.15 (m, 3H).

II.1g: Ethyl 3-allyloxycarbonylamino-3-(3-(3-[N,N'-Bis-t-butoxycarbonyl-guanidino]-phenylsulphonylamino)-phenyl)-propionate Triethylamine (6.5 ml), 1,3-bis(t-butoxycarbonyl)-2-methyl-2-isothiourea (8.23 g) and mercuric chloride (7.7 g) were added at 0° C. to a solution of ethyl 3-allyl-oxycarbonylamino-3-(3-β-aminophenylsulphonylamino]-phenyl)-propionate from II.1f (10.5 g) in 320 ml of DMF. After a reaction time of 30 min at 0° C., the mixture was stirred at room temperature for a further 1.5 h. The precipitate was removed by filtration and the solution was concentrated. After chromatography (methylene chloride/methanol (40:1)), 13.5 g of product were obtained.

$^1$H-NMR (CDCl$_3$): 1.16 (t, 3H), 1.51 (s, 9H), 1.56 (s, 9H), 2.76 (m, 2H), 4.05 (q, 2H), 4.53 (m, 2H), 5.05 (m, 1H), 5.21 (m, 1H), 5.30 (m, 1H), 5.73 (m, 1H), 5.90 (m, 1H), 6.83 (s, 1H), 7.01–7.09 (m, 3H), 7.19 (t, 1H), 7.36 (m, 2H), 7.79 (d, 1H), 8.12 (s, 1H), 10.25 (s, 1H), 11.80 (s, 1H).

II.1: Ethyl-3-amino-(3-(3-[N,N'-bis-t-butoxycarbonyl-guanidino]-benzenesulphonyl-amino)-phenyl)]-3-propanoic acid Acetic acid (1.6 ml), bistriphenylphosphinepalladium dichloride (110 mg) and tributyltin hydride (3.5 g) were added to a solution of II.1g in methylene chloride (150 ml). After 2.5 h, bistriphenylphosphinepalladium dichloride (110 mg) and tributyltin hydride (3.5 g) were added again and the mixture was stirred for 24 h. The solution was treated with satd. NaHCO$_3$, extracted with methylene chloride, dried over MgSO$_4$ and concentrated. After chromatography (methylene chloride/methanol), 4.8 g of product were obtained.

$^1$H-NMR (CDCl$_3$): 1.23 (t, 3H), 1.51 (s, 9H), 1.56 (s, 9H), 2.54 (m, 2H), 4.12 (q, 2H), 4.33 (dd, 1H), 7.05 (d, 1H), 7.11 (m, 2H), 7.21 (t, 1H), 7.37 (t, 1H), 7.42 (d, 2H), 7.90 (d, 1H), 8.03 (s, 1H), 10.25 (s, 1H), 11.80 (s, 1H).

II.2    3-{2-[(3-(Guanidino)benzoyl)amino]acetamido}-3-phenyl-propanoic acid trifluoroacetate

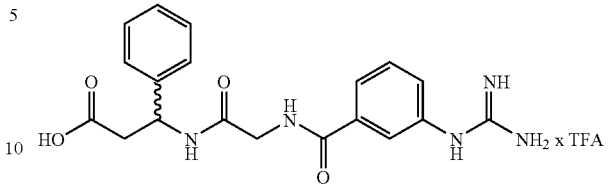

II.2a: □-Phenylalanine

Benzaldehyde (111 g) was dissolved in isopropanol (1 l) and heated under reflux for 5 h with ammonium acetate (98 g) and malonic acid (132 g). The solution was filtered hot and washed with hot isopropanol, and the precipitate was dried in vacuo. A white solid was obtained (yield: 93 g).

$^1$H-NMR (D$_4$-MeOH, CDCl$_3$): 2.68 (dd, 1H), 2.75 (dd, 1H), 4.48 (dd, 1H), 7.36–7.45 (m, 5H).

II.2b: Ethyl 3-amino-3-phenylpropanoate

β-Phenylalanine from II.2a (93) was suspended in ethanol (1.5 l) and the solution was saturated with gaseous HCl at room temperature. It was then heated under reflux for 4 h and stirred overnight at room temperature. The solution was cooled to 5° C. and filtered with suction. The filtrate was concentrated in vacuo, and the residue was washed with ether and dried. A white solid was obtained (yield: 52 g).

$^1$H-NMR (D$_6$-DMSO): 1.08 (t, 3H), 2.98 (dd, 1H), 3.18 (dd, 1H), 3.99 (m, 2H), 4.57 (dd, 1H), 7.36–7.45 (m, 3H), 7.54 (d, 2H).

II.2c: Ethyl 3-(Boc-Glycinylamino)-3-phenylpropionate

Boc-Glycine-hydroxysuccinimide ester (5 g) was slowly added at 5° C. to a solution of II.2b (4.2 g) and triethylamine (5.1 ml) in 45 ml of THF. The solution was stirred at room temperature for 20 h, and the insoluble precipitate was removed by filtration and washed with THF. The collected solutions were concentrated, the residue was taken up in ethyl acetate and the mixture was washed with satd. NaHCO$_3$ solution and water. After drying (MgSO$_4$), it was concentrated and a viscous residue was obtained (yield: 6.3 g).

$^1$H-NMR (CDCl$_3$): 1.16 (t, 3H), 1.45 (s, 9H), 2.82 (dd, 1H), 2.92 (dd, 1H), 3.81 (m, 2H), 4.06 (q, 2H), 5.17 (m, 1H), 5.43 (s, 1H), 7.23–7.38 (m, 5H).

II.2d: Ethyl 3-(glycinylamino)-3-phenylpropionate

A solution of HCl in dioxane (20 ml, 4 M) was added to a solution of ethyl 3-(Boc-glycinylamino)-3-phenylpropionate from II.2c (3.2 g) in dioxane (15 ml). After a reaction time of 16 h, the mixture was concentrated and a viscous oil was obtained (yield: 2.46 g).

$^1$H-NMR (CDCl$_3$): 1.04 (t, 3H), 2.70 (dd, 1H), 2.91 (dd, 1H), 3.65 (m, 1H), 3.88 (m, 1H), 3.93 (m, 2H), 5.32 (m, 1H), 7.12 (m, 1H), 7.18 (m, 2H), 7.36 (d, 2H), 7.80 (br. s, 3H), 8.93 (d, 1H).

II.2e: Ethyl 3-{2-[(3-(guanidino)benzoyl)amino]acetamido}-3-phenyl-propanoate N-Methylmorpholine (0.95 ml) and isobutyl chloroformate (1.1 ml) were added at 0° C. to a solution of 3-guanidinobenzoic acid hydrochloride in DMF (30 ml). A solution of ethyl 3-(glycinylamino)-3-phenylpropionate from II.2d (2.46 g) and N-methylmorpholine (1.9 ml) in 30 ml of DMF was then added and the mixture was stirred overnight at room temperature. The reaction mixture was then concentrated in vacuo and purified by chromatography (methylene chloride/methanol (5:1)). A viscous product was obtained (yield: 3.2 g).

MS (M+H$^+$): 411.

II.2: 3-{2-[(3-(Guanidino)benzoyl)amino]acetamido}-3-phenyl-propanoic acid trifluoroacetate LiOH x H$_2$O (775 mg) was added to a solution of ethyl 3-{2-[(3-(guanidino)benzoyl)amino]acetamido}-3-phenyl-propanoate from II.1-E (2.0 g) in 100 ml of water and the mixture was stirred at room temperature for 1 h. It was then neutralized with trifluoroacetic acid and concentrated. After purification by HPLC, a white solid was obtained (yield: 1.4 g).

$^1$H-NMR (D$_6$-DMSO): 2.45 (m, 2H), 3.88 (m, 2H), 5.07 (m, 1H), 7.13 (m, 1H), 7.23 (m, 3H), 7.31 (d, 2H), 7.43 (t, 1H), 7.64 (m, 2H), 8.99 (t, 1H), 9.20 (d, 1H).

Compound II.3: 3-{2-[(3-(Amino)benzoyl)amino]acetamido}-3-phenylpropanoic acid trifluoroacetate

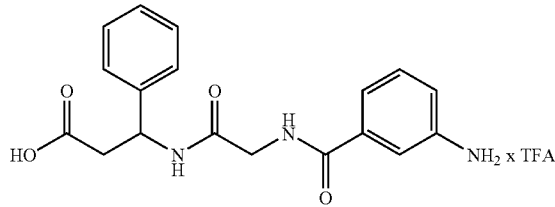

II.3a: Ethyl 3-{2-[(3-(nitro)benzoyl)amino]acetamido}-3-phenyl-propanoate 3-Nitrobenzoyl chloride (1.5 g) and diisopropylethylamine (2.1 g) were added to a solution of ethyl 3-(glycinylamino)-3-phenylpropionate from II.2d (2.28 g) in dioxane (50 ml) and the mixture was stirred overnight. It was then treated with water, extracted with ether, dried (MgSO$_4$) and concentrated. After chromatographic purification (methylene chloride/methanol (5:1)), a yellow solid was obtained (yield: 2.78 g).

$^1$H-NMR (CDCl$_3$): 1.07 (t, 3H), 2.87 (dd, 1H), 2.93 (dd, 1H), 4.09 (q, 2H), 4.17 (dd, 1H), 4.24 (dd, 1H), 5.45 (m, 1H), 7.23–7.38 (m, 7H), 7.64 (t, 1H), 8.16 (d, 1H), 8.38 (d, 1H), 8.69 (s, 1H).

II.3b: Ethyl 3-{2-[(3-(amino)benzoyl)amino]acetamido}-3-phenyl-propanoate

A solution of ethyl 3-{2-[(3-(nitro)benzoyl)amino]acetamido}-3-phenyl-propanoate from II.3a (2.7 g) in 100 ml of ethanol was treated with Tin(II) chloride (7.6 g) and heated under reflux for 3 h. The reaction mixture was then added to ice, rendered neutral with NaHCO$_3$ solution and filtered through Celite. The filtrate was extracted with methylene chloride, dried (MgSO$_4$) and concentrated. Chromatographic purification (purification (methylene chloride/methanol (5:1)) yielded the product (yield: 2.0 g).

$^1$H-NMR (CDCl$_3$): 1.05 (t, 3H), 2.83 (dd, 1H), 2.92 (dd, 1H), 3.80 (br, s, 2H), 4.06 (q, 2H), 4.16 (m, 2H), 5.44 (m, 1H), 6.80 (d, 1H), 6.92 (m, 1H), 7.10–7.35 (m, 9H).

II.3: 3-{2-[(3-(Amino)benzoyl)amino]acetamido}-3-phenyl-propanoic acid trifluoroacetate LiOH x H$_2$O (648 mg) was added to a solution of ethyl 3-{2-[(3-(amino)-benzoyl)amino]acetamido}-3-phenyl-propanoate from II.3b (1.5 g) in 300 ml of water and the mixture was stirred at room temperature for 24 h. It was then neutralized with trifluoroacetic acid and concentrated. After chromatographic purification (methylene chloride/methanol (2:1)), a solid was isolated. This was taken up in ethanol, filtered and a white solid was obtained after concentration of the filtrate (yield: 1.4 g).

$^1$H-NMR (D$_4$-MeOH): 2.77 (m, 2H), 4.03 (m, 2H), 5.39 (m, 1H), 6.86 (m, 1H), 7.14 (m, 2H), 7.23 (m, 1H), 7.30 (t, 2H), 7.36 (2H).

Compound II.4: 3-Benzenesulphonylamino-3-(3-(3-amino)-benzenesulphonylamino)-phenyl]-3-propanoic acid

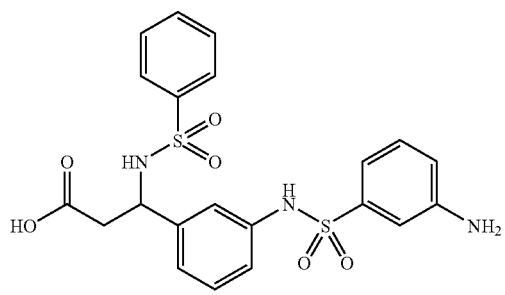

II.4a: Ethyl 3-benzenesulphonylamino-3-(3-nitrophenyl)-propionate

Phenylsulphonyl chloride (8.1 g) was added at 0° C. to a solution of ethyl 3-amino-3(3-nitrophenyl)-propionate hydrochloride from II.1b (10 g) in 100 ml of pyridine. After a reaction time of 15 min, triethylamine (6.3 ml) was added and the mixture was stirred at room temperature. After 5 h, it was concentrated, the residue was treated with 1 N HCl, the mixture was extracted with dichloromethane, and the extract was dried (MgSO$_4$) and concentrated. Chromatography (dichloromethane/methanol (5:1)) yielded a white solid (yield: 11.4 g).

$^1$H-NMR (CDCl$_3$): 1.16 (t, 3H), 2.80 (m, 2H), 4.05 (q, 2H), 4.87 (q, 1H), 6.06 (d, 1H), 7.35–7.50 (m, 5H), 7.71 (d, 2H), 7.92 (s, 1H), 8.03 (d, 1H).

II.4b: Ethyl 3-benzenesulphonylamino-3-(3-aminophenyl)-propionate

Tin(II) chloride (4.77 g) was added to a solution of ethyl 3-benzenesulphonylamino3-(3-nitrophenyl)-propionate from II.4a (2.0 g) in 60 ml of ethanol and the reaction mixture was heated under reflux for 2 h. After cooling, the solution was hydrolysed on ice and an NaHCO$_3$ solution (5%) was added to pH=8. The mixture was then extracted with dichloromethane, and the org. phase was washed with NaCl, dried (MgSO$_4$) and concentrated. A yellow oil was obtained (yield: 1.79 g).

$^1$H-NMR (CDCl$_3$): 1.14 (t, 3H), 2.72 (dd, 1H), 2.81 (dd, 1H), 4.02 (q, 2H), 4.65 (q, 1H), 5.66 (d, 1H), 6.41 (m, 1H), 6.48 (m, 2H), 6.96 (t, 1H), 7.40 (m, 2H), 7.50 (m, 1H), 7.75 (m, 2H).

II.4c: Ethyl 3-benzenesulphonylamino-3-(3-[3-nilrophenyl-sulphonylamino]-phenyl)-propionate 3-Nitrobenzenesulphonyl chloride (382 mg) was added at 0° C. to a solution of ethyl 3-benzenesulphonylamino-3-(3-aminophenyl)-propionate from II.4b (500 mg) in 4 ml of pyridine. After a reaction time of 1 h at 0° C. and 2 h at room temperature, the mixture was concentrated, the residue was treated with 1 N HCl and the mixture was extracted with dichloromethane. After drying (MgSO₄), the solvent was removed and a solid was obtained (yield: 649 mg).

¹H-NMR (CDCl₃): 1.02 (t, 3H), 2.50 (dd, 1H), 2.59 (dd, 1H), 3.88 (q, 2H), 4.52 (q, 1H), 5.70 (d, 1H), 6.49 (s, 1H), 6.82–6.90 (m, 3H), 7.06 (t, 1H), 7.34 (t, 2H), 7.44 (t, 1H), 7.59 (t, 1H), 7.64 (d, 2H), 7.96 (d, 1H), 8.31 (d, 1H), 8.49 (m, 1H).

II.4d: Ethyl 3-benzenesulphonylamino-3-(3-[3-aminophenylsulphonylamino]-phenyl)-propionate Tin(II) chloride (1.27 g) was added to a solution of ethyl 3-benzenesulphonylamino-3-(3-[3-nitrophenylsulphonylamino]-phenyl)-propionate from II.4c (600 mg) in 9 ml of ethanol, and the reaction mixture was heated under reflux for 2 h. After cooling, the solution was hydrolysed on ice and neutralized (pH=8) using NaHCO₃ solution (5%). It was then extracted with dichloromethane, and the organic phase was washed with NaCl, dried (MgSO₄) and concentrated. A yellow, viscous residue was obtained (yield: 394 mg).

¹H-NMR (CDCl₃): 1.14 (t, 3H), 2.65 (dd, 1H), 2.73 (dd, 1H), 4.01 (q, 2H), 4.63 (q, 1H), 5.81 (d, 1H), 6.32 (s, 1H), 6.79 (d, 2H), 6.88 (d, 1H), 6.99 (t, 1H), 7.05–7.14 (m, 3H), 7.22 (t, 1H), 7.39 (m, 2H), 7.51 (t, 1H), 7.71 (d, 2H).

II.4: 3-Benzenesulphonylamino-3-(3-[3-aminophenylsulphonylamino]-phenyl)-propionic acid 100 mg (0.2 mmol) of ethyl 3-benzenesulphonylamino-3-(3-[3-aminophenyl-sulphonylamino]-phenyl)-propionate from II.4d are dissolved in 10 ml of THF/water 1:1 and treated with 200 μl of a 2M lithium hydroxide solution and stirred overnight. The solvent is evaporated and the residue is precipitated from dichloromethane/methanol using ether.

Yield: 82 mg (87%) [TLC: acetonitrile/water 1:1) R$_f$=0.5].

II.5: (2S)-3-[4-(3-aminophenyl)-phenyl]-2-[(S)-camphor-10-sulphonamido]-propionic acid

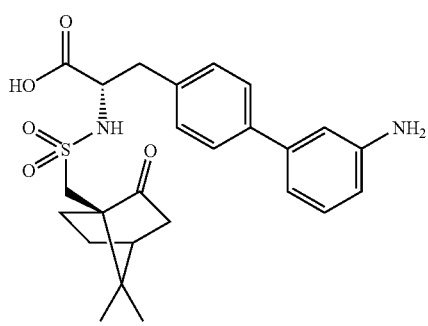

1200 mg of polystyrene Wang resin (loading 1.08 mmol/g) are swollen in DMF. The solvent is filtered off with suction and a solution of 1100 mg of (2S)-3-(4-bromophenyl)-2-(9-fluorenylmethoxycarbonylamino)-propionic acid in 15 ml of DMF is added. After shaking at room temperature for 15 min, the suspension is treated with 350 μl of pyridine and 540 mg of 2,6-dichlorobenzoyl chloride. It is shaken overnight at room temperature. The resin is then washed with DMF, MeOH and DCM.

The resin is treated with 20 ml of a 20% strength piperidine solution in DMF and shaken at room temperature for 10 min. It was then washed 3 times with DMF and 20 ml of a 20% strength piperidine solution in DMF are added again. After shaking for 20 min, it is washed with DMF and THF. The resin is treated with a solution of 1200 μl of DIEA in 10 ml of THF and a solution of 1750 mg of 2,4,6-(S)-camphor-10-yl-sulphonyl chloride in 10 ml of THF. It is shaken overnight at room temperature. The resin is then washed with DMF, MeOH and THF.

The resin is suspended in 7000 μl of xylene, treated with 1080 mg of 3-nitrobenzeneboronic acid and a solution of 1370 mg of sodium carbonate in 6000 μl of water and shaken at room temperature for 5 min. 230 mg of bis-(triphenylphosphine)-palladium(II) chloride and 170 mg of triphenylphosphine are then added and the mixture is stirred at 85° C. overnight. The resin is then washed with THF/water 1:1, 0.25 M aqueous hydrochloric acid, water, DMF, MeOH, THF and DCM. The resin is treated with a solution of 5400 mg of Tin(II) chloride dihydrate in 12 ml of NMP and shaken overnight at room temperature. The resin is then washed with NMP, MeOH, THF and DCM.

For the removal of the product, the resin is shaken with 12 ml of TFA/DCM for 1 h and filtered off, and the filtrate is concentrated in vacuo. The crude product II.5 is reacted further in the coupling reactions.

II.6 3-[4-(3-Propylaminocarbonylamino-phenyl)-phenyl]-2-amino-propionic acid

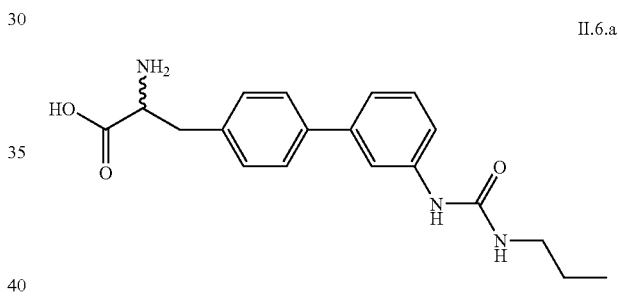

II.6.a

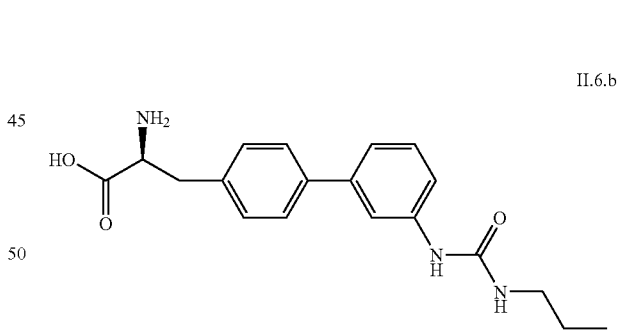

II.6.b 1.2 g of polystyrene Wang resin (loading 1.08 mmol/g) are swollen in DMF. The solvent is filtered off with suction and a solution of 1.1 g of (2S)-3-(4-bromophenyl)-2-(9-fluorenylmethoxycarbonylamino)-propionic acid (for the synthesis of II.6.b) in 2 ml of DMF is added. After shaking at room temperature for 15 min, the suspension is treated with 350 μl of pyridine and 540 mg of 2,6-dichlorobenzoyl chloride. It is shaken overnight at room temperature. The resin is then washed with DMF, MeOH and DCM.

The resin is suspended in 7000 μl of xylene, treated with 1080 mg of 3-nitrobenzeneboronic acid and a solution of 1370 mg of sodium carbonate in 6000 μl of water and shaken at room temperature for 5 min. 230 mg of bis-(triphenylphosphine)-palladium(II) chloride and 170 mg of triphenylphosphine are then added and the mixture is stirred at 85° C. overnight. The resin is then washed with THF/water 1:1, 0.25 M aqueous hydrochloric acid, water, DMF, MeOH, THF and DCM. The resin is treated with a solution of 540 mg of Tin(II) chloride dihydrate in 12 ml of NMP and shaken overnight at room temperature. The resin is then washed with NMP, MeOH, THF and DCM.

The resin is treated with a solution of 570 µl of DIEA in 13 ml of THF/DCM 1:1 and a solution of 3130 mg of 4-nitrophenylchloroformic acid ester in 13 ml of THF/DCM 1:1. After shaking at room temperature for 45 min, it is washed with THF and DMF and a solution of 1.1 g of propylamine and 3.16 ml of DIEA in 24 ml of NMP is added. After shaking for 10 h, the resin is washed with DMF, MeOH, THF and DCM.

For the removal of the product, the resin is shaken for for 1 h with 10 ml of TFA/DCM and filtered off, and the filtrate is concentrated in vacuo. The crude product II.6 is reacted further in the coupling reactions.

II.7 3-[3-(3-(Benzimidazol-2-yl-aminocarbonylamino)-phenyl)-phenylsulphonamido]-3-(3-amino-phenyl)-propionic acid

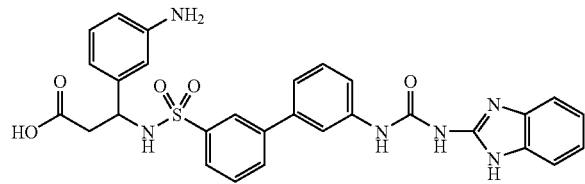

1.2 g of polystyrene Wang resin (loading 1.08 mmol/g) are swollen in DMF. The solvent is filtered off with suction and a solution of 841 mg of (3R,S)-3-fluorenyl-methoxycarbonylamino-3-(3-nitrophenyl)-propionic acid (amino acid reagent) in 15 ml of DMF are added. After shaking at room temperature for 15 min, the suspension is treated with 350 µl of pyridine and 540 mg of 2,6-dichlorobenzoyl chloride. It is shaken overnight at room temperature. The resin is then washed with DMF, MeOH and DCM.

The resin is treated with 15 ml of a 20% strength piperidine solution in DMF and shaken at room temperature for 10 min. It is then washed 3 times with DMF and 15 ml of a 20% strength piperidine solution in DMF are added again. After shaking for 20 min, it is washed with .DMF and THF. The resin is treated with a solution of 450 µl of DIEA in 500 µl of THF and a solution of 430 mg of 3-bromobenzene-sulphonyl chloride (sulphonylating reagent) in 500 µl of THF. It is shaken overnight at room temperature. The resin is then washed with DMF, MeOH and THF.

The resin is suspended in 9000 µl of xylene, treated with 1250 mg of 3-aminobenzeneboronic acid monohydrate and a solution of 1940 mg of sodium carbonate in 9000 µl of water and shaken at room temperature for 5 min. 200 mg of bis-(triphenylphosphine)-palladium(II) chloride and 150 mg of triphenylphosphine are then added and the mixture is stirred at 85° C. overnight. The resin is then washed with THF/water 1:1, 0.25 M aqueous hydrochloric acid, water, DMF, MeOH, THF and DCM.

The resin is treated with a solution of 500 µl of DIEA in 12 ml of THF/DCM 1:1 and a solution of 2757 mg of 4-nitrophenylchloroformic acid ester in 12 ml of THF/DCM 1:1. After shaking at room temperature for 45 min, it is washed with THF and DMF and a solution of 2125 mg of 2-aminobenzimidazole (amine reagent) and 2780 µl of DIEA in 20 ml of NMP are added. After shaking for 10 h, the resin is washed with DMF, MeOH, THF and DCM. For the removal of the product, the resin is shaken with 12 ml of TFA/DCM for 1 h and filtered off, and the filtrate is concentrated in vacuo.

The crude product is taken up in methanol and reduced to the target product using hydrogen over palladium on active carbon. Chromatographic purification is carried out on silica gel using dichloromethane/methanol/ammonia (17% strength) (15:4:0.4). [TLC: (acetonitrile/water/glacial acetic acid 10:1:0.1), $R_f$=0.5]. [MALDI-MS: m/e=571 (M+H)$^+$].

II.8 3-[4-(3-(Benzimidazol-2-yl-aminocarbonylamino)-phenyl)-phenylsulphonamido]-3-(3-amino-phenyl)-propionic acid

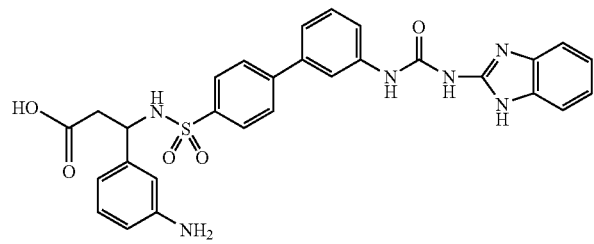

The preparation is carried out analogously to II.7 using 4-bromosulphonyl chloride as a sulphonylating reagent. Chromatographic purification of the target product is carried out on silica gel using dichloromethane/methanol/ammonia (17% strength) (15:2:0.2).

[TLC: (dichloromethane/methanol/ammonia (17% strength) (15:6:0.6); $R_f$=0.33]. [FAB-MS: m/e=571 (M+H)$^+$].

II.9: 2-[3-(3-(Benzimidazol-2-yl-aminocarbonylamino)-phenyl)-phenylsulphonamido]-3-(4-amino-phenyl)-propionic acid

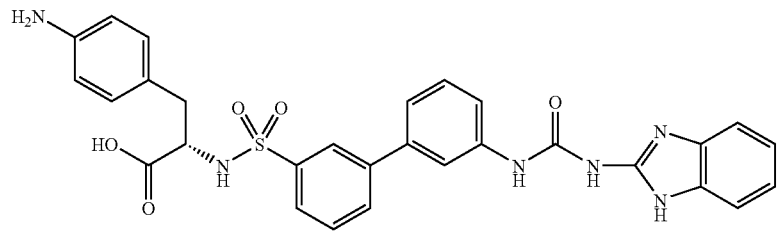

The preparation is carried out analogously to compound II.7 using 4-nitro-Phe(Fmoc) as an amino acid reagent. Chromatographic purification of the target product is carried out on silica gel using dichloromethane/methanol/ammonia (17% strength) (15:2:0.2).

[TLC: (dichloromethane/methanol/ammonia (17% strength) (15:4:0.5); $R_f$=0.25]. [FAB-MS: m/e=571 $(M+H)^+$].

II.10 2-[3-(3-(Benzimidazol-2-yl-aminocarbonylamino)-phenyl)-6-methoxy-phenylsulphonamido]-3-(4-amino-phenyl)-propionic acid

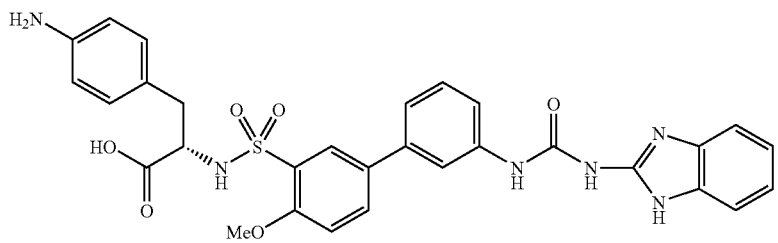

The preparation is carried out analogously to II.9 using 5-bromo-2-methoxy-benzenesulphonyl chloride as a sulphonylating reagent.

Chromatographic purification of the target product is carried out on silica gel using dichloromethane/methanol/ammonia (17% strength) (15:4:0.4).

[TLC: (acetonitrile/water/glacial acetic acid (10:1:0.1); $R_f$=0.46]. [MALDI-MS: m/e=601 $(M+H)^+$].

Compound II.11 2-[4-(3-(Benzimidazol-2-yl-aminocarbonylamino)-phenyl)phenylsulphonamido]-3-(4-amino-phenyl)-propionic acid

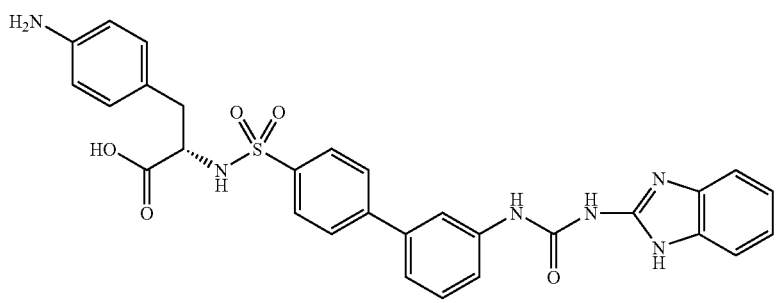

The preparation is carried out analogously to II.8 using 4-bromobenzenesulphonyl chloride as a sulphonylating reagent.

Chromatographic purification of the target product is carried out on silica gel using dichloromethane/methanol/ ammonia (17% strength) (15:2:0.2->15:4:0.4).

[TLC: (acetonitrile/water/glacial acetic acid (10:1:0.1); $R_f$=0.64]. [FAB-MS: m/e=571 (M+H)$^+$].

II.12  3-(4-Aminobenzenesulphonylamino)-3-[3-(propylaminocarbonylamino-phenylsulphonylamino)-phenyl]-propionic acid

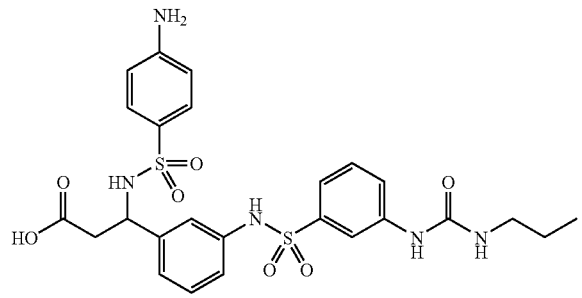

1.2 g of polystyrene Wang resin (loading 1.08 mmol/g) are swollen in DMF. The solvent is filtered off with suction and a solution of 841 mg of (3R,S)-3-(9-fluorenyl-methoxycarbonylamino)-3-(3-nitrophenyl)-propionic acid (amino acid reagent, prepared by protecting the free amino function of 3-amino-3-(3-nitrophenylpropionic acid with FMCO in a conventional and known manner) in 15 ml of DMF is added. After shaking at room temperature for 15 min, the suspension is treated with 350 µl of pyridine and 540 mg of 2,6-dichlorobenzoyl chloride. It is shaken overnight at room temperature. The resin is then washed with DMF, MeOH and DCM.

The resin is treated with a solution of 5400 mg of Tin(I) chloride dihydrate in 12 ml of NMP and shaken overnight at room temperature. The resin is then washed with NMP, MeOH, THF and DCM.

The resin is treated with a solution of 450 µl of DIEA in 500 µl of THF and a solution of 430 mg of 3-nitrobenzenesulphonyl chloride in 500 µl of THF. It is shaken overnight at room temperature. The resin is then washed with DMF, MeOH and THF.

The resin is treated with a solution of 5400 mg of Tin(II) chloride dihydrate in 12 ml of NMP and shaken overnight at room temperature. The resin is then washed with NMP, MeOH, THF and DCM.

The resin is treated with a solution of 500 µl of DIEA in 12 ml of THF/DCM 1:1 and a solution of 2757 mg of 4-nitrophenylchloroformic acid ester in 12 ml of THF/DCM 1:1. After shaking at room temperature for 45 min, it is washed with THF and DMF and a solution of 943 mg of propylamine and 2780 µl of DIEA in 20 ml of NMP is added. After shaking for 10 h, the resin is washed with DMF, MeOH, THF and DCM.

The resin is treated with a solution of 450 µl of DIEA in 500 µl of THF and a solution of 430 mg of 4-nitrobenzenesulphonyl chloride in 500 µl of THF. It is shaken overnight at room temperature. The resin is then washed with DMF, MeOH and THF.

The resin is treated with a solution of 5400 mg of Tin(II) chloride dihydrate in 12 ml of NMP and shaken overnight at room temperature. The resin is then washed with NMP, MeOH, THF and DCM.

For the removal of the product, the resin is shaken for 1 h with 12 ml of TFA/DCM and filtered off, and the filtrate is concentrated in vacuo.

II.13  3-Amino-3-[3-(propylaminocarbonylamino-phenylsulphonylamino)-phenyl]-propionic acid

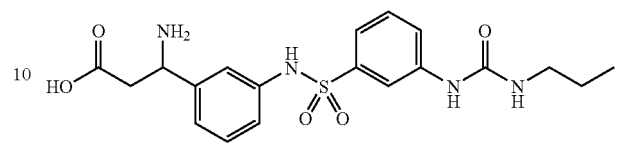

1.2 g of polystyrene Wang resin (loading 1.08 mmol/g) are swollen in DMF. The solvent is filtered off with suction and a solution of 841 mg of (3R,S)-3-(9-fluorenyl-methoxycarbonylamino)-3-(3-nitrophenyl)-propionic acid (amino acid reagent) in 15 ml of DMF are added. After shaking at room temperature for 15 min, the suspension is treated with 350 µl of pyridine and 540 mg of 2,6-dichlorobenzoyl chloride. It is shaken overnight at room temperature. The resin is then washed with DMF, MeOH and DCM.

The resin is treated with a solution of 5400 mg of Tin(II) chloride dihydrate in 12 ml of NMP and shaken overnight at room temperature. The resin is then washed with NMP, MeOH, THF and DCM.

The resin is treated with a solution of 450 µl of DIEA in 500 µl of THF and a solution of 430 mg of 3-nitrobenzenesulphonyl chloride in 500 µl of THF. It is shaken overnight at room temperature. The resin is then washed with DMF, MeOH and THF.

The resin is treated with a solution of 5400 mg of Tin(II) chloride dihydrate in 12 ml of NMP and shaken overnight at room temperature. The resin is then treated with NMP, MeOH, THF and DCM.

The resin is treated with a solution of 500 µl of DIEA in 12 ml of THF/DCM 1:1 and a solution of 2757 mg of 4-nitrophenylchloroformic acid ester in 12 ml of THF/DCM 1:1. After shaking at room temperature for 45 min, it is washed with THF and DMF and a solution of 943 mg of propylamine and 2780 µl of DIEA in 20 ml of NMP is added. After shaking for 10 h, the resin is washed with DMF, MeOH, THF and DCM.

For the removal of the product, the resin is shaken for 1 h with 12 ml of TFA/DCM and filtered off, and the filtrate is concentrated in vacuo.

II.14  3-(4-Aminobenzeneaminocarbonylamino)-3-[3-(guanidino-phenyl-sulphonylamino)-phenyl]-propionic acid trifluoroacetic acid

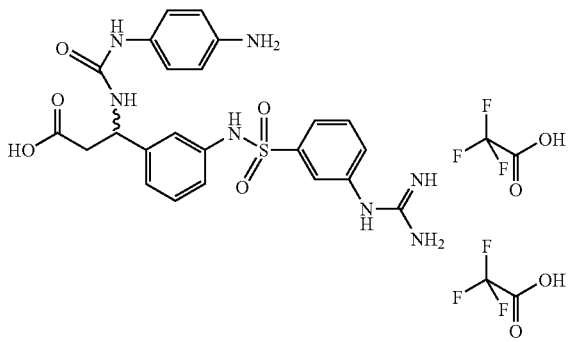

100 mg (0.165 mmol) of the compound II.1 are stirred with 1 equivalent of 4-nitrophenyl isocyanate for 3 h in 10 ml of DMF. The mixture is concentrated, and the residue is taken up in dichloromethane and precipitated using pentane. The intermediate a (106 mg; 83%) is dried.

120 mg (0.156 mmol) of the intermediate a are dissolved in methanol and hydrogenated over palladium/carbon. The catalyst is separated off, the solution is concentrated and the residue is lyophilized from dioxane/water (86 mg; 75% of intermediate b).

76 mg (0.1027 mmol) of the intermediate b are taken up in methanol and treated with 154 μl (3 eq.) of a 2M lithium hydroxide solution. After 6 h, a further 51 μl of the lithium hydroxide solution are added and the mixture is stirred for 2 days. It is concentrated, precipitated from dichloromethane using ether and intermediate c is thus obtained.

10 mg of the precipitated intermediate c are then taken up in 4 ml of dichloromethane and treated with 0.5 ml of trifluoroacetic acid. After 1.5 h, the mixture is concentrated and the residue is precipitated from dichloromethane/methanol using ether. 3 mg (30%) of the target compound are obtained.

[ESI-MS: m/e=512 (M+H)$^+$].

Compound II.15 2-(3-Aminobenzenesulphonylamino)-3-{4-[3-propylaminocarbonylamino)-phenyl)-phenyl]}-propionic acid

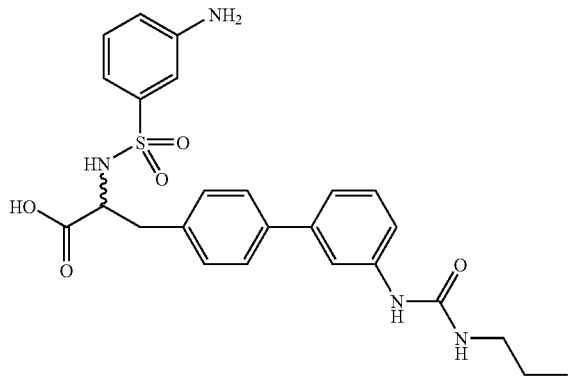

1.2 g of polystyrene Wang resin (loading 1.08 mmol/g) are swollen in DMF. The solvent is filtered off with suction and a solution of 1.1 g of (2R,S)-3-(4-bromophenyl)-2-(9-fluorenylmethoxycarbonylamino)-propionic acid in 2 ml of DMF is added. After shaking at room temperature for 15 min, the suspension is treated with 350 μl of pyridine and 540 mg of 2,6-dichlorobenzoyl chloride. It is shaken at room temperature overnight. The resin is then washed with DMF, MeOH and DCM.

The resin is suspended in 7000 μl of xylene, treated with 1080 mg of 3-nitrobenzeneboronic acid and a solution of 1370 mg of sodium carbonate in 6000 μl of water and shaken at room temperature for 5 min. 230 mg of bis-(triphenylphosphine)-palladium(II) chloride and 170 mg of triphenylphosphine are then added and the mixture is stirred overnight at 85° C. The resin is then washed with THF/water 1:1, 0.25 M aqueous hydrochloric acid, water, DMF, MeOH, THF and DCM. The resin is treated with a solution of 540 mg of Tin(II) chloride dihydrate in 12 ml of NMP and shaken overnight at room temperature. The resin is then washed with NMP, MeOH, THF and DCM.

The resin is treated with a solution of 570 μl of DIEA in 13 ml of THF/DCM 1:1 and a solution of 3130 mg of 4-nitrophenylchloroformic acid ester in 13 ml of THF/DCM 1:1. After shaking at room temperature for 45 min, it is washed with THF and DMF and a solution of 1.1 g of propylamine and 3.16 ml of DIEA in 24 ml of NMP is added. After shaking for 10 hours, the resin is washed with DMF, MeOH, THF and DCM.

The resin is treated with a solution of 590 μl of DIEA in 4.5 ml of THF and a solution of 997 mg of 3-nitrobenzenesulphonyl chloride in 4.5 ml of THF. It is shaken overnight at room temperature. The resin is then washed with DMF, MeOH and THF.

For the removal of the product, the resin is shaken with 10 ml of TFA/DCM for 1 h and filtered off, and the filtrate is concentrated in vacuo.

II.16 3-(4-Aminophenylaminocarbonylamino)-3-[3-(propylaminocarbonylamino-phenyl-sulphonylamino)-phenyl]-propionic acid

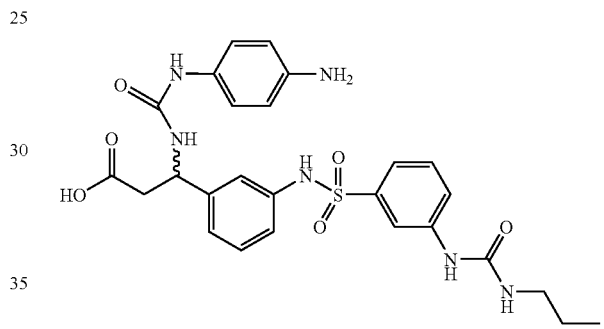

70 mg (0.166 mmol) of the compound II.13 are stirred with 54 mg (2 eq) of 4-nitrophenyl isocyanate for 1 h in 10 ml of DMF. The mixture is concentrated and the residue is purified by flash chromatography on silica gel using dichloromethane/methanol/ammonia 17% strength (15:2:0.2). After precipitation from dichloromethane/methanol using ether, the intermediate a (29 mg; 30%) is obtained.

This is dissolved in methanol and hydrogenated over palladium/carbon. The catalyst is separated off, the solution is concentrated and the residue is lyophilized from dioxane/water. 18 mg (74%) of the target compound are obtained.

Compound II.17 3-[3-(3-(Benzimidazol-2-yl-aminocarbonylamino)-phenyl)phenylsulphonamido]-3-(4-amino-phenyl)-propionic acid

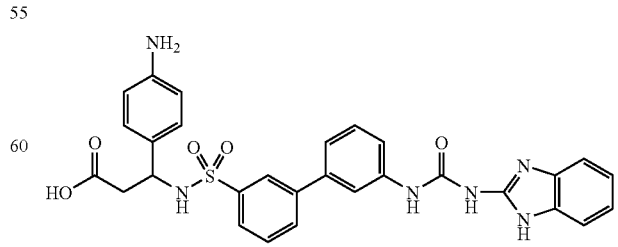

The preparation is carried out analogously to II.7 using (3R,S)-3-(9-fluorenylmethoxycarbonylamino)-3-(4-nitro phenyl)-propionic acid as amino acid reagent. The resin is then treated with a solution of 540 mg of Tin(II) chloride dihydrate in 12 ml of NMP and shaken overnight at room temperature. The resin is then washed with NMP, MeOH, THF and DCM.

For the removal of the product, the resin is shaken with 10 ml of TFA/DCM for 1 h and filtered off, and the filtrate is concentrated in vacuo.

Conjugates

1. Conjugates with Linkage Via the Carboxyl Function of the Non-Peptide Integrin Ligands Example 1.1

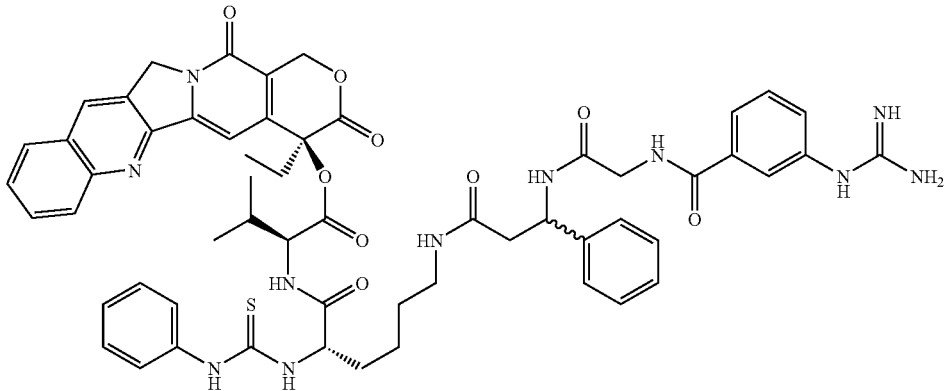

50 mg (0.07 mmol) of starting material I.12 and 27 mg (0.07 mmol) of starting material II.2 are initially introduced into 10 ml of DMF and treated with 46 µl of Hünig's base. 19 mg (0.1 mmol) of N-ethyl-N'-(dimethylaminopropyl)-carbodiimide hydrochloride and 14 mg (0.1 mmol) of hydroxybenzotriazole are added and the mixture is stirred overnight. A further 14 mg of N-ethyl-N'-(dimethylaminopropyl)carbodiimide hydrochloride are then added with cooling and the mixture is left in an ultrasonic bath for 4 h. It is concentrated, and the residue is stirred with water and filtered off. It is purified by flash chromatograpy on silica gel using dichloromethane/methanol/ammonia (17% strength) (15:3:0.3->15:8:0.8). After the isolation of the product, this is precipitated from dichloromethane/methanol using diethyl ether. 22 mg (29%) of the target product are obtained.

[TLC: (acetonitrile/water/glacial acetic acid (5:1:0.2); $R_f$=0.46]; [FAB-MS: m/e=1076 (M+H)$^+$].

Example 1.2

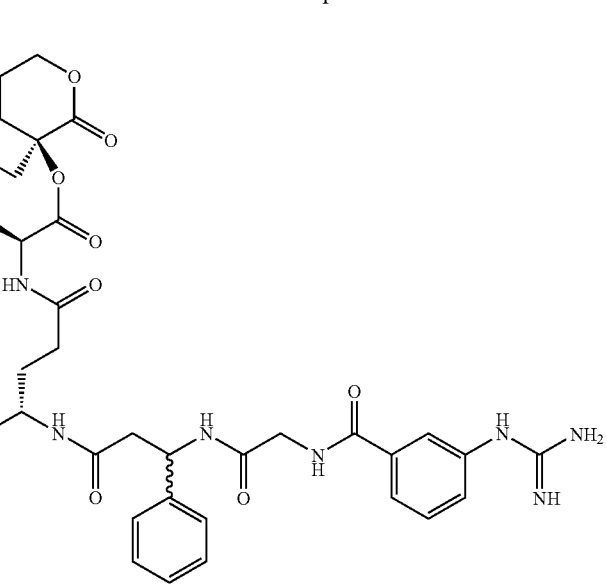

75 mg (0.096 mmol) of starting material I.2 and 37 mg (0.096 mmol) of starting material II.2 are initially introduced into 5 ml of DMF and treated with 65 µl of Hünig's base. 28 mg (1.5 eq) of N-Ethyl-N'-(dimethylaminopropyl)-carbodiimide hydrochloride and 20 mg (1.5 eq) of hydroxybenzotriazole are added and the mixture is stirred for 2 h. A further 14 mg of N-ethyl-N'-(dimethylaminopropyl)-carbodiimide hydrochloride are then added and the mixture is stirred overnight. It is concentrated and the product is precipitated from dichloromethane using diethyl ether. This purification operation is repeated twice. 48 mg (48%) are obtained.

[TLC: (acetonitrile/water/glacial acetic acid (5:1:0.2); $R_f$=0.5].

40 mg (0.039 mmol) of the intermediate are dissolved in 10 ml of dioxane/water 1:1 and hydrogenated over palladium-carbon using hydrogen. The catalyst is filtered off and the filtered solution is lyophilized. 35 mg (95%) of the target product are obtained.

[TLC: (acetonitrile/water/glacial acetic acid (5:1:0.2); $R_f$=0.25]. [FAB-MS: n/e=942 (M+H)$^+$].

2. Conjugates with Linkage Via the Guanidine Mimic Function

Example 2.1

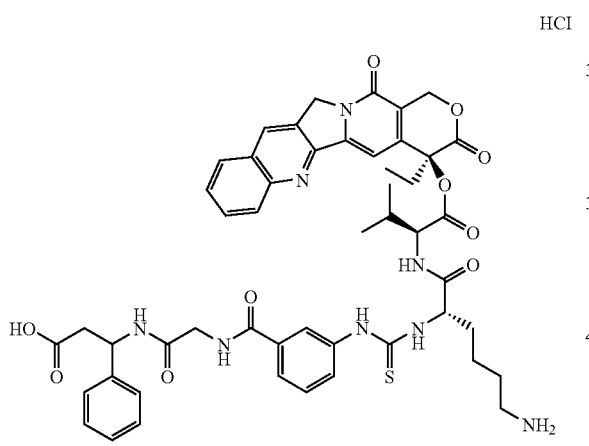

A solution of 50 mg (0.11 mmol) of the starting material II.3 in 5 ml of dioxane/water 1:1 is treated with 11.7 µl of thiophosgene (1.4 eq.) with stirring. After 20 min, the mixture is treated with 112 µl of ethyldiisopropylamine, stirred at room temperature for a further 5 min and then concentrated in vacuo. The residue is then taken up in S ml of DMF and 99 mg (1 eq) of starting material I.4 and 371 µl of Hünig's base are added and the mixture is stirred at room temperature for 1 h. It is then concentrated in vacuo, and the residue is taken up in dichloro-methane/methanol and precipitated using diethyl ether. It is purified by flash chromatography on silica gel using dichloromethane/methanol/ammonia (17% strength) (15:2:0.2). 58 mg (45%) of the intermediate are obtained.

[TLC: (acetonitrile/water/glacial acetic acid (5:1:0.2); $R_f$=0.67].

53 mg (0.045 mmol) of this Fmoc-protected intermediate are deprotected using 250 µl of piperidine in 5 ml of DMF. After precipitating twice from dichloromethane/methanol using diethyl ether, the target product is obtained, which isthen taken up in dioxane/water and converted into thehydrochloride using one equivalent of a 0.1 M HCl solution. The solution which remains is lyophilized. 35 mg (79%) of the target product are obtained.

[TLC: (acetonitrile/water/glacial acetic acid (5:1:0.2); $R_f$=0.35]. [FAB-MS: m/e=959 (M+H)$^+$].

Example 2.2

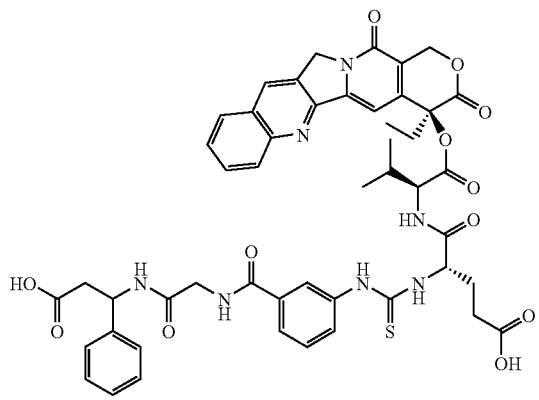

A solution of 50 mg (0.11 mmol) of the starting material II.3 in 5 ml of dioxane/water 1:1 is treated with 11.7 µl of thiophosgene (1.4 eq.) with stirring. After 20 min, the mixture is treated with 112 µl of ethyldiisopropylamine, stirred for a further 5 min at room temperature and then concentrated in vacuo. It is then taken up in 10 ml of DMF and 75 mg (1 eq) of starting material I.5 and 37 µl of Hünig's base are added and the mixture is stirred at room temperature for 2 h. It is then concentrated in vacuo, and the residue is taken up in dichloromethane/methanol and precipitated using diethyl ether. The residue is stirred with water. It is filtered off with suction and, after drying in a high vacuum, 68 mg (65%) of the target product are obtained.

[FAB-MS: m/e=960 (M+H)$^+$].

Example 2.3

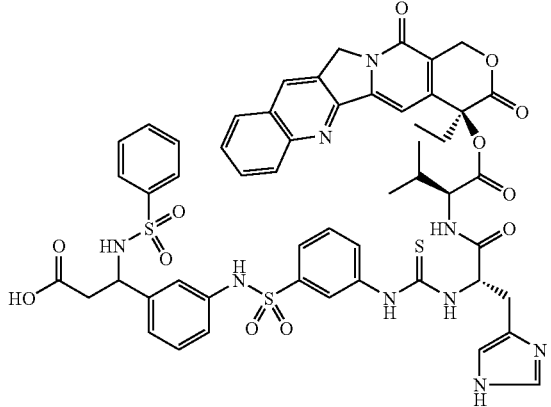

A solution of 80 mg (0.168 mmol) of the starting material II.4 in 10 ml of dioxane/water 1:1 is treated with 18 µl of thiophosgene (1.4 eq.) with stirring. After 30 min, the mixture is treated with 115 µl of ethyldiisopropylamine, stirred for a further 5 min at room temperature and then concentrated in vacuo. It is then taken up in 10 ml of DMF and 136 mg (1 eq) of starting material I.3 and 57 µl of Hünig's base are added and the mixture is stirred overnight at room temperature. It is then concentrated in vacuo and the residue is stirred with water. It is filtered off with suction and, after drying in a high vacuum, purified by flash chromatography on silica gel using dichloromethane/methanol/

Example 2.4

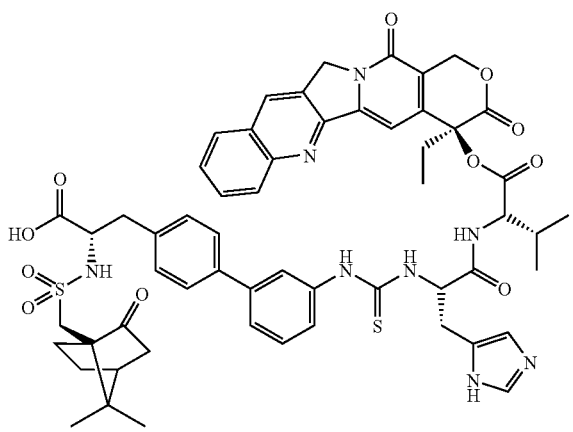

A solution of 100 mg (0.212 mmol) of the starting material II.5 in 10 ml of dioxane/water 1:1 is treated with 23 μl of thiophosgene (1.4 eq.) with stirring. After 30 min, the mixture is treated with 109 μl of ethyldiisopropylamine, stirred for a further 5 min at room temperature and then concentrated in vacuo. It is then taken up in 20 ml of DMF and 172 mg (1 eq) of starting material I.3 and 145 μl of Hünig's base are added and the mixture is at room temperature for 4 h. It is then concentrated in vacuo and the residue is purified by flash chromatography on silica gel using dichloromethane/methanol/ammonia (17% strength) (15:2: 0.2). The corresponding fractions are isolated and 87 mg (37%) of the target product are obtained.

[TLC: (dichloromethane/methanol/ammonia (17% strength) (15:3:0.3); $R_f$=0.2]. [ESI-MS: m/e=1097 (M+H)$^+$].

ammonia (17% strength) (15:2:0.2). The corresponding fractions are isolated, taken up in dioxane/water and, after lyophilization, 75 mg (41%) of the target product are obtained.

[TLC: (acetonitrile/water/glacial acetic acid (5:1:0.2); $R_f$=0.6]. [FAB-MS: m/e=1102 (M+H)$^+$].

Example 2.5

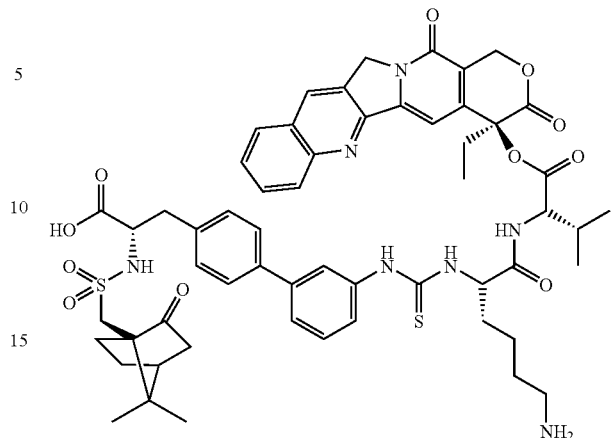

This product is prepared in analogy to Example 2.4 starting from the starting materials I.4 and II.5 with subsequent Fmoc removal.

Yield: 21% (Fmoc-protected intermediate) [TLC: (dichloromethane/methanol/ammonia (17% strength) (15:3:0.3); $R_f$=0.28]. Yield: 69% (final stage) [TLC: (dichloromethane/methanol/ammonia (17% strength) (15:3:0.3); $R_f$=0.39]. [FAB-MS: m/e=1088 (M+H)$^+$].

General Comments on Examples 2.6–2.14

All retention times are indicated in minutes and were determined by HPLC on an RP column (Eurospher 100, C18, ID 4 mm) by UV absorption. An eluent mixture of 0.1% strength acetonitrile/water was used with the following method: 0 min.=10% acetonitrile, 13 min.=80% acetonitrile, 15 min.=80% acetonitrile, 17 min.=10% acetonitrile.

The mass determinations were carried out by HPLC-MS using the electron spray ionization (ESI) method.

Example 2.6

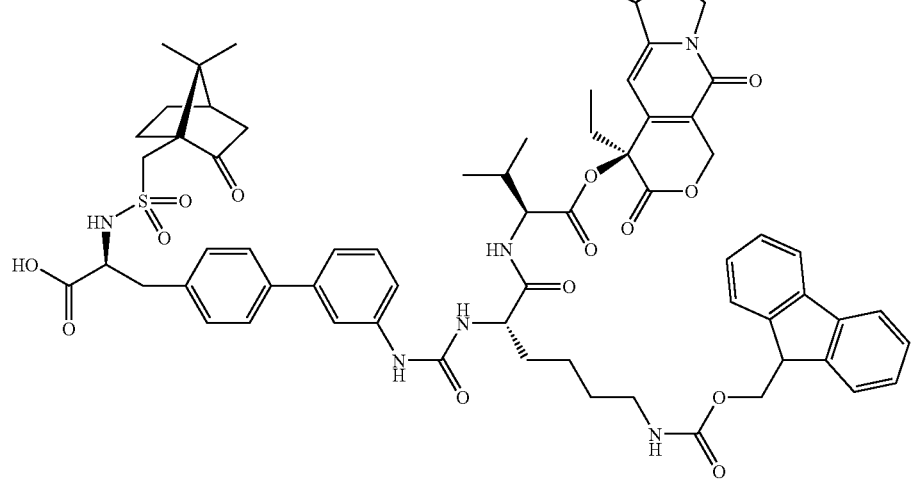

120 mg of polystyrene Wang resin (loading 1.08 mmol/g) are swollen in DMF. The solvent is filtered off with suction and a solution of 110 mg of (2S)-3-(4-bromophenyl)-2-(9-fluorenylmethoxycarbonylamino)-propionic acid in 1.5 ml of DMF is added. After shaking at room temperature for 15 min, the suspension is treated with 35 µl of pyridine and 54 mg of 2,6-dichlorobenzoyl chloride. It is shaken overnight at room temperature. The resin is then washed with DMF, MeOH and DCM.

The resin is treated with 2 ml of a 20% strength piperidine solution in DMF and shaken at room temperature for 10 min. It is then washed 3 times with DMF and 2 ml of a 20% strength piperidine solution in DMF are added again. After shaking for 20 min, it is washed with DMF and THF. The resin is treated with a solution of 120 µl of DIEA in 1 ml of THF and a solution of 175 mg of 2,4,6-(S)-camphor-10-yl-sulphonyl chloride in 1 ml of THF. The mixture is shaken overnight at room temperature. The resin is then washed with DMF, MeOH and THF.

The resin is suspended in 700 µl of xylene, treated with 108 mg of 3-nitrobenzeneboronic acid and a solution of 137 mg of sodium carbonate in 600 µl of water and shaken at room temperature for 5 min. 23 mg of bis-(triphenylphosphine)palladium(II) chloride and 17 mg triphenylphosphine are then added and the mixture is stirred at 85° C. overnight. The resin is then washed with THF/water 1:1, 0.25 M aqueous hydrochloric acid, water, DMF, MeOH, THF and DCM. The resin is treated with a solution of 540 mg of Tin(II) chloride dihydrate in 1.2 ml of NMP and shaken overnight at room temperature. The resin is then washed with NMP, MeOH, THF and DCM.

The resin is treated with a solution of 57 µl of DIEA in 1.3 ml of THF/DCM 1:1 and a solution of 313 mg of 4-nitrophenylchloroformic acid ester in 1.3 ml of THF/DCM 1:1. After shaking at room temperature for 45 min, it is washed with THF and DMF and a solution of 260 mg of starting material I.4 (amine reagent) and 135 µl of DIEA in 800 µl of NMP is added. After shaking for 10 h, the resin is washed with DMF, MeOH, THF and DCM. For the removal of the product, the resin is shaken for 1 h with 2 ml of TFA/DCM and filtered off, the filtrate is concentrated in vacuo and the residue is purified on silica gel. 19 mg of the title compound are obtained.

ESI: 1294. $R_t$=13.2

Example 2.7

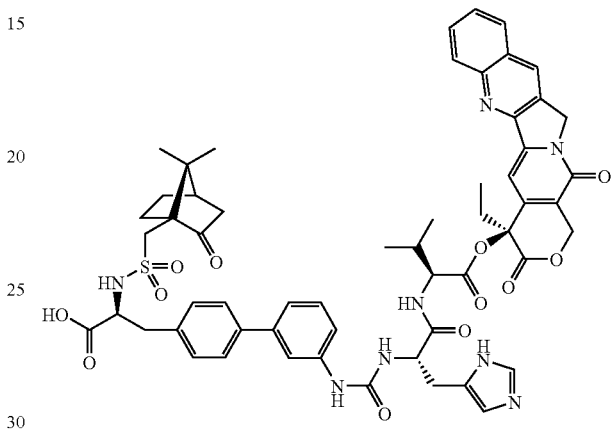

This product is prepared in analogy to Example 2.6 using starting material I.3 as an amine reagent.

ESI: 1081, $R_t$=9.5

Example 2.8

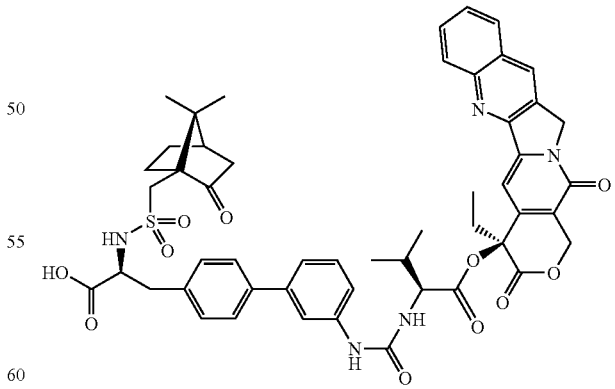

This product is prepared in analogy to Example 2.6 using starting material I.1 as an amine reagent.

ESI: 944, $R_t$=11.5

Example 2.9

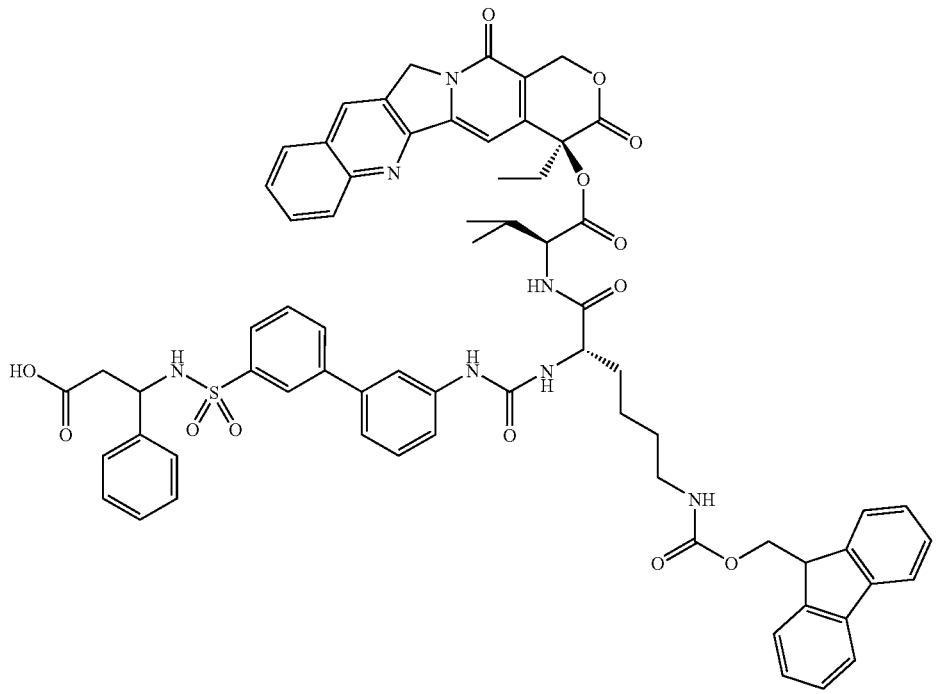

120 mg of polystyrene Wang resin (loading 1.08 mmol/g) are swollen in DMF. The solvent is filtered off with suction and a solution of 90 mg of (3R,S)-3-(9-fluorenyl-methoxycarbonylamino)-3-phenyl-propionic acid (amino acid reagent) in 1.5 ml of DMF is added. After shaking at room temperature for 15 min, the suspension is treated with 35 µl of pyridine and 54 mg of 2,6-dichlorobenzoyl chloride. It is shaken overnight at room temperature. The resin is then washed with DMF, MeOH and DCM.

The resin is treated with 1.5 ml of a 20% strength piperidine solution in DMF and shaken at room temperature for 10 min. It is then washed 3 times with DMF and 1.5 ml of a 20% strength piperidine solution in DMF is added again. After shaking for 20 min, it is washed with DMF and THF. The resin is treated with a solution of 45 µl of DIEA in 500 µl of THF and a solution of 43 mg of 3-bromobenzenesulphonyl chloride (sulphonylating reagent) in 500 µl of THF. It is shaken overnight at room temperature. The resin is then washed with DMF, MeOH and THF.

The resin is suspended in 700 µl of xylene, treated with 108 mg of 3-nitrobenzeneboronic acid and a solution of 137 mg of sodium carbonate in 600 µl of water and shaken at room temperature for 5 min. 23 mg of bis-(triphenylphosphine)-palladium(II) chloride and 17 mg of triphenylphosphine are then added and the mixture is stirred at 85° C. overnight. The resin is then washed with THF/water 1:1, 0.25 M aqueous hydrochloric acid, water, DMF, MeOH, THF and DCM. The resin is treated with a solution of 540 mg of Tin(II) chloride dihydrate in 1.2 ml of NMP and shaken overnight at room temperature. The resin is then washed with NMP, MeOH, THF and DCM.

The resin is treated with a solution of 57 µl of DIEA in 1.3 ml of THF/DCM 1:1 and a solution of 313 mg of 4-nitrophenylchloroformic acid ester in 1,3 ml of THF/DCM 1:1.

After shaking at room temperature for 45 min, it is washed with THF and DMF and a solution of 260 mg of starting material I.4 (amine reagent) and 135 µl of DIEA in 800 µl of NMP is added. After shaking for 10 h, the resin is washed with DMF, MeOH, THF and DCM. For the removal of the product, the resin is shaken with 2 ml of TFA/DCM for 1 h and filtered off, the filtrate is concentrated in vacuo and the residue is purified on silica gel. 18 mg of the title compound are obtained.

ESI: 1220. $R_t$=12.6.

Example 2.10

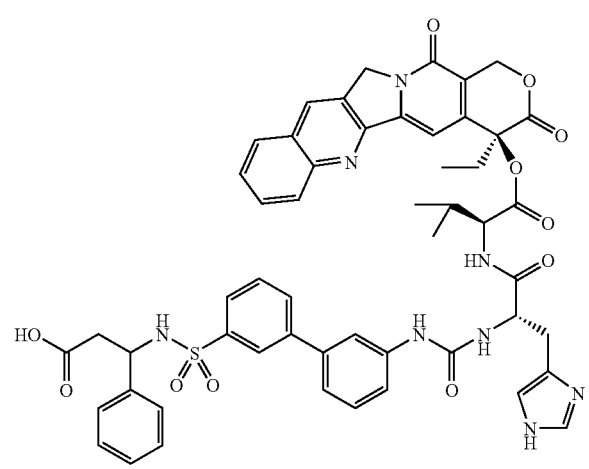

This product is prepared in analogy to Example 2.9 using starting material I.3 as the amine reagent.

ESI: 1007. $R_t$=9.2.

Example 2.11

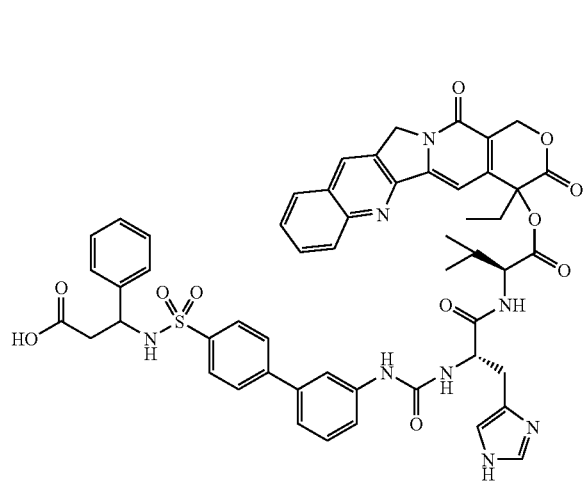

This product is prepared in analogy to Example 2.9 using 4-bromobenzenesulphonyl chloride as a sulphonylating reagent and starting material I.3 as an amine reagent.

ESI: 1007. $R_t$=9.0.

Example 2.12

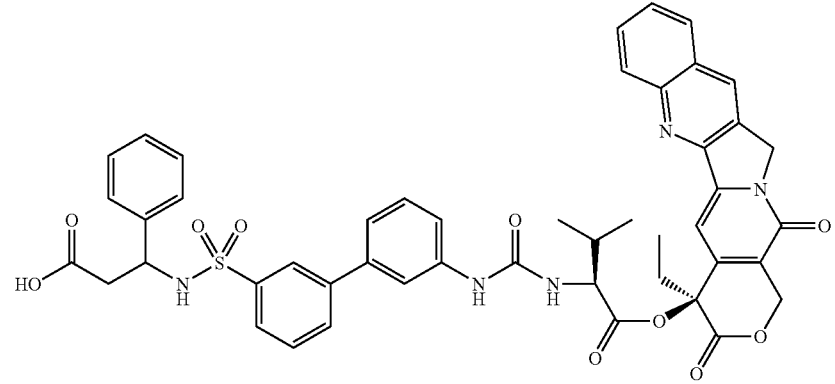

This product is prepared in analogy to Example 2.9 using 4-bromobenzenesulphonyl chloride as a sulphonylating reagent and starting material I.1 as an amine reagent.

ESI: 870. $R_t$=10.6.

Example 2.13

This product is prepared in analogy to Example 2.9 using starting material I.1 as the amine reagent.
ESI: 870. $R_t$=10.9

Example 2.14

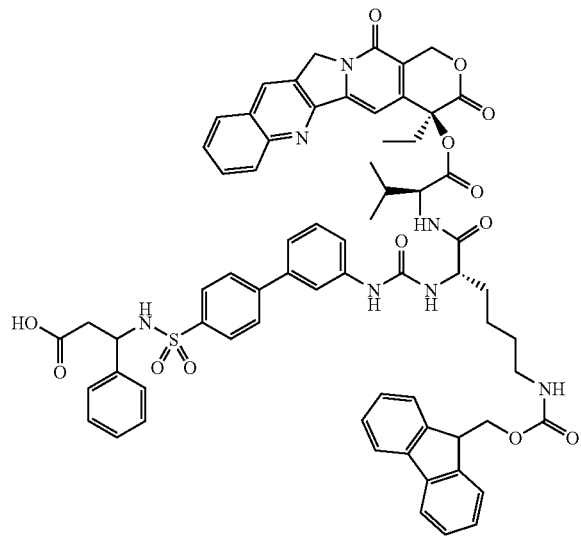

This product is prepared in analogy to Example 2.9 using 4-bromobenzenesulphonyl chloride as a sulphonylating reagent and starting material I.4 as an amine reagent.
ESI: 1220. $R_t$=12.5

3. Conjugates with Linkage Via the Side Chain of the Non-Peptide Integrin Ligand Example 3.1

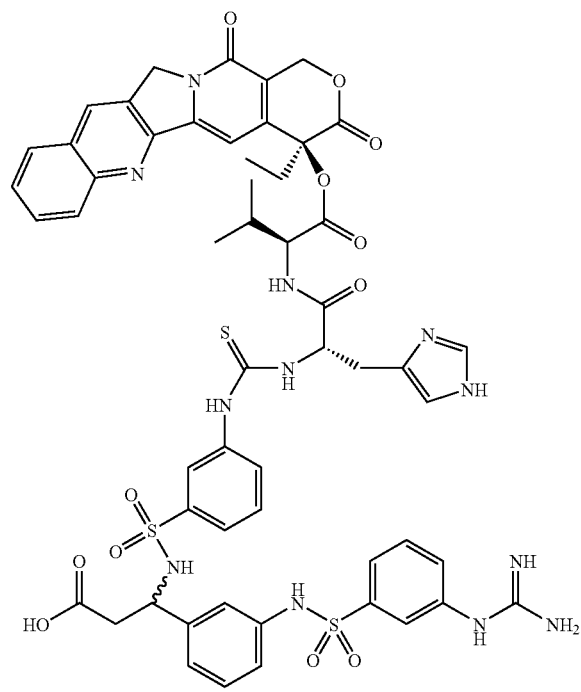

300 mg (0.5 mmol) of starting material II.1 are stirred with 80 µl of pyridine and 166 mg (1.5 eq) of m-nitrobenzenesulphonyl chloride overnight in 10 ml of dichloromethane. A further 200 ml of dichloromethane and 200 ml of water are added and the mixture is shaken thoroughly. The organic phase is collected and concentrated, and the residue is chromatographed on silica gel using dichloro-methane/methanol 99:1. After drying, 274 mg (70%) of the corresponding nitro-benzenesulphonamide are obtained.

265 mg (0.33 mmol) of the nitrobenzenesulphonamide are taken up in 30 ml of methanol and hydrogenated over palladium/carbon. After precipitating, the corresponding aminobenzenesulphonamide is obtained.

192 mg (0.25 mmol) of the corresponding aminobenzenesulphonamide are dissolved in 20 ml of methanol and the solution is stirred overnight with 504 µl (4 eq) of a 2M lithium hydroxide solution. It is concentrated, distilled off twice with dichloromethane, and, after precipitation from methanol using ether, 180 mg of the corresponding free carboxylic acid are obtained.

180 mg (0.25 mmol) of this free carboxylic acid are dissolved in 15 ml of dioxane/water (1:1) and treated with 38.5 µl of thiophosgene. After stirring at room temperature for 15 min, 172 µl (4 eq) of Hünig's base are added, and the mixture is stirred for a further 10 min and then concentrated. The residue is taken up in dichloromethane, redistilled twice and then precipitated from dichloromethane using ether. 208 mg of the corresponding isothiocyanate are obtained as a Hünig's base salt.

The Boc protective group is then removed in dichloromethane using 4 ml of trifluoroacetic acid and the unprotected guanidine is precipitated from dichloromethane/methanol using ether. 80 mg of the corresponding guanidine are obtained.

30 mg (0.037 mmol) of the corresponding guanidine are dissolved in 3 ml of DMF and then treated with 24 mg (0.8 eq) of the starting material I.3 and with 26 µl of Hünig's base. After stirring at room temperature for 20 min, the mixture is concentrated and the residue is stirred first with dichloromethane and then with methanol. Methanol is added until dissolution is complete and the mixture is precipitated using ether.

20 mg (47%) of the target product are obtained. [TLC: (acetonitrile/water/glacial acetic acid (5:1:0.2); $R_f$=0.19]. [FAB-MS: m/e 1159 $(M+H)^+$].

Example 3.2

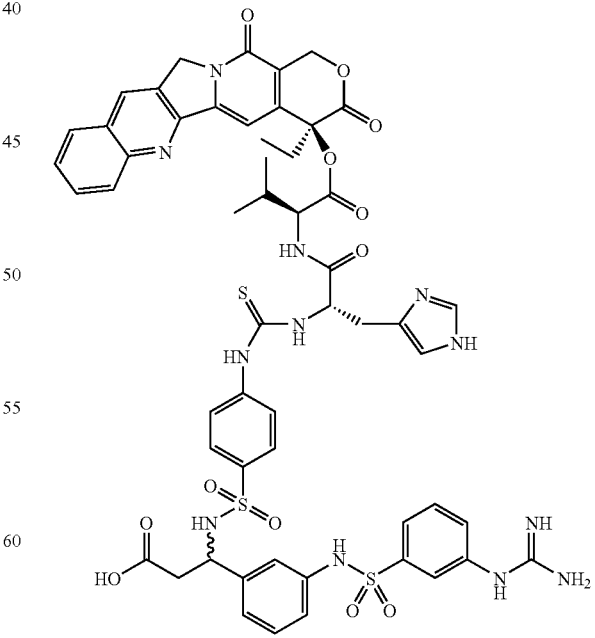

The synthesis is carried out analogously to Example 3.1 with the exception that in the first step p-nitrobenzenesulphonyl chloride is employed instead of m-nitrobenzenesulphonyl chloride.

[TLC: (acetonitrile/water/glacial acetic acid (5:1:0.2); $R_f$=0.18]. [FAB-MS: m/e=1159 (M+H)$^+$].

Example 3.3

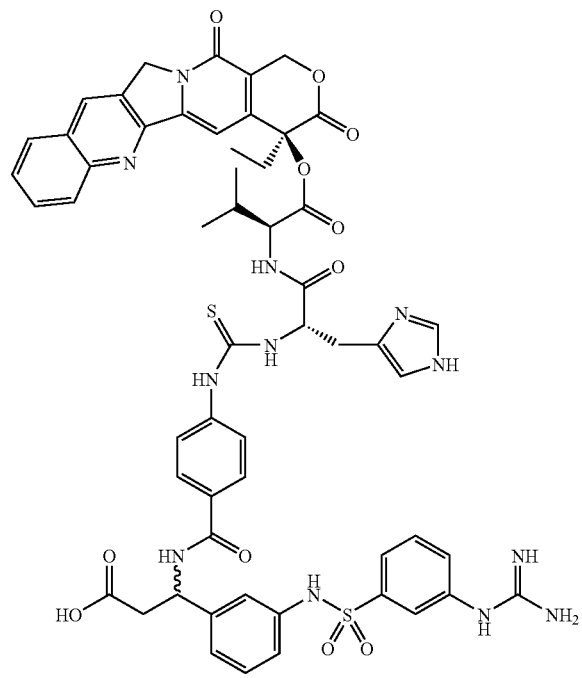

The synthesis is carried out analogously to Example 3.1 with the exception that in the first step starting material I.1 is coupled to p-aminobenzoic acid in the presence of N-(3-dimethylaminopropyl)-N'-ethylcarbodiimide hydrochloride/ hydroxybenzotriazole according to standard conditions instead of to m-nitro-benzenesulphonyl chloride.

[TLC final product: (dichloromethane/methanol/ammonia (17% strength) (15:6:0.6); $R_f$=0.25]. [FAB-MS: m/e=1123 (M+H)$^+$].

Example 3.4

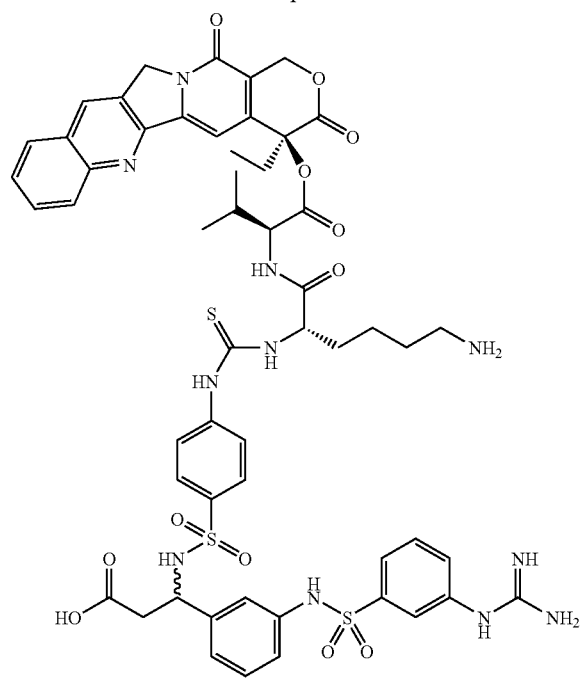

The synthesis is carried out analogously to Example 3.2 with the exception that in the last reaction step reaction takes place with starting material I.4 instead of with starting material I.3 and the Fmoc protective group is then detached according to standard conditions using piperidine. [TLC final product: (dichloromethane/methanol/ammonia (17% strength) (10:10:1); $R_f$=0.16]. [FAB-MS: m/e=1150 (M+H)$^+$].

Example 3.5

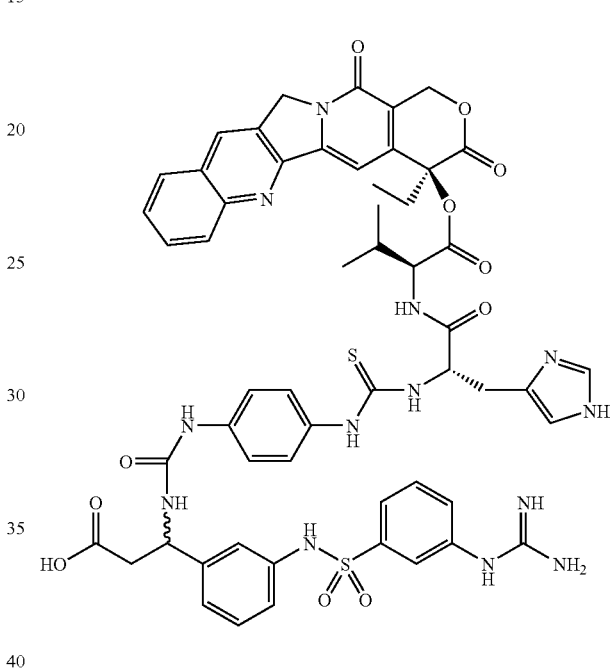

52 mg (0.073 mmol) of the Boc-protected starting material II.14 (intermediate c) are treated with 7.8 µl of thiophosgene in 5 ml of dioxane/water (1:1) and the mixture is stirred for 30 min. 37 µl of Hünig's base are then added and the mixture is concentrated.

The residue is taken up in dichloromethane and treated with 1 ml of trifluoroacetic acid. After 3 h, the mixture is concentrated and the residue is precipitated from dichloromethane/methanol using ether.

The residue obtained is dissolved in DMF as described in Example 3.1 in the last stage and then reacted with the starting material I.3 in the presence of Hünig's base.

Yield: 53%. [TLC final product: (dichloromethane/methanol/ammonia (17% strength) (15:8:0.8); $R_f$=0.26]. [FAB-MS: m/e=1138 (M+H)$^+$].

Example 3.6

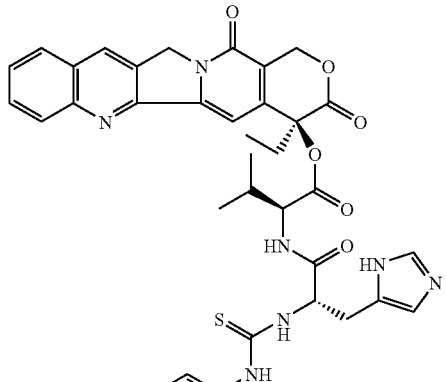

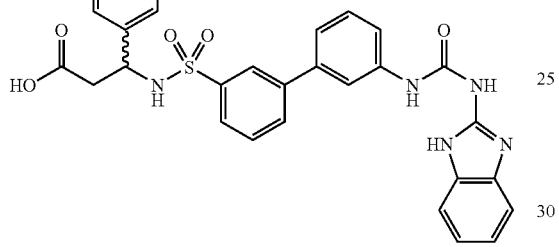

42 mg (0.074 mmol) of the starting material II.7 are dissolved in dioxane/water and treated with 8 µl of thiophosgene. After stirring at room temperature for 15 min, 38 µl of Hünig's base are added and the mixture is concentrated.

The mustard oil obtained is taken up in DMF and treated with 48 mg (0.059 mmol) of the starting material I.3 and 38 µl of Hünig's base. After stirring at room temperature for 4 h, the mixture is concentrated and the residue is precipitated from dichloromethane/methanol using ether. It is purified by flash chromatography on silica gel using dichloromethane/methanol/ammonia 17% strength 15:2:0.2. After precipitation of the resulting product from dichloromethane/methanol using ether, 10 mg (14%) of the target product are obtained.

[TLC final product: (dichloromethane/methanol/ammonia (17% strength) (15:4:0.5); $R_f$=0.25]. [FAB-MS: m/e=1197 (M+H)$^+$].

Example 3.7

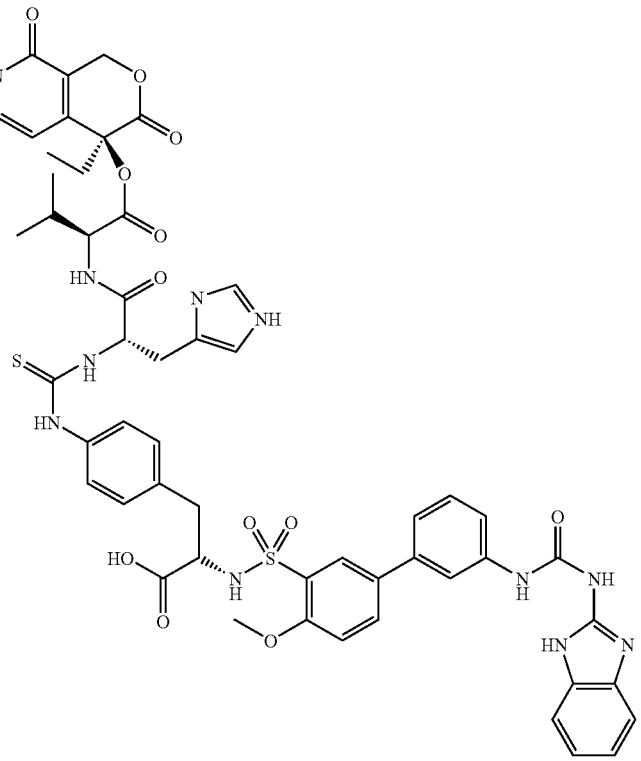

Preparation is carried out in analogy to Example 3.6 from the starting materials II.10 and I.3.
[TLC final product: (dichloromethane/methanol/ammonia (17% strength) (15:4:0.5); $R_f$=0.31]. [MALDI-MS: m/e=1227 (M+H)$^+$].
Example 3.8
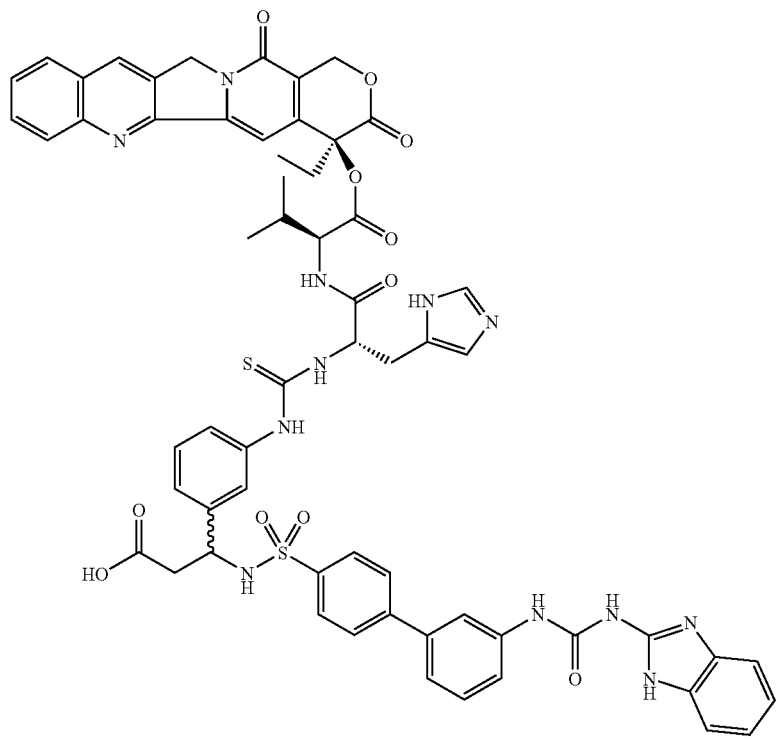

Preparation is carried out in analogy to Example 3.6 from the starting materials II.8 and I.3.
[TLC final product: (dichloromethane/methanol/ammonia (17% strength) (15:4:0.5); $R_f$=0.29]. [FAB-MS: m/e=1197 (M+H)$^+$].
Example 3.9
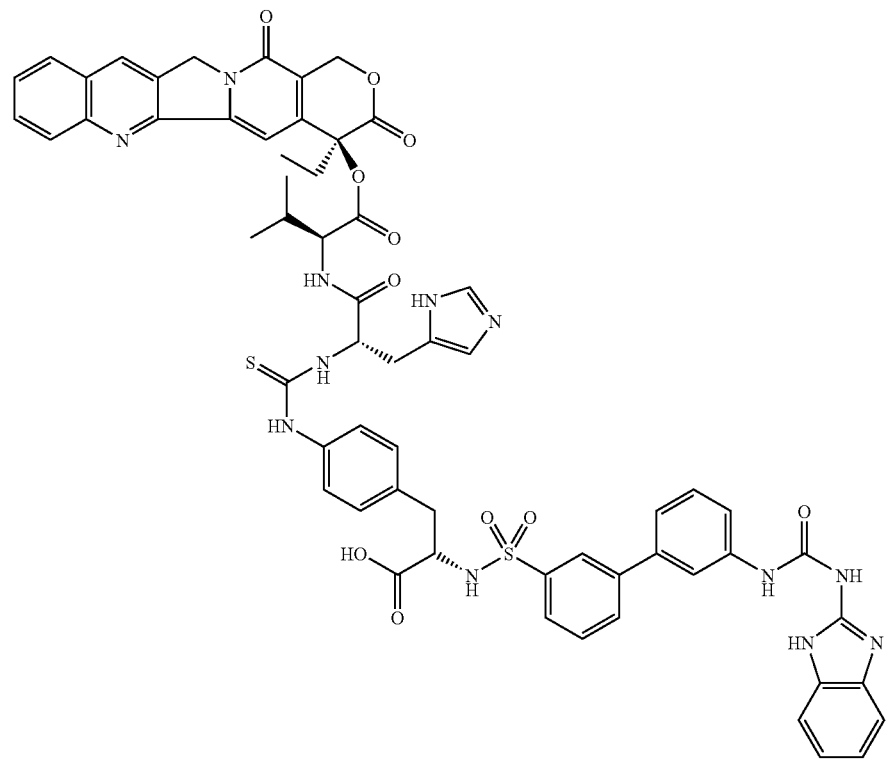

Preparation is carried out in analogy to Example 3.6 from the starting materials II.9 and I.3.

[TLC final product: (dichloromethane/methanol/ammonia (17% strength) (15:4:0.5); $R_f$=0.5]. [MALDI-MS: m/e=1197 (M+H)$^+$].

Example 3.10

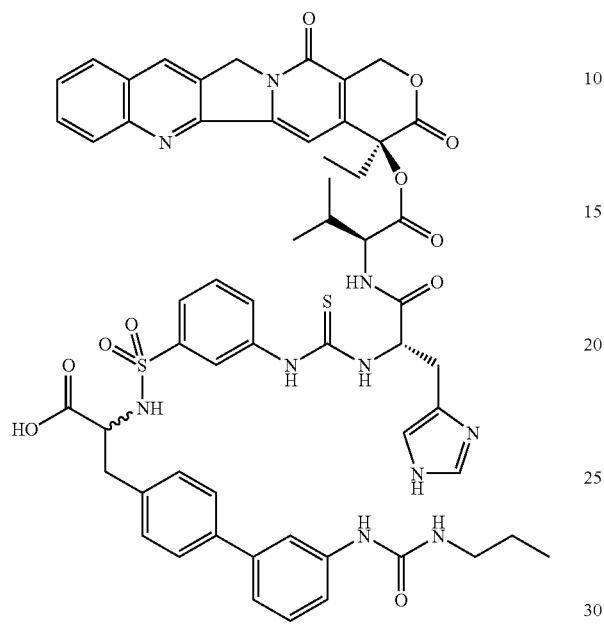

Preparation is carried out in analogy to Example 3.6 from the starting materials II.15 and I.3.

[TLC final product: (dichloromethane/methanol/ammonia (17% strength) (15:3:0.3); $R_f$=0.23]. [FAB-MS: m/e=1123 (M+H)$^+$].

Example 3.11

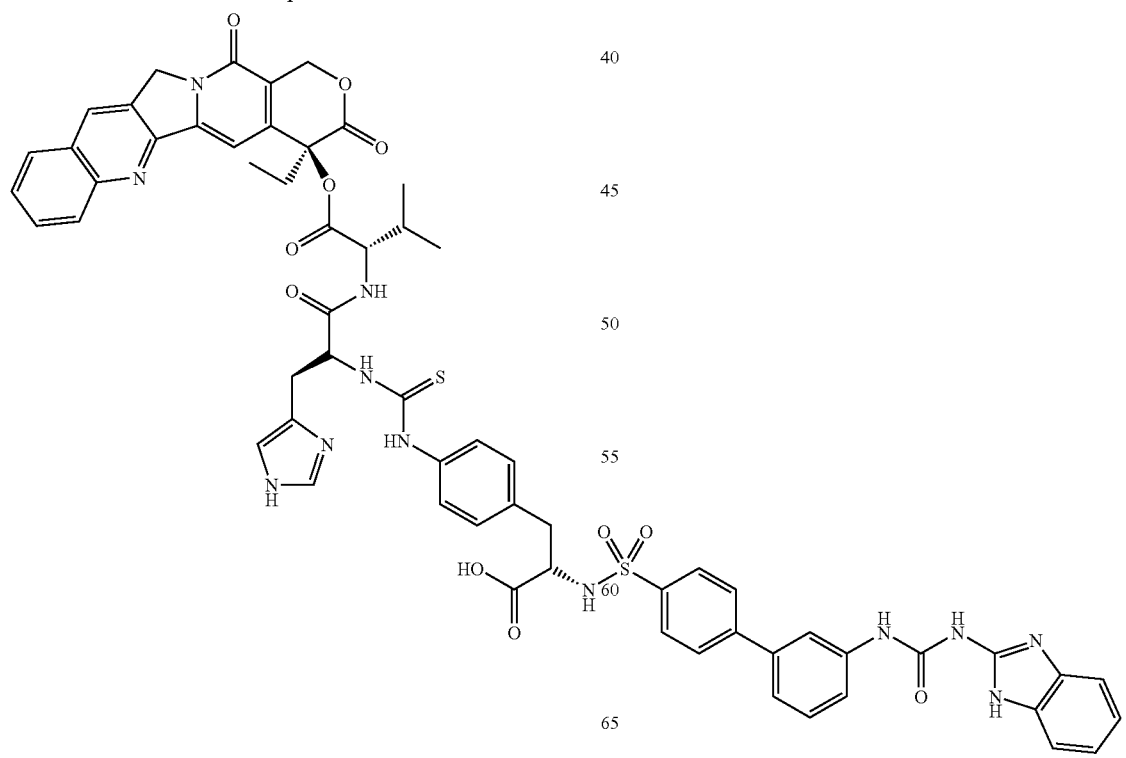

Preparation is carried out in analogy to Example 3.6 from the starting materials II.11 and I.3.

[TLC final product: (dichloromethane/methanol/ammonia (17% strength) (15:4:0.5); $R_f$=0.31]. [MALDI-MS: m/e 1197 (M+H)$^+$].

Example 3.12

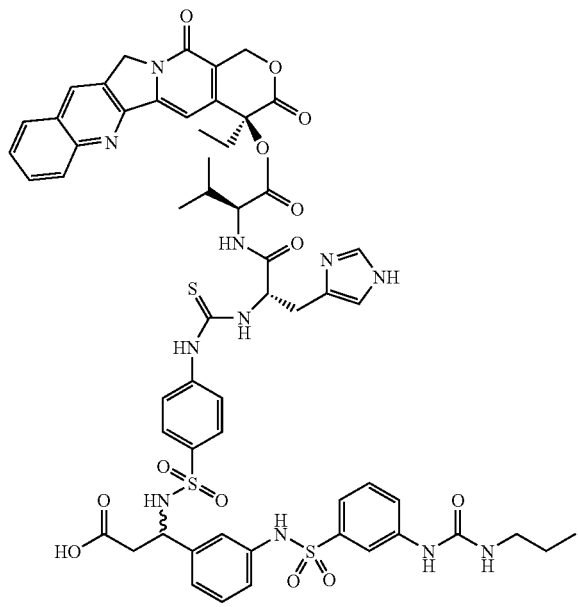

Preparation is carried out in analogy to Example 3.6 from the starting materials II.12 and I.3.

[TLC final product: (dichloromethane/methanol/ammonia (17% strength) (15:3:0.3); $R_f$=0.19]. [FAB-MS: m/e=1202 (M+H)$^+$].

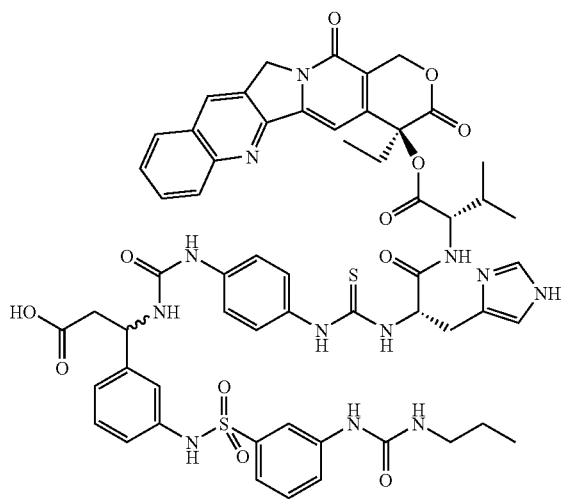

Preparation is carried out in analogy to Example 3.6 from the starting materials II.16 and I.3.

[TLC final product: (dichloromethane/methanol/ammonia (17% strength) (15:4:0.5); $R_f$=0.36]. [FAB-MS: m/e=1181 (M+H)$^+$].

Example 3.14

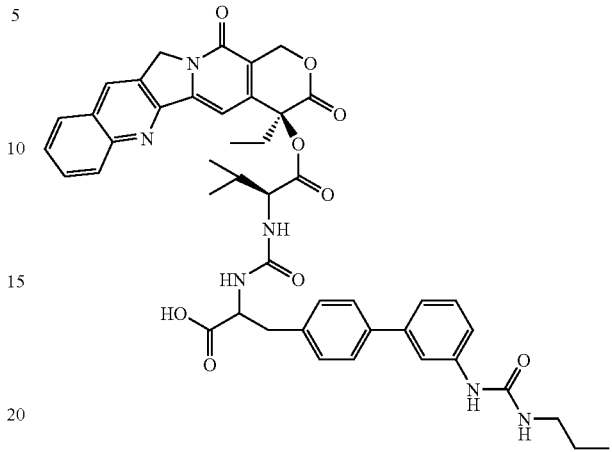

120 mg polystyrene Wang resin (loading 1.08 mmol/g) are swollen in DMF. The solvent is filtered off with suction and a solution of 110 mg of (2R,S)-3-(4-bromophenyl)-2-(9-fluorenylmethoxycarbonylamino)-propionic acid in 1.5 ml of DMF is added. After shaking at room temperature for 15 min, the suspension is treated with 35 µl of pyridine and 54 mg of 2,6-dichlorobenzoyl chloride. It is shaken overnight at room temperature. The resin is then washed with DMF, MeOH and DCM.

The resin is suspended in 700 µl of xylene, treated with 108 mg of 3-nitrobenzeneboronic acid and a solution of 137 mg of sodium carbonate in 600 µl of water and shaken at room temperature for 5 min. 23 mg of bis-(triphenylphosphine)-palladium(II) chloride and 17 mg of triphenylphosphine are then added and the mixture is stirred at 85° C. overnight. The resin is then washed with THF/water 1:1, 0.25 M aqueous hydrochloric acid, water, DMF, MeOH, THF and DCM. The resin is treated with a solution of 540 mg of Tin(II) chloride dihydrate in 1.2 ml of NMP and shaken overnight at room temperature. The resin is then washed with NMP, MeOH, THF and DCM.

The resin is treated with a solution of 57 µl of DIEA in 1.3 ml of THF/DCM 1:1 and a solution of 313 mg of 4-nitrophenylchloroformic acid ester in 1.3 ml of THF/DCM 1:1. After shaking at room temperature for 45 min, it is washed with THF and DMF and a solution of 107 mg of propylamine and 316 µl of DIEA in 2.4 ml NMP is added. After shaking for 10 h, the resin is washed with DMF, MeOH, THF and DCM.

The resin is treated with a solution of 57 µl of DIEA in 1.3 ml of THF/DCM 1:1 and a solution of 313 mg of 4-nitrophenylchloroformic acid ester in 1.3 ml of THF/DCM 1:1. After shaking at room temperature for 45 min, it is washed with THF and DMF and a solution of 260 mg of starting material I.4 (amine reagent) and 135 µl of DIEA in 800 µl of NMP is added. After shaking for 10 h, the resin is washed with DMF, MeOH, THF and DCM.

For the removal of the product, the resin is shaken with 2 ml of TFA/DCM for 1 h and filtered off, the filtrate is concentrated in vacuo and the residue is purified on silica gel. 18 mg of the title compound are obtained.

ESI: 815, $R_t$=10.0 and 10.6

Example 3.15

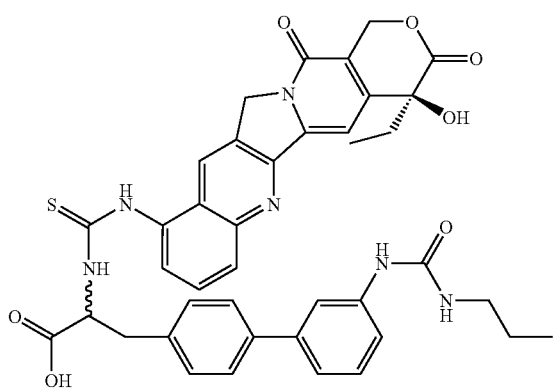

32 mg (0.088 mmol) of 9-aminocamptothecin ([prepared according to Wani et al. (J. Med. Chem. 29 (1986), 2358)] are dissolved in 6 ml of dioxane/water and treated with 9.5 µl of thiophosgene. After stirring at room temperature for 20 min, 45 µl of Hünig's base are added, and the mixture is briefly stirred and then concentrated.

The mustard oil obtained is taken up in 10 ml of DMF and treated with 30 mg (0.088 mmol) of the starting material II.6.a and 30 µl of Hünig's base. After stirring at room temperature for 3 h, the mixture is concentrated and the residue is precipitated from dichloromethane/methanol using ether. It is purified by flash chromatography on silica gel using dichloromethane/methanol (90:10). After precipitation of the resulting product from dichloromethane/methanol using ether, 8 mg (12%) of the target product are obtained.

[TLC final product: acetonitrile/water/glacial acetic acid (10:1:0.1); $R_f$=0.47]. [FAB-MS: m/e=747 (M+H)$^+$].

Example 3.16

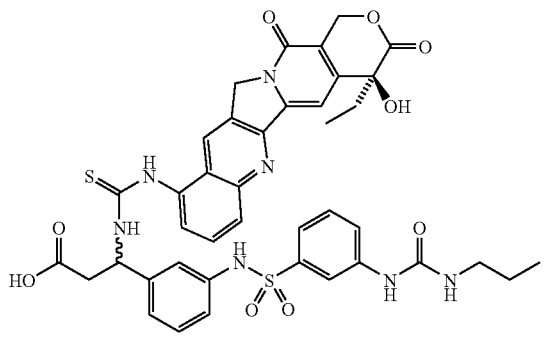

The preparation is carried out in analogy to Example 3.15 from the starting materials II.13 and 9-aminocamptothecin ([prepared according to Wani et al. (J.Med.Chem. 29 (1986), 2358)] [TLC final product: (dichloromethane/methanol/ammonia (17% strength) (15:4:0.5); $R_f$=0.38]. [ESI-MS: m/e=826 (M+H)$^+$].

Example 3.17

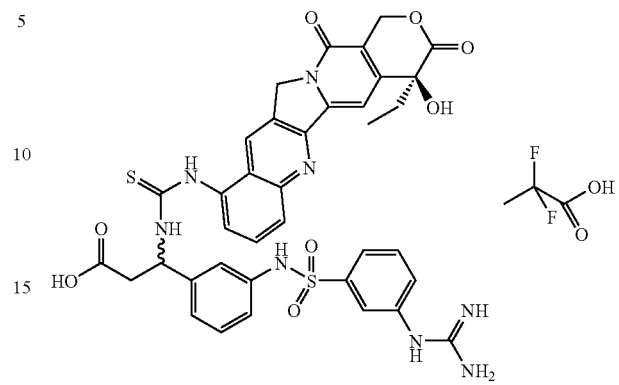

First, 200 mg of the starting material II.1 are dissolved in 10 ml of methanol and treated with 825 µl of a 2M lithium hydroxide solution and the mixture is stirred overnight. After completion of the reaction, it is concentrated and the product is precipitated from dichloromethane/methanol using ether. In addition to the ester cleavage, one of the two Boc protective groups is also detached here. The thiourea is then prepared from this intermediate and 9-aminocamptothecin ([prepared according to Wani et al. (J.Med.Chem. 29 (1986), 2358)] in analogy to Example 3.15. In the last step, the remaining Boc group is then detached using trifluoroacetic acid in dichloromethane.

[TLC final product: acetonitrile/water/glacial acetic acid (5:1:0.2); $R_f$=0.5]. [MALDI-MS: m/e=783 (M+H)$^+$].

Example 3.18

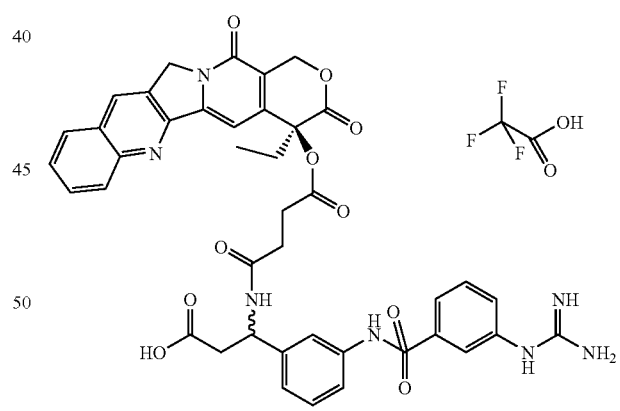

First, 200 mg of the starting material II.1 are dissolved in 10 ml of methanol and treated with 825 µl of a 2M lithium hydroxide solution and the mixture is stirred overnight. After completion of the reaction, it is concentrated and the product is precipitated from dichloromethane/methanol using ether. In addition to the ester cleavage, one of the two Boc protective groups is also detached here (intermediate a).

60 mg (0.134 mmol) of the starting material I.11 are dissolved in 5 ml of DMF and then treated with 31 mg (1.2 eq) of N-(3-dimethylaminopropyl)-N'-ethylcarbo-diimide hydrochloride and 27 mg (1.5 eq) of hydroxybenzotriazole. The mixture is stirred at room temperature for 30 min and 64 mg of the intermediate a and 69 µl of Hünig's base are then added. After stirring at room temperature for 4 h, the mixture is concentrated and the residue is stirred with 5 ml of water. The aqueous phase is concentrated and the residue is chromatographed on silica gel (dichloromethane/methanol/ammonia (17% strength) 15:1:0.1->15:2:0.2). The corresponding fractions are combined and precipitated from dichloromethane/methanol using ether (intermediate b).

Yield: 31 mg (26%) [TLC of intermediate b: (dichloromethane/methanol/ammonia (17% strength) (15:4:0.5); $R_f$=0.44].

In the last step, the remaining Boc group is then detached from 30 mg of intermediate b using 1 ml of trifluoroacetic acid in 5 ml of dichloromethane. 30 mg (100%) of the target compound are obtained.

[TLC final product: acetonitrile/water/glacial acetic acid (5:1:0.2); $R_f$=0.45]. [FAB-MS: m/e=808 (M+H)$^+$].

Example 3.19

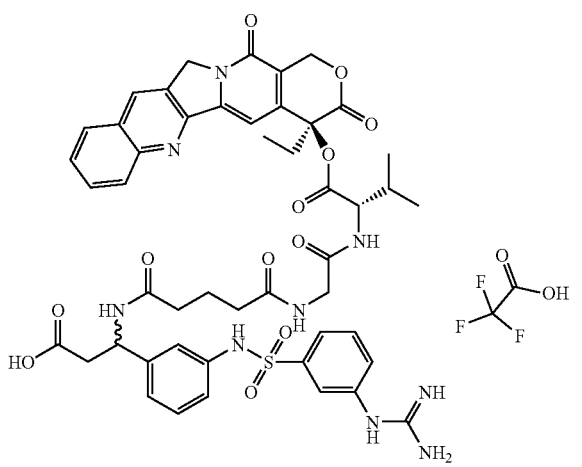

First, 200 mg of the starting material II.1 are dissolved in 10 ml of methanol and treated with 825 µl of a 2M lithium hydroxide solution and the mixture is stirred overnight. After completion of the reaction, it is concentrated and the product is precipitated from dichloromethane/methanol using ether. In addition to the ester cleavage, one of the two Boc protective groups is also detached here (intermediate a).

68 mg (0.11 mmol) of the compound starting material I.6 are dissolved in 5 ml of DMF and then treated with 25 mg (1.2 eq) of N-(3-dimethylaminopropyl)-N'-ethylcarbodiimide hydrochloride and 22 mg (1.5 eq) of hydroxybenzotriazole. The mixture is stirred at room temperature for 30 min and 52 mg of the intermediate a and 38 µl of Hünig's base are then added. After stirring at room temperature for 2 days, the mixture is concentrated and the residue is precipitated from dichloromethane/methanol using ether. The residue is chromatographed on silica gel (acetonitrile/water/glacial acetic acid (10:1:0.05). The appropriate fractions are combined, the solvent is removed by evaporation and the residue is precipitated from dichloromethane/methanol using ether (intermediate b).

Yield: 29 mg (24%) [TLC intermediate b: acetonitrile/water/glacial acetic acid (10:1:0.1); $R_f$=0.25].

In the last step, the remaining Boc group is then detached from 25 mg of intermediate b using 1 ml of trifluoroacetic acid in 5 ml of dichloromethane. After repeated precipitation from dichloromethane/methanol using ether, 18 mg (72%) of the target compound are obtained.

[TLC: acetonitrile/water/glacial acetic acid (5:1:0.2); $R_f$=0.38] [MALDI-MS: m/e 978 (M+H)$^+$].

Example 3.20

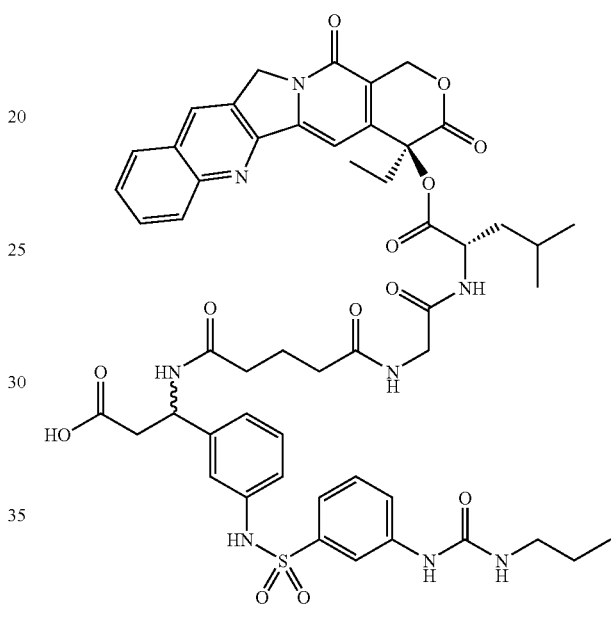

125 mg (0.2 mmol) of the compound starting material I.11 are dissolved in 5 ml of DMF and then treated with 42 mg (0.22 mmol) of N-(3-dimethylaminopropyl)-N'-ethylcarbodiimide hydrochloride and 34 mg (0.3 mmol) of N-hydroxysuccinimide. The mixture is stirred at room temperature for 2 h and then concentrated and the residue is precipitated twice from dichloromethane using ether.

10 mg (0.014 mmol) of the activated intermediate are treated with 5.8 mg of the starting material II.13 and with 4.8 µl (0.028 mmol) of Hünig's base in 4 ml of DMF and the mixture is stirred at room temperature for 4 h. It is then concentrated and the residue is chromatographed on silica gel (dichloromethane/methanol/ammonia (17% strength) 15:2:0.2->15:3:0.3). The appropriate fractions are combined and precipitated from dichloromethane/methanol using ether.

Yield: 6 mg (42%) [TLC: dichloromethane/methanol/ammonia (17% strength) (15:3:0.3) $R_f$=0.14] [ESI-MS: m/e=1035 (M+H)$^+$].

Example 3.21

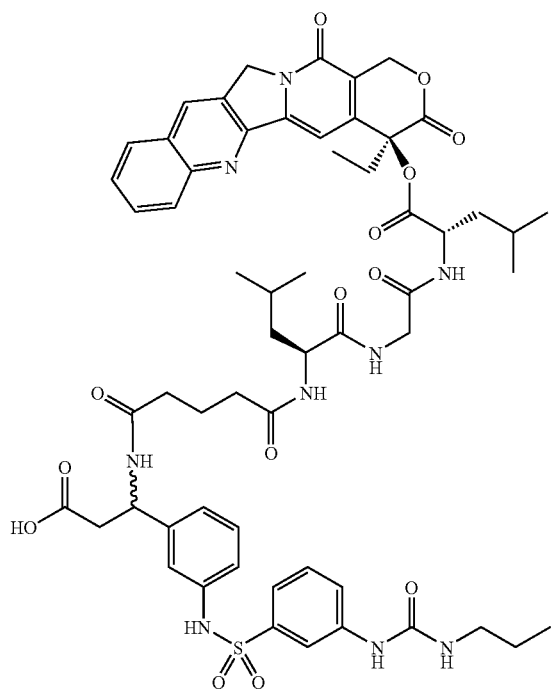

The synthesis is carried out analogously to Example 3.20 starting from the carboxy starting material I.8 and the betaine starting material II.13.

[TLC: dichloromethane/methanol/ammonia (17% strength) (15:3:0.3) $R_f$=0.18] [ESI-MS: m/e=1148 (M+H)$^+$].

Example 3.22

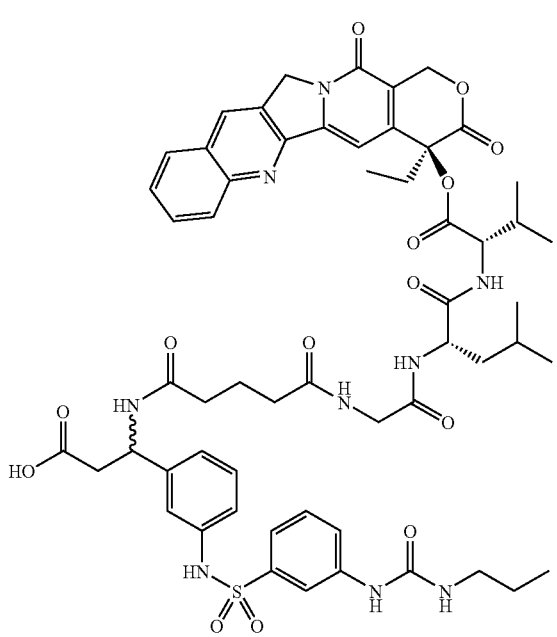

The synthesis is carried out analogously to Example 3.20 starting from the carboxy starting material I.9 and the betaine starting material II.13.

[TLC: dichloromethane/methanol/ammonia (17% strength) (15:4:0.5) $R_f$=0.42] [ESI-MS: m/e=1134 (M+H)$^+$].

Example 3.23

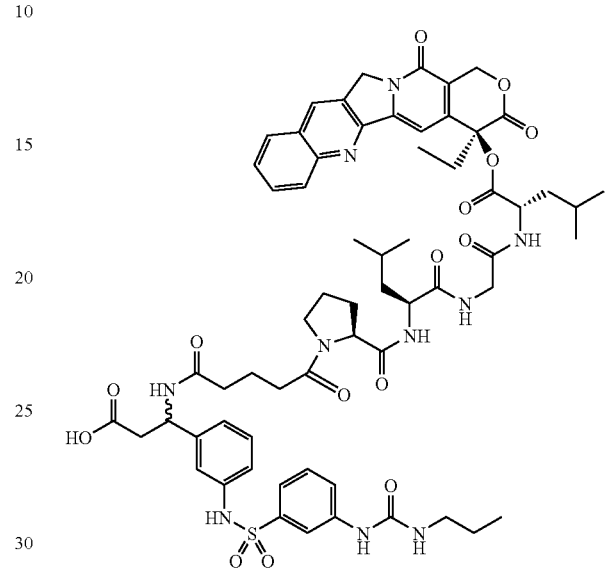

The synthesis is carried out analogously to Example 3.20 starting from the carboxy starting material I.10 and the betaine starting material II.13.

[TLC: dichloromethane/methanol/ammonia (17% strength) (15:3:0.3); $R_f$=0.24] [ESI-MS: m/e=1245 (M+H)$^+$].

Biological Tests

A: $\alpha_v\beta_3$ Binding Test $\alpha_v\beta_3$ from human A375 cells was purified analogously to a procedure which was described by Wong et al. (Molecular Pharmacology, 50, 529–537 (1996)). In each case, 10 μl of $\alpha_v\beta_3$ (5 ng) in TBS pH 7.6, 2 mM CaCl$_2$, 1 mM MgCl$_2$, 1% n-octyl-glucopyranoside (Sigma); 10 μl of test substance in TBS pH 7.6, 0.1% DMSO and 45 μl of TBS pH 7.6, 2 mM CaCl$_2$, 1 mM MgCl$_2$, 1 mM MnCl$_2$ were incubated at room temperature for 1 h. In each case, 25 μl of WGA SPA beads (Amersham, 4 mg/ml) and 10 μl of echistatin (0.1 Cci, Amersham, chloramine-T labelled) were then added. After 16 hours at room temperature, the samples were measured in a scintillation measuring apparatus (Wallac 1450). The test results are shown in Table 1 below.

TABLE 1

IC$_{50}$ values of the binding to the $\alpha_v\beta_3$ receptor [nM]

| Example | IC$_{50}$ [nM] |
|---------|----------------|
| 1.1 | 873 |
| 1.2 | 679 |
| 2.1 | 1450 |
| 2.2 | 1500 |
| 2.3 | 697 |
| 2.4 | 110 |
| 2.5 | 190 |

TABLE 1-continued

IC$_{50}$ values of the binding to the $\alpha_v\beta_3$ receptor [nM]

| Example | IC$_{50}$ [nM] |
|---|---|
| 2.6 | 239 |
| 2.7 | 86 |
| 2.8 | 83 |
| 2.9 | 236 |
| 2.10 | 101 |
| 2.11 | 197 |
| 2.12 | 127 |
| 2.13 | 97 |
| 2.14 | 84 |
| 3.1 | 147 |
| 3.2 | 45 |
| 3.3 | 45 |
| 3.4 | 65 |
| 3.5 | 36 |
| 3.6 | 22 |
| 3.7 | 111 |
| 3.8 | 25 |
| 3.9 | 220 |
| 3.10 | 154 |
| 3.11 | 97 |
| 3.12 | 390 |
| 3.13 | 14 |
| 3.14 | 21 |
| 3.15 | 61 |
| 3.16 | 51 |
| 3.17 | 66 |
| 3.18 | 79 |
| 3.19 | 48 |
| 3.20 | 265 |
| 3.21 | 549 |
| 3.22 | 531 |
| 3.23 | 355 |

B: Growth Inhibition Test for the Determination of the Cytotoxic Properties on Various Tumour Cell Lines:

The human large intestine cell lines SW 480 and HT29 (ATCC No. CCL 228 and HTB38), the human breast cell lines MDA-MB 231, MCF-7 and BT20 (ATCC No. HTB-, 26, 22 and 23) and the mouse melanoma cell line B16F 10 (CRL 6475) were grown to confluence in Roux dishes in RPMI 1640 medium with addition of 10% FCS. They were then trypsinized and taken up in RPMI plus 10% FCS to a cell count of 50,000 cells or, for B16F10, 20,000 cells per ml. 100 μl of cell suspension/well were added to a 96 microwell plate and incubated at 37° C. for 1 day in a CO$_2$ incubator. A further 100 μl of RPMI medium and 1 μl of DMSO were then added with the test substances. The growth was checked after day 6. For this, 25 μl of MTT solution (3-(4,5-dimethylthiazol-2-yl)-2,5-diphenyltetrazolium bromide) was added to each well at a starting concentration of 5 mg/ml of H$_2$O. The plate was incubated at 37° C. for 5 hours in a CO$_2$ incubator. The medium was then aspirated and 100 μl of i-propanol/well were added. After shaking with 100 μl of H$_2$O for 30 min, the extinction was measured at 595-nm using a Multiplate Reader (BIO-RAD 3550-UV).

The cytostatic action is indicated in Table 2 as an IC$_{50}$ value, in each case for the individual cell lines.

TABLE 2

IC$_{50}$ values of the cytotoxic action on tumour cell lines [nM]

| Example | SW480 | HT 29 | B16F10 | BT20 | MCF7 | MDA-MB 231 |
|---|---|---|---|---|---|---|
| 1.1 | 200 | 120 | — | 150 | 90 | 100 |
| 1.2 | 600 | 500 | 4000 | 100 | 60 | 20 |
| 2.1 | 150 | 90 | 400 | 100 | 70 | 60 |
| 2.2 | 500 | 300 | — | 400 | 300 | 300 |
| 2.3 | 120 | 70 | — | 80 | 60 | 20 |
| 2.4 | 400 | 300 | 500 | 1500 | 800 | 400 |
| 2.5 | 200 | 300 | 400 | 400 | 300 | 300 |
| 2.6 | 3000 | 3000 | 10000 | 9000 | 5000 | 3000 |
| 2.7 | 900 | 600 | 3000 | 5000 | 800 | 900 |
| 2.8 | 20 | 10 | 200 | 9 | 10 | 15 |
| 2.9 | 1000 | 700 | 300 | 1500 | 300 | 700 |
| 2.10 | 1000 | 700 | 2000 | 1000 | 1500 | 400 |
| 2.11 | 600 | 400 | 800 | 400 | 500 | 600 |
| 2.12 | 20 | 9 | 20 | 8 | 10 | 10 |
| 2.13 | 15 | 15 | 20 | 5 | 10 | 20 |
| 2.14 | 300 | 300 | 25 | 200 | 150 | 300 |
| 3.1 | 1000 | 400 | 1000 | 1000 | 800 | 500 |
| 3.2 | 400 | 200 | 1000 | 200 | 200 | 200 |
| 3.3 | 300 | 90 | — | 150 | 100 | 100 |
| 3.4 | 200 | 200 | 500 | 700 | 700 | 300 |
| 3.5 | 200 | 150 | 900 | 500 | 150 | 150 |
| 3.6 | 400 | 300 | 2000 | 1000 | 400 | 400 |
| 3.7 | 400 | 200 | 800 | 600 | 400 | 300 |
| 3.8 | 350 | 200 | 800 | 400 | 200 | 200 |
| 3.9 | 400 | 60 | 1000 | 500 | 150 | 60 |
| 3.10 | 300 | 350 | 800 | 400 | 200 | 200 |
| 3.11 | 600 | 300 | 600 | 500 | 250 | 400 |
| 3.12 | 300 | 150 | 250 | 150 | 100 | 150 |
| 3.13 | 200 | 90 | 200 | 150 | 100 | 200 |
| 3.14 | 150 | 100 | 200 | 100 | 80 | 150 |
| 3.15 | 200 | 200 | 6000 | 2000 | 300 | 200 |
| 3.16 | 500 | 100 | 1000 | 700 | 300 | 1000 |
| 3.17 | 800 | 600 | 5000 | 5000 | — | 3000 |
| 3.18 | 300 | 180 | 1000 | 900 | 600 | 500 |
| 3.19 | 1500 | 500 | 6000 | 4000 | 5000 | 2000 |

C. In-Vivo Inhibition or Tumour Growth Using a Nude Mouse Model

Material:

In all in-vivo experiments for investigating the inhibition of tumour growth, athymic nude mice (NMRI nu/nu strain) were used. The tumour was developed by serial passage in nude mice. The human origin of the tumour was confirmed by isoenzymatic and immunohistochemical methods.

Experimental Set-Up:

The tumour was implanted subcutaneously in both flanks of nu/nu nude mice 6 to 8 weeks old. The treatment was started, depending on the doubling time, as soon as the tumours had reached a diameter of 5–7 mm. The mice were assigned to the treatment group or the control group (5 mice per group having 8–10 assessable tumours) by randomization. The individual tumours of the control group all grew progressively.

The size of the tumours was measured in two dimensions by means of a slide gauge. The tumour volume, which correlated well with the cell count, was then used for all assessments. The volume was calculated according to the formula "length×breadth×breadth/2" ([a×b$^2$]/2, a and b represent two diameters arranged at right angles).

The values of the relative tumour volume (RTV) were calculated for each individual tumour by dividing the tumour size on day X with the tumour size on day 0 (at the time of randomization). The average values of the RTV were then used for the further assessment.

The inhibition of the increase of the tumour volume (tumour volume of the test group/control group, T/C, in percent) was the final measured value.

Treatment:

The compounds can be administered with a daily or an intermittent therapy schedule through a couple of days either by intraperitoneal, intravenious, oral or subcutaneous route.

The compound of example 3.8 inhibited tumor growth of the subcutaneously growing human breast cancer xenograft MX1 with an optimal T/C of 15.9 at a dose of 40 mg/kg given on day 1–3 and 14–16.

D. CSF-Induced Proliferation of Hemopoietic Stem Cells

Bone marrow cells are flushed out of the femur of mice. $10^5$ cells are incubated in McCoy 5A medium (0.3% agar) together with recombinant murine GM-CSF (Genzyme; parent cell colony formation) and the substances ($10^{-4}$ to 100 µg/ml) at 37° C. and 7% $CO_2$. 7 days later, the colonies (<50 cells) and clusters (17–50 cells) are counted.

A series of compounds exhibits a drastically reduced toxicity against stem cells in vitro compared to camptothecin.

| Example | $IC_{50}$ [ng/ml] |
|---|---|
| 3.19 | 200 |
| 3.20 | 100 |
| 3.21 | 80 |
| 3.22 | 6 |
| 3.23 | 6 |
| 3.24 | 40 |
| 3.25 | 10 |
| 3.5 | 20 |
| 3.19 | 20 |
| 3.8 | 25 |
| 3.13 | 40 |
| 3.19 | 30 |
| Camptothecin | 0.3 |

The invention claimed is:

1. A conjugate having the formula (1)

CT-AA1-AA2-AA3-AA4-Sp-IA  (I)

in which
   CT is camptothecin or 9-aminocamptothecin, which can be bonded to the rest of the conjugate via the C20—OH group or, in the case of 9-aminocamptothecin, via the free amino group;
   AA1 is absent or is a naturally occurring amino acid in the D or L configuration, which is selected from the group consisting of glycine, alanine, valine, leucine, isoleucine and phenylalanine;
   AA2 is absent or is a naturally occurring amino acid in the D or L configuration, which is selected from the group consisting of lysine, glutamate, histidine, glycine, arginine, ornithine and leucine, and can optionally carry protective groups or a radical Sp';
   AA3 is absent or is a naturally occurring amino acid in the D or L configuration, which is selected from the group consisting of glycine, alanine, valine, leucine, isoleucine and phenylalanine;
   AA4 is absent or is a naturally occurring amino acid in the D or L configuration, which can optionally carry protective groups or a radical Sp';
   in which
   Sp' is a phenylaminocarbonyl or a phenylaminothiocarbonyl radical;
   Sp is absent, is a phenylaminocarbonyl or a phenylaminothiocarbonyl radical or is an alkanedicarboxylic acid radical having 3 to 6 carbon atoms or is a carbonyl or a thiocarbonyl radical;

with the proviso that at least one of the radicals AA1 to AA4 and/or Sp is present,
   IA is a non-peptide radical addressing an $\alpha_v\beta_3$ integrin receptor, which is a radical of the formula (m)

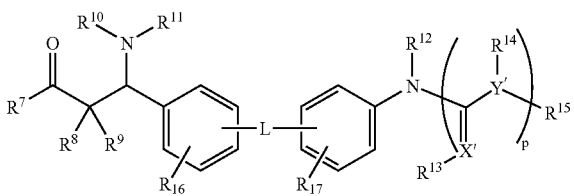

(III)

in which
   $R^7$ is OH, a substituted or unsubstituted alkoxy or cycloalkoxy radical, a substituted or unsubstituted aryloxy radical or a saturated or unsaturated, optionally substituted heterocyclyloxy radical, or optionally represents a direct bond or an atom from the group consisting of N, O and S, via which the radical of the formula (III) is bonded to the rest of the conjugate;
   R is hydrogen, a substituted or unsubstituted alkyl or cycloalkyl radical, a substituted or unsubstituted aryl radical, a saturated or unsaturated, optionally substituted heterocyclic radical, an optionally substituted alkenyl radical, an optionally substituted alkynyl radical, a hydroxyl radical or an alkoxy radical or is bonded to $R^9$ with formation of an optionally substituted carbocyclic or heterocyclic ring system which includes the carbon atom to which $R^8$ is bonded and can optionally contain heteroatoms;
   $R^9$ is hydrogen, a substituted or unsubstituted alkyl or cycloalkyl radical, a substituted or unsubstituted aryl radical, a saturated or unsaturated, optionally substituted heterocyclic radical, an optionally substituted alkenyl radical, an optionally substituted alkynyl radical, a hydroxyl radical or an alkoxy radical or is bonded to $R^8$ with formation of an optionally substituted carbocyclic or heterocyclic ring system which includes the carbon atom to which $R^9$ is bonded and can optionally contain heteroatoms;
   $R^{10}$ is —$SO_2R^{10'}$, —$COOR^{10''}$, —$COR^{10'}$, —$CONR^{10'}_2$ or —$CS$—$NR_{10'2}$, or represents a direct bond via which the radical of the formula (III) is optionally bonded to the rest of the conjugate;
   $R^{10'}$ independently of one another is hydrogen, a substituted or unsubstituted alkyl or cycloalkyl radical, a substituted or unsubstituted aryl radical or a saturated or unsaturated, optionally substituted heterocyclic radical, via which the radical of the formula (III) is optionally bonded to the rest of the conjugate;
   $R^{10''}$ is a substituted or unsubstituted alkyl or cycloalkyl radical, a substituted or unsubstituted aryl radical or a saturated or unsaturated, optionally substituted heterocyclic radical, via which the radical of the formula (III) is optionally bonded to the rest of the conjugate;
   $R^{11}$ is hydrogen, a substituted or unsubstituted alkyl or cycloalkyl radical or a substituted or unsubstituted aryl radical, $R^{16}$ is hydrogen, CN, a substituted or unsubstituted alkyl or cyclo-alkyl radical, a substituted or unsubstituted alkoxy radical or a halogen atom;

$R^{17}$ is hydrogen, CN, a substituted or unsubstituted alkyl or cyclo-alkyl radical, a substituted or unsubstituted alkoxy radical or a halogen atom;

L is —(CH$_2$)$_n$NHSO$_2$(CH$_2$)$_o$—, —(CH$_2$)$_n$SO$_2$NH(CH$_2$)$_o$—, —(CH$_2$)$_n$NHCO(CH$_2$)$_o$—, —(CH$_2$)$_n$CONH(CH$_2$)$_o$—, —(CH$_2$)$_n$OCH$_2$(CH$_2$)$_o$—, —(CH$_2$)$_n$CH$_2$O(CH$_2$)$_n$—, —(CH$_2$)$_n$COO(CH$_2$)$_o$—, —(CH$_2$)$_n$OOC—(CH$_2$)$_o$—, —(CH$_2$)$_n$CH$_2$CO(CH$_2$)$_o$—, —(CH$_2$)$_n$COCH$_2$(CH$_2$)$_o$—, —NH-CONH—, —(CH$_2$)$_n$SCH$_2$(CH$_2$)$_o$—, —(CH$_2$)$_n$CH$_2$S(CH$_2$)$_o$—, —(CH$_2$)$_n$CH$_2$SO(CH$_2$)$_o$—, —(CH$_2$)$_n$SOCH$_2$(CH$_2$)$_o$—, —(CH$_2$)$_n$CH$_2$SO$_2$(CH$_2$)$_o$— or —(CH$_2$)$_n$SO$_2$CH$_2$(CH$_2$)$_o$—, where n and o each is an integer of 0 or 1 and n+o$\leq$1;

$R^{12}$ is hydrogen, a substituted or unsubstituted alkyl or cycloalkyl radical, a substituted or unsubstituted aryl radical, a saturated or unsaturated, optionally substituted heterocyclic radical or is bonded to one of $R^{13}$, $R^{14}$ or $R^{15}$, if present, with formation of an optionally substituted heterocyclic ring system which includes the nitrogen atom, to which $R^{12}$ is bonded and can be saturated or unsaturated and/or can contain further hetero-atoms;

X is N, O or S;

p is 0 or 1;

$R^{13'}$ is absent, is —H, a substituted or unsubstituted alkyl or cyclo-alkyl radical, —NO$_2$, —CN, —COR$^{13'}$, —COOR$^{13'}$, or is bonded to one of $R^{12}$, $R^{14}$ or $R^{15}$ with formation of an optionally substituted heterocyclic ring system which includes X and can be saturated or unsaturated and/or can contain further hetero-atoms;

$R^{13}$ is hydrogen, a substituted or unsubstituted alkyl or cycloalkyl radical, a substituted or unsubstituted aryl radical or a saturated or unsaturated, optionally substituted heterocyclic radical which can be saturated or unsaturated and/or can contain further heteroatoms;

Y is N or S;

$R^{14}$ is absent, hydrogen, a substituted or unsubstituted alkyl or cycloalkyl radical, a substituted or unsubstituted aryl radical, a saturated or unsaturated, optionally substituted heterocyclic radical or is bonded to one of $R^{12}$, $R^{13}$ or $R^{15}$, if present, with formation of an optionally substituted heterocyclic ring system which includes the nitrogen atom to which $R^{14}$ is bonded and can be saturated or unsaturated and/or can contain further heteroatoms;

$R^{15}$ is hydrogen, a substituted or unsubstituted alkyl or cycloalkyl radical, a substituted or unsubstituted aryl radical, a saturated or unsaturated, optionally substituted heterocyclic radical or is bonded to one of $R^{12}$, $R^{13}$ or $R^{14}$, if present, with formation of an optionally substituted heterocyclic ring system which includes the nitrogen atom to which $R^{15}$ is bonded and can be saturated or unsaturated and/or can contain further hetero-atoms, or optionally represents a direct bond via which the radical of the formula (III) is bonded to the rest of the conjugate;

or a physiologically acceptable salt or stereoisomer thereof.

2. The conjugate according to claim 1, characterized in that

IA is a non-peptide radical of the formula (III) addressing an $\alpha_v\beta_3$ integrin receptor, in which $R^7$ is OH, methoxy, ethoxy, propoxy, isopropoxy, butoxy, isobutoxy, t-butoxy, pentoxy, isopentoxy, neopentoxy, hexoxy, cyclopropoxy, cyclopropylmethoxy, cyclobutoxy, cyclo-pentoxy, cyclohexoxy, phenoxy, benzyloxy, tolyloxy or a substituted derivative thereof, or optionally represents a direct bond or an atom from the group consisting of N, O and S, via which the radical of the formula (III) is bonded to the rest of the conjugate;

$R^8$ is hydrogen, methyl, ethyl, propyl, isopropyl, butyl, isobutyl, t-butyl, pentyl, isopentyl, neopentyl, hexyl, cyclopropyl, cyclo-butyl, cyclopentyl, cyclohexyl, cycloheptyl, phenyl, benzyl, tolyl or a substituted derivative thereof, —OH, methoxy, ethoxy, propoxy, butoxy, pentoxy, hexoxy, benzyloxy or is bonded to $R^9$ with formation of an optionally substituted 3- to 6-membered carbocyclic or heterocyclic ring system, which includes the carbon atom to which $R^8$ is bonded and can optionally contain heteroatoms;

$R^9$ is hydrogen, methyl, ethyl, propyl, isopropyl, butyl, isobutyl, t-butyl, pentyl, isopentyl, neopentyl, hexyl, cyclopropyl, cyclo-butyl, cyclopentyl, cyclohexyl, cycloheptyl, phenyl, benzyl, tolyl or a substituted derivative thereof, —OH, methoxy, ethoxy, propoxy, butoxy, pentoxy, hexoxy or is bonded to $R^8$ with formation of an optionally substituted 3- to 6-membered carbocyclic or heterocyclic ring system which includes the carbon atom to which $R^9$ is bonded and can optionally contain heteroatoms;

$R^{10'}$ is hydrogen, methyl, ethyl, propyl, isopropyl, butyl, isobutyl, t-butyl, pentyl, isopentyl, neopentyl, hexyl, cyclopropyl, cyclo-butyl, cyclopentyl, cyclohexyl, cycloheptyl, phenyl, benzyl, tolyl or a substituted derivative thereof, —C$_6$H$_2$(CH$_3$)$_3$, —C$_6$(CH$_3$)$_5$, —CH$_2$C$_6$H$_2$(CH$_3$)$_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichloro-phenyl-methyl, 2,6-dichlorophenylmethyl, 3-aminophenyl, 4-amino-phenyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, phenylmethyl, 2-acetamido-4-methylthiazol-5-yl, phenylethyl, 1-phenylpropyl, (S)-(+)-camphor-10-yl, (R)-(-)-camphor-10-yl, 2-phenylethenyl, 2-thiophenyl, 4-methoxyphenyl, 3,5-dimethoxyphenyl, 3-methylphenyl, 4-methylphenyl, 4-t-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)aniline, 4-acetamidophenyl, 2,2,2-trifluoroethyl, 5-chloro-3-methylbenzothiazol-2-yl, N-meth-oxycarbonyl-piperidin-3-yl, thiophen-2-yl, isoxazol-5-yl, ethoxy, 2-chloropyridin-3-yl, pyridin-3-yl, benzyloxy, 5-methylisoxazol-3-yl, 1-adamantyl, 4-chlorophenoxymethyl, 2,2-dimethylethenyl, 2-chloropyridine-5-methyl, 5,7-dimethyl-1,3,4-triazaindolizin-2-yl, (S)-camphan-1-yl, (R)-camphan-1-yl or 8-quinolinyl;

$R^{10'''}$ is a $C_{1-6}$-alkyl radical, a $C_{3-7}$-cycloalkyl radical, a substituted or unsubstituted aryl radical or a saturated or unsaturated, optionally substituted heterocyclic radical, via which the radical of the formula (III) is optionally bonded to the rest of the conjugate;

$R^{11}$ is hydrogen, methyl, ethyl, propyl, isopropyl, butyl, isobutyl, t-butyl, pentyl, isopentyl, neopentyl, hexyl, cyclopropyl, cyclo-propylmethyl, cyclobutyl, cyclopentyl, cyclohexyl, cyclo-heptyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, dialkylamino-$C_{1-4}$-alkyl, amino-$C_{1-4}$-alkyl, $C_{1-4}$-alkyloxy-$C_{1-4}$-alkyl or

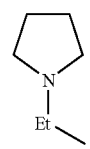 (a1)

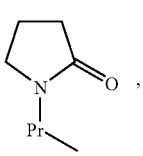 (a2)

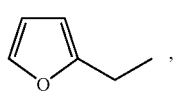 (a3)

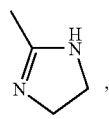 (a4)

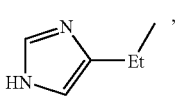 (a5)

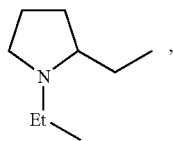 (a6)

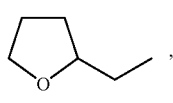 (a7)

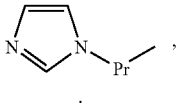 (a8)

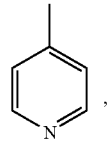 (a9)

-continued

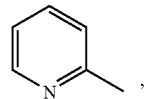 (a10)

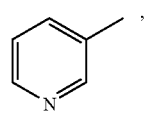 (a11)

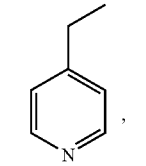 (a12)

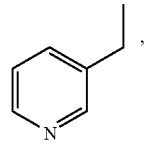 (a13)

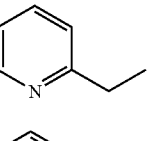 (a14)

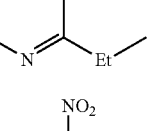 (a15)

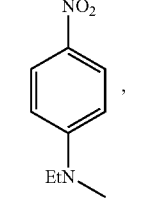 (a16)

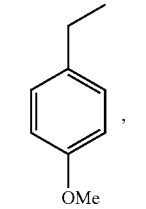 (a17)

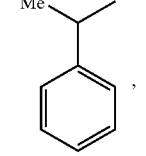 (a18)

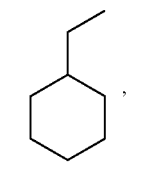 (a19)

-continued

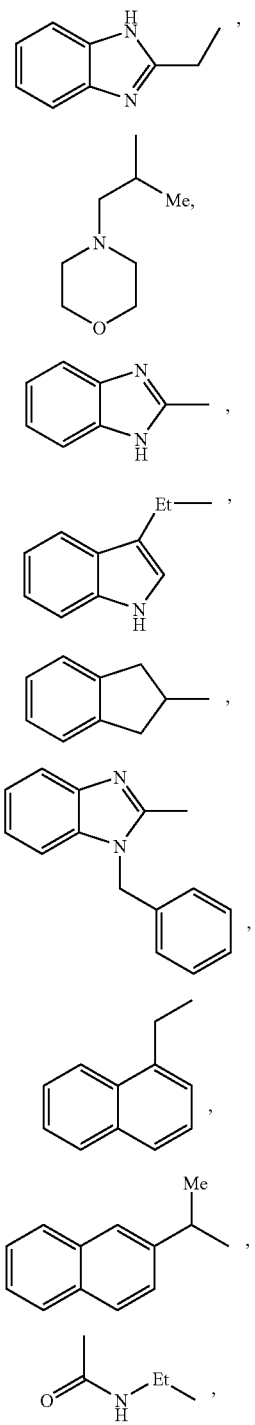

(a20)

(a21)

(a22)

(a23)

(a24)

(a25)

(a26)

(a27)

(a28)

$R^{16}$ is hydrogen, CN, methyl, ethyl, propyl, isopropyl, butyl, isobutyl, t-butyl, pentyl, isopentyl, neopentyl, hexyl, cyclo-propyl, cyclobutyl, cyclopentyl, cyclohexyl, cycloheptyl, methoxy, trifluoromethoxy, ethoxy, propoxy, butoxy, pentoxy or hexoxy, fluorine, chlorine, bromine or iodine;

$R^{17}$ is hydrogen, CN, methyl, ethyl, propyl, isopropyl, butyl, isobutyl, t-butyl, pentyl, isopentyl, neopentyl, hexyl, cyclo-propyl, cyclobutyl, cyclopentyl, cyclo-hexyl, cycloheptyl, methoxy, trifluoromethoxy, ethoxy, propoxy, butoxy, pentoxy or hexoxy, fluorine, chlorine, bromine or iodine;

L is —NHSO$_2$—, —CH$_2$NHSO$_2$—, —NHSO$_2$CH$_2$—, —SO$_2$NH—, —CH$_2$SO$_2$NH—, —SO$_2$NHCH$_2$—, —NHCO—, —CH$_2$NHCO—, —NHCOCH$_2$—, —CONH—, —CH$_2$CONH—, —CONHCH$_2$—, —OCH$_2$—, —CH$_2$OCH$_2$, —OCH$_2$CH$_2$—, —CH$_2$O— or —CH$_2$CH$_2$O—;

$R^{12}$ is hydrogen, methyl, ethyl, propyl, isopropyl, butyl, isobutyl, t-butyl, pentyl, isopentyl, neopentyl, hexyl, cyclopropyl, cyclo-propylmethyl, cyclobutyl, cyclopentyl, cyclohexyl, cyclo-heptyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino- $C_{1-4}$-alkyl, $C_{1-4}$-dialkyl-amino-$C_{1-4}$-alkyl, amino-$C_{1-4}$-alkyl, $C_{1-4}$-alkyloxy-$C_{1-4}$-alkyl, one of the radicals (a1) to (a28) or is bonded to one of $R^{13}$, $R_{14}$ or $R^{15}$, if present, with formation of an optionally substituted heterocyclic 4- to 6-membered ring system which includes the nitrogen atom to which $R^{12}$ is bonded and can be saturated or unsaturated and/or can contain further heteroatoms;

$R^{13}$ is absent, is —H, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, —NO$_2$, —CN, —COR$^{7'}$, —COOR$^{7'}$, or is connected to one of $R^{12}$, $R^{14}$ or $R^{15}$ with formation of an optionally substituted carbocyclic or heterocyclic 4- to 6-membered ring system which includes X and can be saturated or unsaturated and/or can contain further heteroatoms;

$R^{13}$ is hydrogen, methyl, ethyl, propyl, isopropyl, butyl, isobutyl, t-butyl, pentyl, isopentyl, neopentyl, hexyl, cyclopropyl, cyclobutyl, cyclopentyl, cyclohexyl, cycloheptyl, phenyl, benzyl, tolyl or a substituted derivative thereof;

$R^{14}$ is hydrogen, methyl, ethyl, propyl, isopropyl, butyl, isobutyl, t-butyl, pentyl, isopentyl, neopentyl, hexyl, cyclopropyl, cyclopropylmethyl, cyclobutyl, cyclopentyl, cyclohexyl, cycloheptyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the radicals (a1) to (a28), or is bonded to one of $R^{12}$, $R^{13}$ or $R^{15}$, if present, with formation of an optionally substituted heterocyclic 4- to 6-membered ring system which includes the nitrogen atom to which $R^{14}$ is bonded and can be saturated or unsaturated and/or can contain further heteroatoms; and $R^{15}$ is hydrogen, methyl, ethyl, propyl, isopropyl, butyl, isobutyl, t-butyl, pentyl, isopentyl, neopentyl, hexyl, cyclopropyl, cyclo-propylmethyl, cyclobutyl, cyclopentyl, cyclohexyl, cyclo-heptyl, 4-methylcyclohexyl, 3,3,5-trimethylcyclohexyl, 5-methyl-2-hexyl, phenyl, benzyl, tolyl or a substituted derivative thereof, $C_{1-4}$-alkylamino-$C_{1-4}$-alkyl, $C_{1-4}$-dialkylamino-$C_{1-4}$-alkyl, amino-$C_{1-4}$-alkyl, $C_{1-4}$-alkyloxy-$C_{1-4}$-alkyl, one of the radicals (a1) to (a28) or is bonded to one of $R^{12}$, $R^{13}$ or $R^{14}$, if present, with formation of an optionally substituted heterocyclic 4- to 6-membered ring system which includes the nitrogen atom to which $R^{15}$ is bonded and can be saturated or unsaturated and/or can contain further heteroatoms, and or optionally represents a direct bond via which the radical of the formula (III) is bonded to the rest of the conjugate.

3. The conjugate according to claim 2, wherein $R^7$ represents a direct bond or an atom from the group consisting of N, O and S, via which the radical of the formula (III) is bonded to the rest of the conjugate.

4. The conjugate according to claim 2, wherein $R^{15}$ represents a direct bond, via which the radical of the formula (III) is bonded to the rest of the conjugate.

5. The conjugate according to claim 2, wherein the radical of the formula (III) is linked to the rest of the conjugate via a radical in the α- or β-position relative to the carboxyl group.

6. A process for the preparation of conjugates according to claim 1, comprising (A) reacting a compound of the formula (III) which has a free or optionally activated carboxyl function, with a compound of the formula (Ia) which has a free primary or secondary amino group CT-AA1-AA2-AA3-AA4-Sp    (Ia)

CT is camptothecin or 9-aminocamptothecin, which can be bonded to the rest of the conjugate via the C20—OH group or, in the case of 9-aminocamptothecin, via the free amino group;

AA1 is absent or is a naturally occurring amino acid in the D or L configuration, which is selected from the group consisting of glycine, alanine, valine, leucine, isoleucine and phenylalanine;

AA2 is absent or is a naturally occurring amino acid in the D or L configuration, which is selected from the group consisting of lysine, glutamate, histidine, glycine, arginine, ornithine and leucine, and can optionally carry protective groups or a radical Sp';

AA3 is absent or is a naturally occurring amino acid in the D or L configuration, which is selected from the group consisting of glycine, alanine, valine, leucine, isoleucine and phenylalanine;

AA4 is absent or is a naturally occurring amino acid in the D or L configuration, which can optionally carry protective groups or a radical Sp';

in which

Sp' is a phenylaminocarbonyl or a phenylaminothiocarbonyl radical;

Sp is absent, is a phenylaminocarbonyl or a phenylaminothiocarbonyl radical or is an alkanedicarboxylic acid radical having 3 to 6 carbon atoms or is a carbonyl or a thiocarbonyl radical;

in the presence of a base;

or (B) reacting a compound of the formula (III) which has a free primary or secondary amino function, with a carbonic acid derivative, if appropriate in the presence of a base, followed by the reaction with a compound of the formula (Ia) which has a free primary or secondary amino group CT-AA1-AA2-AA3-AA4-Sp    (Ia)

in which all radicals have the meaning indicated above, and if appropriate removing protective groups and/or derivatizing nitrogen atoms present at preferred points of time in the preparation process and/or conversion of the compound obtained into the free acid and/or conversion of the compound obtained into one of its physiological salts by reaction with an inorganic or organic base or acid;

or (C) reacting a cytotoxic compound or a cytostatic or a cytostatic derivative CT which contains a free primary or secondary amino group, with a carbonic acid derivative in the presence of a base, followed by the reaction with a compound of the formula (III) which has a free primary or secondary amino function, and if appropriate removing protective groups and/or derivatizing nitrogen atoms present at preferred points of time in the preparation process and/or conversion of the compound obtained into the free acid and/or conversion of the compound obtained into one of its physiological salts by reaction with an inorganic or organic base or acid;

or (D) reacting a compound of the formula (III) which contains a free primary or secondary amino function, with a compound of the formula (Ia) which contains a free or optionally activated carboxyl function CT-AA1-AA2-AA3-AA4-Sp    (Ia)

in which all radicals have the meaning indicated above, in the presence of a base;

and if appropriate removing protective groups and/or derivatizing nitrogen atoms present at preferred points in time in the preparation process and/or conversion of the compound obtained into the free acid and/or conversion of the compound obtained into one of its physiological salts by reaction with an inorganic or organic base or acid.

7. The process according to claim 6, characterized in that all steps of the process are carried out on a solid phase.

8. A pharmaceutical composition comprising a conjugate according to claim 1, and a pharmaceutically acceptable carrier.

9. A method for the treatment of a carcinomatous disorder comprising administering to a host in need thereof an effective amount of a compound according to claim 1.

10. The process of claim 6 wherein said carbonic acid derivative in (B) and (C) is phosgene, thiophosgene or a chloroformic acid ester.

* * * * *